(12) United States Patent
Ji et al.

(10) Patent No.: US 12,122,994 B2
(45) Date of Patent: Oct. 22, 2024

(54) METHODS FOR FERMENTATIVE PRODUCTION OF MASSOIA LACTONE

(71) Applicant: TEMASEK LIFE SCIENCES LABORATORY LIMITED, Singapore (SG)

(72) Inventors: Lianghui Ji, Singapore (SG); Si Te Ngoh, Singapore (SG)

(73) Assignee: TEMASEK LIFE SCIENCES LABORATORY LIMITED, Singapore (SG)

(*) Notice: Subject to any disclaimer, the term of this patent is extended or adjusted under 35 U.S.C. 154(b) by 31 days.

(21) Appl. No.: 18/186,257

(22) Filed: Mar. 20, 2023

(65) Prior Publication Data

US 2023/0365915 A1 Nov. 16, 2023

Related U.S. Application Data

(62) Division of application No. 16/712,672, filed on Dec. 12, 2019, now Pat. No. 11,639,492, which is a division of application No. 15/750,584, filed as application No. PCT/SG2016/050395 on Aug. 16, 2016, now abandoned.

(60) Provisional application No. 62/205,996, filed on Aug. 17, 2015.

(51) Int. Cl.
*C12N 1/14* (2006.01)
*C12P 17/06* (2006.01)
*C12R 1/645* (2006.01)

(52) U.S. Cl.
CPC ............... *C12N 1/14* (2013.01); *C12N 1/145* (2021.05); *C12P 17/06* (2013.01); *C12N 2500/22* (2013.01); *C12N 2500/24* (2013.01); *C12N 2500/42* (2013.01); *C12R 2001/645* (2021.05)

(58) Field of Classification Search
CPC ...... C12N 1/14; C12N 1/145; C12R 2001/645
See application file for complete search history.

(56) References Cited

U.S. PATENT DOCUMENTS

2010/0267012 A1 10/2010 Bergeron et al.

FOREIGN PATENT DOCUMENTS

| CN | 102653531 | 8/2014 |
|---|---|---|
| WO | 2007025181 A2 | 3/2007 |
| WO | 2015128552 A1 | 9/2015 |

OTHER PUBLICATIONS

International Search Report and Written Opinion issued in Application No. PCT/SG2016/050395 dated Nov. 10, 2016, 18 pages.
Cene Gostinccar et al. "Genome sequencing of four Aureobasidium pullulans varieties: biotechnological potential, stress tolerance, and description of new species", BMC Genomics, 2014, vol. 15:164-15/549, 29 pages.
Julien Cescut et al. "Carbon accumulation in Rhodotorula glutinis induced by nitrogen limitation", Biotechnology for Biofuels, 2014, vol. 7:164, 11 pages.
Takafumi Kurosawa et al. "Extracellular Accumulation of the Polyol Lipids, 3,5-Dihydroxydecanoyl and 5-Hydroxy-2-decenoyl Esters of Arabitol and Mannitol, by *Aureobasidium* sp." Bioscience, Biotechnology, and Biiochemistry, Jun. 1994, vol. 58, pp. 2057-2060.
Jerry L. Slightom et al. "Cloning and molecular characterization of the gene encoding the Aureobasidin A biosynthesis complex in Aureobasidium pullulans BP-1938", Gene, 2009, vol. 431, pp. 67-79.
Singapore Written Opinion issued in Application No. 11201801204U dated Mar. 21, 2019, 9 pages.
Pan, J. G., et al., "High density cell culture of Rhodotorula Glutinis using oxygen-enriched air," Biotechnology Letters, vol. 8, No. 10, 1986, pp. 715-718.
Extended European Search Report for EP 16837405.6 dated May 21, 2019, 12 pages.
The partial supplementary European Search Report issued in application No. 16837405.6 dated Jan. 15, 2019, 10 pages.

*Primary Examiner* — Ruth A Davis
(74) *Attorney, Agent, or Firm* — ROTHWELL, FIGG, ERNST & MANBECK, P.C.

(57) ABSTRACT

A culture for the fermentative production of *Massoia* lactone comprising an *Aureobasidium melanogenum* species in a culture medium, wherein the *Aureobasidium melanogenum* species expresses no functional Aureobasidin A synthase gene mRNA when cultured, the culture medium including $KH_2PO_4$, $Na_2HPO_4$, $(NH_4)_2SO_4$, $MgSO_4 \cdot 7H_2O$ and $CaCl_2 \cdot 2H_2O$; at least two trace elements selected from the group consisting of $Fe^{2+}$, $Cu^{2+}$, $Zn^{2+}$ and $MoO_4^{2-}$; urea; and a carbon source selected from the group consisting of glucose, mannose, xylose and mixtures thereof, wherein the culture medium has a pH from 5.5 to 6.5.

20 Claims, 14 Drawing Sheets

Specification includes a Sequence Listing.

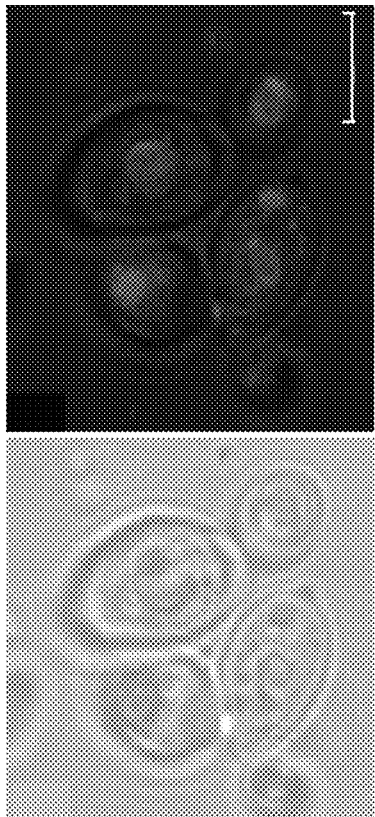
Fig. 3A Fig. 3B Fig. 3C
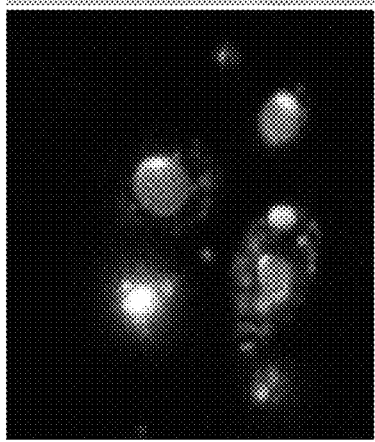
Fig. 3D
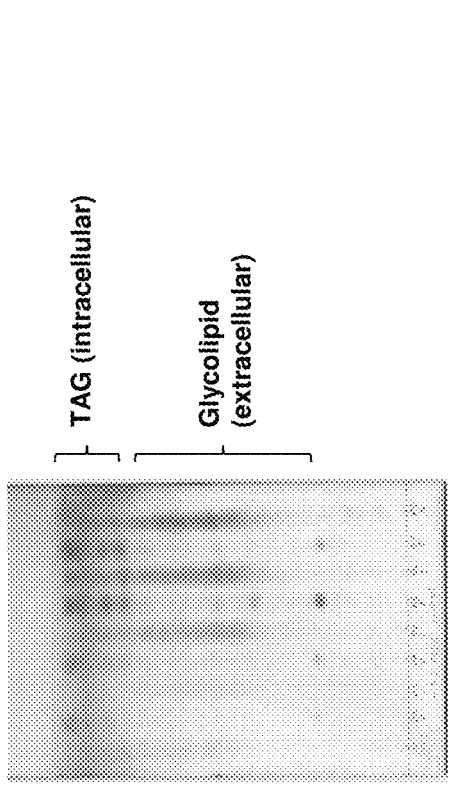

FIG. 12C

SEQUENCE LISTING

```
Sequence total quantity: 11
SEQ ID NO: 1            moltype = DNA   length = 666
FEATURE                 Location/Qualifiers
variation               36
                        note = n is a, c, g, or t
source                  1..666
                        mol_type = unassigned DNA
                        note = Aureobasidium melanogenum strain W5-2
                        organism = unidentified
SEQUENCE: 1
agcgtcccgc caaagcaaca agtagtttta acaacnaagg gttcttggtc atttagagga     60
agtaaaagtc gtaaacaagg cttccgtaag gtgaacctgc ggaaggatca ttaaagagta    120
agggtgctca gcgcccgacc tccaacccectt tgttgttaaa actaccttgt tgctttggcg   180
ggaccgctcg gtctcgagcc gctggggatt cgtcccaggc gagcgcccgc cagagttaaa    240
ccaaactctt gttatttaac cggtcgtctg agttaaaatt ttgaataaat caaaactttc    300
aacaacggat ctcttggttc tcgcatcgat gaagaacgca gcgaaatgcg ataagtaatg    360
tgaattgcag aattcagtga atcatcgaat ctttgaacgc acattgcgcc ccttggtatt    420
ccgagggcca tgcctgttcg agcgtcatta caccactcaa gctatgcttg gtattgggtg    480
ccgtcettag ttgggcgcgc cttaaagacc tcggcgaggc ctcaccggct ttaggcgtag    540
tagaatttat tcgaacgtct gtcaaaggag aggacttctg ccgactgaaa ccttttattt    600
```

```
ttctaggttg acctcggatc aggtagggat acccgctgaa cttaagcata tcaataagcg    660
gaggaa                                                               666
```

| SEQ ID NO: 2 | moltype = DNA  length = 1014 |
|---|---|
| FEATURE | Location/Qualifiers |
| source | 1..1014 |
| | mol_type = unassigned DNA |
| | note = Aureobasidium sp. |
| | organism = unidentified |

SEQUENCE: 2
```
atgcctgtca acgtcggtat taacggcttc ggtcgcattg gtcgcattgt cttccgcaat     60
gccatcgagc tcgacaacgt ccacgtcgtt gccgtcaacg ccccttcat tgagcccgag    120
tacgctgcct acatgctcaa gtcgactcc gtccacggcc agttcaaggg taccattgag    180
gtctccggca aggacctgat cgtcaacggc aagaaggtca ccttctacac cgagagagac    240
cccgccaaca tccctggc tgagactggc gcctactacg tcgtcgagtc caccggtgtc    300
ttcaccacca ccgagaaggc ctccgctcac ttgaagggtg gcgccaagaa ggtcgtcatc    360
tctgctccct ccgctgacgc ccccatgttc gtcatgggtc aacgagaa gagctacaag    420
tccgacatcc aggtcgtgtc caacgcctct tgcaccacca actgccttgc tccctcgcc    480
aaggtcatca acgacaagtt cggtatcgtt gagggtctca tgaccaccat ccactcctac    540
accgccaccc agaagaccgt cgacggtcct tccggcaagg actggcgcgg tggccgtgct    600
gctgcccaga acatcatccc cagcagcact ggtgccgcca aggctgtcgg caaggtcatt    660
cctcagctca acggcaagct gaccgtcgtg tccatgcgtg tccccaccgc caacgtctcc    720
gttgtcgacc ttactgcccg ctctcgagaag ggtgcctctt acgacaccat caagaaggcc    780
atcaaggagg cctccgaggg tgagcttaag ggcattctcg gctacaccga ggacgacatt    840
gtctcctccg acatgtgcgg tgccaacgag tcctccatct tcgacgccaa ggccggtatc    900
tcgctcaacg acaacttcgt caagcttgtc tcctggtacg caacgagtg gggttactcc    960
cgccgtgtcc tcgacctcc ggcttacatt gccaaggtca acgtaacgc ataa          1014
```

| SEQ ID NO: 3 | moltype = DNA  length = 19 |
|---|---|
| FEATURE | Location/Qualifiers |
| misc_feature | 1..19 |
| | note = oligonucleotide primer |
| source | 1..19 |
| | mol_type = other DNA |
| | organism = synthetic construct |

SEQUENCE: 3
```
tccgtaggtg aacctgcgg                                                  19
```

| SEQ ID NO: 4 | moltype = DNA  length = 20 |
|---|---|
| FEATURE | Location/Qualifiers |
| misc_feature | 1..20 |
| | note = oligonucleotide primer |
| source | 1..20 |
| | mol_type = other DNA |
| | organism = synthetic construct |

SEQUENCE: 4
```
tcctccgctt attgatatgc                                                 20
```

| SEQ ID NO: 5 | moltype = DNA  length = 35683 |
|---|---|
| FEATURE | Location/Qualifiers |
| source | 1..35683 |
| | mol_type = unassigned DNA |
| | note = Aureobasidium pullulans strain BP-1938 |
| | organism = unidentified |
| CDS | 506..35485 |
| | protein_id = 11 |
| | translation = MSRMPQGAARRNDCVSEHQGTTDLEDIVRFWERHLDGVNASAFPAL |
| | SSSLVVPKPKLQTEHRISLGTAVSDQWSDAVICRAALAVILARYTHATEALYGIVVEQP |
| | SVSNAQKRSADDASSIVVPIRVQCASGQFGNDILAAIATHDASCRSLSAIGLDGIRCLD |
| | DAKTVARGLQTVLTVTSRKSVDASSPNILDLENIASSHGRALMIECQMSTTSACLRAQY |
| | DAGILRNEQVVRLLKQLALSIQHFRGNAANDLLRDCFISPGEEMEIAYWNRRSIRTNE |
| | VCIHDVIFKRATYMPTDTAVSAWDGEWTYADLVVSSCLADYVRSLDLRSGQAIPLCFE |
| | KSRNTIAAMVAVLKAGHPFCLIDPSTPSARITQMCEQMSATVAFASRALCSIMQAGVSR |
| | CIAVDDDLFQSLSSVIGCPQMSMTRPQDLAYVIFTSGSTGIPKGSMIEHRGFASCALEF |
| | GPQLLIDRNTRALQFASHAFGACLLEVLVTLMLGGCVCVPSENDRLNNLSGFIEQSGVN |
| | WTLFTPSFIGALTPETIRGVHTVVLGGEPMTPFIRDVWASKVQLLSIYGQSESSTVCSV |
| | VKIKPDTTDLSSLGHAIGARFWIVDAENPSRLAPIGCIGELMVESPGIAREYLSAQEAQ |
| | MSPFITKTPAWYPMKQRCSPVKFYMTGDLACYGRDGTVMNLGRKDSQVKIRGQRVELGD |
| | VETNLRSVLPKHIIPVVEAIDSIHASGSKFLVAILIGANHGMKNEFDTEPRREVSILDE |
| | TAVIRIRKSMQDLVPSYCIPTQYICMERLLTTTTGKADRKRLRAICVDLLKPSRRAMVP |
| | ESSDGPTLKLTAGQVLDEAWHRYLRFDSVLDGSKSKFFDLNGDSITAIKIANAARKHGV |
| | MLKVADILANPTLADLRAQFQIDFTPQNSILRTSYRGPIQQSFAQNRLWFLDQLNVGAS |
| | WYIVPVAVRLQGTVHVDALVTALCALEQRHETLRTTFEESDGEGIQRIQPSGLEQLRLI |
| | DVDCVDSRDYQRVLEEEQTTPFELSREPGWRVALLRLGDDDHVLSIVMHHIISDGWSVD |
| | VLRHELGQFYSAALRGQDPLSQISPLPIQYRDFALWQRQDEQVAEHQRQLEHWTEQLAD |
| | SSPAELLSDHPRPSILSGQAGAIPVNVQGSLYQALRAFCRAHQVTSFVVLLTAFRIAHY |
| | RLTGAEDATIGTPIANRNRPELENMIGFFVNTQCMRIVIGSDDTFEGLVQQVRSITAAA |
| | HENQDVPFERIVSALLPGSRDTSRNPLVQLMFAVHSQRNLGQISLEGLQGELLGVASPT |
| | RFDVEFHLFQEENMLSGRVLFSDDLFEQKTMQGMVDVFQEVLSRGLEQPQIPLATLPLT |
```

```
HGLEELRTMGLLDVEKTDYPRESSVVDVFREQAAACSEAIAVKDSSAQLTYSELDRQSD
ELAGWLRQQRLPAESLVAVLAPRSCQTIVAFLGILKANLAYLPLDVNVPATRLESILSA
VGGRKLVLLGADVADPGLRLADVELVRIGDTLGRCVPGAPGDNEAPVVQPSATSLAYVI
FTSGSTGKPKGVMVEHRGVVRLVKQSNVVYHLPSTSRVAHLSNLAFDASAWEIYAALLN
GGTLICIDYFTTLDCSALGAKFIKEKIVATMIPPALLKQCLAIFPTALSELVLLFAAGD
RFSSGDAVEVQRHTKGAVCNAYGPTENTILSTIYEVKQNENFPNGVPIGRAVSNSGAYV
MDPQQQLVPLGVMGELVVTGDGLARGYTDPSLDADRFVQVSVNGQLVRAYRTGDRVRCR
PCDGQIEFFGRMDRQVKIRGHRIELAEVEHAVLGLEDVQDAAVIAFDNVDSEEPEMVGF
VTITEDNPVREDETSGQVEDWANHFEISTYTDIAAIDQGSIGSDFVGWTSMYDGSEIDK
AEMQEWLADTMASMLDGQAPGNVLEIGTGTGMVLFNLGDGLQSYVGLEPSRSAAAFVNQ
TIKSLPTLAGNAEVHIGTATDVARLDGLRPDLVVVNSVVQYFPSPEYLMEVVEALARLP
GVERIFFGDVRSYAINRDFLAARALHELGDRATKHEIRRKMLEMEEREEELLVDPAFFT
MLTSSLPGLIQHVEILPKLMRATNELSAYRYTAVVHVCRAGQEPRSVHTIDDDAWVNLG
ASRLSRPTLSSLLQTSEGASAVAVSNIPYSKTITERALVSALDEDDMQDSSDWLLAVRE
TGRSCSSFSATDLVELARETGWRVELSWARQYSQKGALDAVFHRHPVSAGSGRVMFQFP
VETEDRPHISRTNRPLQRLQKKRTETHVHEQLRALLPRYMVPTRIVALDKLPVNANGKV
DRQQLARTAQVLPASKAPSACVAPRNELEMTLCEEFSQVLGVEVGITDNFFHLGGHSLM
ATKFAARISRRLNAIVSVKNVFDHPVPMDLAATIQEGSKLHTPIPRTAYSGPVEQSFAQ
GRLWFLDQFNPSSIGYVMPFAARLHGQLQIEALTAALFALEQRHEILRTTLDAHDGVGM
QIVHAEHPQQLRIIDVSAKASSSYAQTLRDEQASPFDLSKEPGWRVSLLQLSEIDYVLS
IVMHHTIYDGWSLDVLRRELSQFYAAAIRGREPLSTIEPLPIQYRDFSVWQKQEDQVAE
HRRQLHYWIEQLDGSSPAEFLNDKPRPTLLSGKAGVVEIAVKGTVYQRLLEFCRLHQVT
SFMVLLAAFRATHYRLTGTEDATVGTPIANRNRPELENMIGLFVNTQCIRLKIEDNDTL
EELVQHVRATITASISNQDVPFEQVVSALLPGSRDTSRNPLVQLTFAVHSQRNLADIQL
ENVETNAMPICPSTRFDAEFHLFQEENMLSGRVLFSDDLFEQKTMQGMVDVFQEVLSRG
LEQPQIPLATLPLTHGLEELRTMGLLDVEKTDYPRESSVVDVFREQAAACSEAIAVKDS
SAQLTYSELDRQSDELAGWLRQQRLPAESLVAVLAPRSCQTIVAFLGILKANLAYLPLD
VNVPATRLESILSAVGGRKLVLLGADVADPGLRLADVELVRIGDTLGRCVPGAPGDNEA
PVVQPSATSLAYVIFTSGSTGKPKGVMVEHRSIVRLMRHSNVSSRLLLHPRMTHLSNLA
FDASVWEIFLTLLNGGTLICIDYLSSLDCRALGVSILEHQVDASVLPPALLKQCLANVP
EALASLQVLLSAGDRLDSRDAIESCALVRGSVYNGYGPTENGIQSTIYEVKADAEFVNG
VPIGRAVSNSGAYVMDPQQQLVPLGVMGELVVTGDGLARGYTDPSLDADRFVQVSVNGQ
LVRAYRTGDRVRCRPCDGQIEFFGRMDRQVKIRGHRIELAEVEHAVLGLEDVQDAAVLI
AQTAENEELVGFFTLRQTQAVQSNGAAGVVPEHSDSELAQSCSCTQTERRVRNRLQSCL
PRYMVPSRMVLLDRLPVNPNGKVDRQELTRRAQDLPISESSPVHVKPRTELERSLCEEF
ADVIGLEVGVTDNFFDLGGHSLMAMKLAARISRRSNAHISVKDIFDHPLIADLAMKIRE
GSDLHTPIPHRMYVGPIQLSFAQGRLWFLDQLNLGASWYVMPLAMRLQGSLQLDALETA
LFAIEQRHETLRMTFAEQDGVAVQVVHAAHYKHIKMIDKPLRQKIDVLKMLEEERTTPF
ELSREPGWRVALLRLGDDDHVLSIVMHHIISDGWSVDVLRHELGQFYSAALRGQDPLSQ
ISPLPIQYRDFALWQRQDEQVAEHQRQLEHWTEQLADSSPAELLSDHPRPSILSGQAGA
IPVNVQGSLYQALRAFCRAHQVTSFVVLLTAFRIAHYRLTGAEDATIGTPIANRNRPEL
ENMIGFFVNTQCMRIVIGSDDTFEGLVQQVRSITAAAHENQDVPFERIVSALLPGSRDT
SRNPLVQLMFAVHSQRNLGQISLEGLQGELLGVAATTRFDVEFHLFQDDDKLSGNVLFA
TELFEQKTMQGMVDVFQEVLSRGLEQPQIPLATLPLTHGLEELRTMGLLDVEKTDYPRE
SSVVDVFREQAAACSEAIAVKDSSAQLTYSELDRQSDELAGWLRQQRLPAESLVAVLAP
RSCQTIVAFLGILKANLAYLPLDVNVPATRLESILSAVGGRKLVLLGADVADPGLRLAD
VELVRIGDTLGRCVPGAPGDNEAPVVQPSATSLAYVIFTSGSTGKPKGVMVEHRSIVRL
MRHSNVSSRLLLHPRMTHLSNLAFDASVWEIFLTLLNGGTLICIDYLSSLDCRALGVSI
LEHQVDASVLPPALLKQCLANVPEALASLQVLLSAGDRLDSRDAIESCALVRGSVYNGY
GPTENGIQSTIYEVKADAEFVNGVPIGRAVSNSGAYVMDPQQQLVPLGVMGELVVTGDG
LARGYTDPSLDADRFVQVSVNGQLVRAYRTGDRVRCRPCDGQIEFFGRMDRQVKIRGHR
IELAEVEHAVLGLEDVQDAAVIAFDNVDSEEPEMVGFVTITEDNPVREDETSGQVEDWA
NHFEISTYTDIAAIDQGSIGSDFVGWTSMYDGSEIDKAEMQEWLADTMASMLDGQAPGN
VLEIGTGTGMVLFNLGDGLQSYVGLEPSRSAAAFVNQTIKSLPTLAGNAEVHIGTATDV
ARLDGLRPDLVVVNSVVQYFPSPEYLMEVVEALARLPGVERIFFGDVRSYAINRDFLAA
RALHELGDRATKHEIRRKMLEMEEREEELLVDPAFFTMLTSSLPGLIQHVEILPKLMRA
TNELSAYRYTAVVHVCRAGQEPRSVHTIDDDAWVNLGASRLSRPTLSSLLQTSEGASAV
AVSNIPYSKTITERALVSALDEDDMQDSSDWLLAVRETGRSCSSFSATDLVELARETGW
RVELSWARQYSQKGALDAVFHRHPVSAGSGRVMFQFPVETEDRPHISRTNRPLQRLQKK
RTETHVHEQLRALLPRYMVPTRIVALDKLPVNANGKVDRQQLARTAQVLPASKAPSACV
APRNELEMTLCEEFSQVLGVEVGITDNFFHLGGHSLMATKLAARISHRLHTRISVKHIF
DHPLIGDLSVHIADSPVPLLTITRAQHAGAVEQSFAQARLWFLVQLGLESPSYIIPIVL
RLHGSLSKTAIEGALSALMERHEVLRTTFEDHKGIGMQVVQDHRHQDLVVIDVAGQGSL
DYKQHLYMEHVKPFDLTRDPGWRVALLRLGDDDHVLSIVMHHIISDGWSIDILLRELGQ
FYSAALRGQDPLSQTSPLPIQYRDFALWQKQDHQLADHEKQLRYWEEQLAESSPAELLC
DHARPTTPSGQAGSIPVNVQGSLYQALRAFCRAHQVTSFVVLLTAFRIAHYRLTGAEDA
TIGTPIANRNRPELENMIGFFVNTQCMRIVIGSDDTFEGLVQQVRSITAAAHENQDVPF
ERIVSALLPGSRDTSRNPLVQLLFAVHAYQEVENFAIPGVHSELVQGTTFTRFDVEPHL
LEDPDKLSGNVLFATELFEQKTMQGMVDVFQEVLSRGLEQPQIPLATLPLTHGLEELRT
MGLLDVEKTDYPRESSVVDVFREQAAACSEAIAVKDSSAQLTYSELDRQSDELAGWLRQ
QRLPAESLVAVLAPRSCQTIVAFLGILKANLAYLPLDVNVPATRLESILSAVGGRKLVL
LGADVADPGLRLADVELVRIGDTLGRCVPGAPGDNEAPVVQPSATSLAYVIFTSGSTGK
PKGVMVEHRSILRVVTSPPARALLPSTIIMAHLTNIAFDVSLWEICTALLHGGTLICIQ
YLASLDVRGLQTTFSREAINVAVFPPALLKTCLAKIPSALASLSAMFSSGDRLDSRDAS
EGATLVRQGIHNAYGPTENGIQSTIYEVKADAEFVNGVPIGRAVSNSGAYVMDPQQQLV
PLGVMGELVVTGDGLARGYTDPSLDADRFVQVSVNGQLVRAYRTGDRVRCRPCDGQIEF
FGRMDRQVKIRGHRIELAEVEHAILSLDYVIDAAVLLRQLIDQEPQVVGFVIVSTKRAY
SRHNSGYASEVSAFCIKDQIAWRIRQHLCRMLPSYMVPYQIAILDEMPINANGKVDRQN
LASRTVNVQRILAAPYMAPRNEVEISLCEQYAALLEHDVGILDDFFELGGHSLMATRLA
```

-continued

```
SRISSRFSAPVSVRDIFDHPRIMDLASIIRAGDIQWSRILPSAYERPVEQSFAQNRLWF
LYKLDIGTTQYNLPLAIHLRGPLDISALFIAFKALTERHELLRTTFDEDDGTCLQMLLP
EYQHEVRITDLQGSHKGSLLDILNNNQKTPFELSREPGWRVALLRLGDDDHVLSIVMHH
IISDGWSVDVLRHELGQFYSAALRGQDPLSQISPLPIQYRDFALWQRQDEQVAEHQRQL
EHWTEQLADSSPAELLSDHPRPSILSGQAGAIPVNVQGSLYQALRAFCRAHQVTSFVVL
LTAFRIAHYRLTGAEDATIGTPIANRNRPELENMIGFFVNTQCMRIVIGSDDTFEGLVQ
QVRSITAAAHENQDVPFERIVSALLPGSRDTSRNPLVQLMFAVHSQRNLGQISLEGLQG
ELLGVAATTRFDVEFHLFQDDDKLSGNVLFATELFEQKTMQGMVDVFQEVLSRGLEQPQ
IPLATLPLTHGLEELRTMGLLDVEKTDYPRESSVVDVFREQAAACSEAIAVKDSSAQLT
YSELDRQSDELAGWLRQQRLPAESLVAVLAPRSCQTIVAFLGILKANLAYLPLDVNVPA
TRLESILSAVGGRKLVLLGADVADPGLRLADVELVRIGDTLGRCVPGAPGDNEAPVVQP
SATSLAYVIFTSGSTGKPKGVMVEHRGVVRLVKQSNVVYHLPSTSRVAHLSNLAFDASV
LEIYAALLNGGTVYCIDYLTTLDPHALESVFIDADLNTAVLPPALLKQVLASSPSTLHA
LDLLFIGGDRLDARDALYANRLVRGSLYNVYGPTENTVLSVVYLFNDDDACINGVPIGQ
VVSNSGVYVMDSEQKLVPPGVMGEIVVTGDGLARGYTDSTLNTDRFVQISVNGRVLQAY
RTGDRGRYRPTDARLEFFGRLDQQIKLRGHRVELKEIEQAMLGHNAVDDAGVVALEISE
CQELEMVGFVTLRNLGTMEATNNLAHTSWNPVTLKTPLASQIVAEVRGRLQRNLPLYMV
PATIVVLHTMPVNANGKLDRQALVKAAMTLPKTAPLVWMAPRNEGETSLCEELTDILGV
NVGITDNFFDLGGHSLLATRVAARISRRLDALVTVKQIFDHPVIGDLAAAIQGGSVRHL
PITASEVDGPVQQSFAQNRLWFLEQMNIGATWYIVPLAVRLYGTLRVEALNIALRTIQQ
RHETLRTTFEELNGIAVQRCDSTCQGQLRVVDLVGQGPDRYREILDVQQTTPFELSQEP
GWRVALLRLGDDDHVLSIVMHHIISDGWSVDVLREIGQFYSAALRGQDPLSQISPLPI
QYRDFALWQRQDEQVAEHQRQLEHWTEQLADSSPAELLSDHPRPSILSGQAGAIPVNVQ
GSLYQALRAFCRAHQVTSFVVLLTAFRIAHYRLTGAEDATIGTPIANRNRPELENMIGF
FVNTQCMRIVIGSDDTFEGLVQQVRSITAAAHENQDVPFERIVSALLPGSRDTSRNPLV
QLMFAVHSQRNLGQISLEGLQGELLGVAATTRFDVEFHLFQDDDKLSGNVLFATELFEQ
KTMQGMVDVFQEVLSRGLEQPQIPLATLPLTHGLEELRTMGLLDVEKTDYPRESSVVDV
FREQAAACSEAIAVKDSSAQLTYSELDRQSDELAGWLRQQRLPAESLVAVLAPRSCQTI
VAFLGILKANLAYLPLDVNVPATRLESILSAVGGRKLVLLGADVADPGLRLADVELVRI
GDTLGRCVPGAPGDNEAPVVQPSATSLAYVIFTSGSTGKPKGVMVEHRGVVRLVKQSNV
VYHLPSTSRVAHLSNLAFDASAWEIYAALLNGGTLICIDYFTTLDCSALGAKFIKEKIV
ATMIPPALLKQCLAIFPTALSELVLLFAAGDRFSSGDAVEVQRHTKGAVCNAYGPTENT
ILSTIYEVKQNENFPNGVPIGRAVSNSGAYVMDPQQQLVPLGVMGELVVTGDGLARGYT
DPSLDADRFVQVSVNGQLVRAYRTGDRVRCRPCDGQIEFFGRMDRQVKIRGHRIELAEV
EHAVLGLEDVQDAAVIAFDNVDSEEPEMVGFVTITEDNPVREDETSGQVEDWANHFEIS
TYTDIAAIDQGSIGSDFVGWTSMYDGSEIDKAEMQEWLADTMASMLDGQAPGNVLEIGT
GTGMVLFNLGDGLQSYVGLEPSRSAAAFVNQTIKSLPTLAGNAEVHIGTATDVARLDGL
RPDLVVVNSVVQYFPSPEYLMEVVEALARLPGVERIFFGDVRSYAINRDFLAARALHEL
GDRATKHEIRRKMLEMEEREEELLVDPAFFTMLTSSLPGLIQHVEILPKLMRATNELSA
YRYTAVVHVCRAGQEPRSVHTIDDDAWVNLGASRLSRPTLSSLLQTSEGASAVAVSNIP
YSKTITERALVSALDEDDMQDSSDWLLAVRETGRSCSSFSATDLVELARETGWRVELSW
ARQYSQKGALDAVFHRHPVSAGSGRVMFQFPVETEDRPHISRTNRPLQRLQKKRTETHV
HEQLRALLPRYMVPTRIVALDKLPVNANGKVDRQQLARTAQVLPASKAPSACVAPRNEL
EMTLCEEFSQVLGVEVGITDNFFHLGGHSLMATKFAARISRRLNAIVSVKNVFDHPVPM
DLAATIQEGSKLHTPIPRTAYSGPVEQSFAQGRLWFLDQFNPSSIGYVMPFAARLHGQL
QIEALTAALFALEQRHEILRTTLDAHDGVGMQIVHAEHPQQLRIIDVSAKASSSYAQTL
RDEQASPFDLSKEPGWRVSLLQLSEIDYVLSIVMHHTIYDGWSLDVLRRELSQFYAAAI
RGREPLSTIEPLPIQYRDFSVWQKQEDQVAEHRRQLHYWIEQLDGSSPAEFLNDKPRPT
LLSGKAGVVEIAVKGTVYQRLLEFCRLHQVTSFMVLLAAFRATHYRLTGTEDATVGTPI
ANRNRPELENMIGLFVNTQCIRLKIEDNDTLEELVQHVRATITASISNQDVPFEQVVSA
LLPGSRDTSRNPLVQLTFAVHSQRNLADIQLENVETNAMPICPSTRFDAEFHLFQEENM
LSGRVLFSDDLFEQKTMQGMVDVFQEVLSRGLEQPQIPLATLPLTHGLEELRTMGLLDV
EKTDYPRESSVVDVFREQAAACSEAIAVKDSSAQLTYSELDRQSDELAGWLRQQRLPAE
SLVAVLAPRSCQTIVAFLGILKANLAYLPLDVNVPATRLESILSAVGGRKLVLLGADVA
DPGLRLADVELVRIGDTLGRCVPGAPGDNEAPVVQPSATSLAYVIFTSGSTGKPKGVMV
EHRGVVRLVKQSNVVYHLPSTSRVAHLSNLAFDASAWEIYAALLNGGTLICIDYFTIID
ARALGVIFAQQSINATMLSPLLLKQFLSDAPFVLRSLHALYLGGDRLQGRDAIQACRVG
CAFVINAYGPTENSVISTTYTLVKGNADFPNGVPIGRAVSNSGAYVMDPQQQLVPLGVM
GELVVTGDGLARGYTDPSLDADRFVQVSVNGQLVRAYRTGDRVRCRPCDGQIEFFGRMD
RQVKIRGHRIELAEVEHAVLGLEDVQDAAVLIAQTAENEELVGFFTLRQTQAVQSNGAA
GVVPEHSDSELAQSCSCTQTERRVRNRLQSCLPRYMVPSRMVLLDRLPVNPNGKVDRQE
LTRRAQDLPISESSPVHVKPRTELERSLCEEFADVIGLEVGVTDNFFDLGGHSLMAMKL
AARISRRSNAHISVKDIFDHPLIADLAMKIREGSDLHTPIPHRMYVGPIQLSFAQGRLW
FLDQLNLGASWYVMPLAMRLQGSLQLDALETALFAIEQRHETLRMTFAEQDGVAVQVVH
AAHYKHIKMIDKPLRQKIDVLKMLEEERTTPFELSREPGWRVALLRLGDDDHVLSIVMH
HIISDGWSVDVLRHELGQFYSAALRGQDPLSQISPLPIQYRDFALWQRQDEQVAEHQRQ
LEHWTEQLADSSPAELLSDHPRPSILSGQAGAIPVNVQGSLYQALRAFCRAHQVTSFVV
LLTAFRIAHYRLTGAEDATIGTPIANRNRPELENMIGFFVNTQCMRIVIGSDDTFEGLV
QQVRSITAAAHENQDVPFERIVSALLPGSRDTSRNPLVQLMFAVHSQRNLGQISLEGLQ
GELLGVAATTRFDVEFHLFQDDDKLSGNVLFATELFEQKTMQGMVDVFQEVLSRGLEQP
QIPLATLPLTHGLEELRTMGLLDVEKTDYPRESSVVDVFREQAAACSEAIAVKDSSAQL
TYSELDRQSDELAGWLRQQRLPAESLVAVLAPRSCQTIVAFLGILKANLAYLPLDVNVP
ATRLESILSAVGGRKLVLLGADVADPGLRLADVELVRIGDTLGRCVPGAPGDNEAPVVQ
PSATSLAYVIFTSGSTGKPKGVMVEHRGVVRLVKQSNVVYHLPSTSRVAHLSNLAFDAS
AWEIYAALLNGGTLICIDYFTTLDCSALGAKFIKEKIVATMIPPALLKQCLAIFPTALS
ELVLLFAAGDRFSSGDAVEVQRHTKGAVCNAYGPTENTILSTIYEVKQNENFPNGVPIG
RAVSNSGAYVMDPQQQLVPLGVMGELVVTGDGLARGYTDPSLDADRFVQVSVNGQLVRA
YRTGDRVRCRPCDGQIEFFGRMDRQVKIRGHRIELAEVEHAVLGLEDVQDAAVIAFDNV
DSEEPEMVGFVTITEDNPVREDETSGQVEDWANHFEISTYTDIAAIDQGSIGSDFVGWT
```

```
              SMYDGSEIDKAEMQEWLADTMASMLDGQAPGNVLEIGTGTGMVLFNLGDGLQSYVGLEP
              SRSAAAFVNQTIKSLPTLAGNAEVHIGTATDVARLDGLRPDLVVVNSVVQYFPSPEYLM
              EVVEALARLPGVERIFFGDVRSYAINRDFLAARALHELGDRATKHEIRRKMLEMEEREE
              ELLVDPAFFTMLTSSLPGLIQHVEILPKLMRATNELSAYRYTAVVHVCRAGQEPRSVHT
              IDDDAWVNLGASRLSRPTLSSLLQTSEGASAVAVSNIPYSKTITERALVSALDEDDMQD
              SSDWLLAVRETGRSCSSFSATDLVELARETGWRVELSWARQYSQKGALDAVFHRHPVSA
              GSGRVMFQFPVETEDRPHISRTNRPLQRLQKKRTETHVHEQLRALLPRYMVPTRIVALD
              KLPVNANGKVDRQQLARTAQVLPASKAPSACVAPRNELEMTLCEEFSQVLGVEVGITDN
              FFHLGGHSLMATKLAARISRQLNIQVSVRDIFDYPVIVDLTDRLRLHHTRILTHDHGQH
              GQPDLKPFTLLPTNNPQEFLQHHILPQLVPDHAKILDVYPVTRIQRRFLHHPKRGLPRF
              PSMVFFDPPPGSDPHKLRLACMALVQRFDILRTIFLSVSGQFFQVVLDGYGIVIPVIEV
              DEELDDATRKLHDSDIQQPLRLGKPLIRIAVLKRQHSRVRAVLRLSHALYDGLSFEHII
              QSLHALYLDITLSAPPKFGLYVQHMIQSRAEGYAFWRSVLKGSSMTILERSSTLQSRQP
              HLGRFLSAEKIIKAPLHANKSGITQATVFAAANALMLANLTGTNDVVFARIVSGRQSLP
              KNFQHVVGPCTNDVPVRVRMEPGVGPKALLRQVQDQYVHSFPPETLGFDEIKENCTDWP
              ERITNFGCSTTYQNFDIFPKSQIDHQQIQMASLASEYQNRETWDEAPLYDLNVTGVPQP
              DGRHIKIYVGVDGQLCDESTLDCILSDICEGVVSLTDALQELPAASITE

SEQUENCE: 5
cgatggcaac tgttgccaac aaagcggaaa atttctctat gcggaggtgt gttacgaatc     60
tgcctaactt ttgcctcatc cactgacgac tgactaatca cagggaggtt agtgttcgct    120
gccgagggcg ccatgtcagg cgtcgcccgg cagagttgat catgcaaatt cgaagtgagc    180
accgatcaga tgagtcaagt caatatgcat tgtcttatag caacgcatca tgcgcgccac    240
aacgattctt gctgacatca cccatataca gtcataagtg tagttcgctt acggagctca    300
catgaccgca atgtctatca gagtaagcat gtctgtcgtg gctgacgctg ctctaacaat    360
gatgcgtgaa gcatcagtca atcagcaagc gaggaatact tctgccacat tgaccagact    420
atcaaccctc tgacatcgag caacacgac agcaaacgtt tgactacaac aacagccacc    480
gtatagcaac attcaacaaa caaagatgtc gcgaatgcca cagggcgcag caagacgcaa    540
cgactgtgtc tcggagcacc aaggcactac cgatctggag gatattgtgc gattctggga    600
acgcacttga gacggtgtga atgcatctgc attccctgct ctgtcatcta gcttggttgt    660
acctaaaccc aaattgcaga cagagcatcg catcagcctc ggaaccgccg tgtctgatca    720
gtggtcagat gcagtcatct gtcgagctgc acttgctgtc attttggccc gttatacgca    780
cgctactgaa gcgctctacg gcattgtggg cgagcagcct tcagtctcca atgcccagaa    840
acgatccgcc gatgatgcat cctccattgt tgtaccgatt cgtgtgcaat gtgcatctgg    900
tcaatttggg aacgatattt tggctgcaat tgctactcac gacgcttctt gtcgtagcct    960
cagcgcgatc ggcctggatg gcattgcctgc tcttgatgat gctaaaactg tggctcgggg   1020
attacagact gtattgactg taaccagcag gaagtcggtg gacgcatcaa gcccaaacat   1080
tctcgacttg gagaacatcg catcttctca cggtcgagct ctcatgatag aatgtcaaat   1140
gagcaccacc tcggcatgct tgcgtgcaca gtacgacgcg gcatcttgc gtaatgaaca   1200
ggtagttcgt cttctcaaac agctcgcgct ttcgatccga cacttccgag gtaacgctgc   1260
caacgacctg ctacgcgact tctgcttat ctcgccaggc gaagagatgg aaattgcata   1320
ctggaatcgt cgaagcattc gcacaaatga ggtttgtatc catgatgtga tctttaagag   1380
ggcgacctac atgccgactg atacggcggt ttccgcctgg gatggggagt ggacatacgc   1440
agatctagat gtcgtatctt catgtcttgc cgattacgtt cgtgtccttga atctgaggtc   1500
tggacaagcc ataccactat gcttcgaaga gtcaagaaac accatcgccg ctatggtggc   1560
cgttctcaaa gctggtcatc cgttttgcct gattgacccg tctactccat ctgcgagaat   1620
cactcagatg tgcgagcaga tgtccgctac cgtcgctttc gcttcgagag cacttttgtag   1680
catcatgcaa gcaggagtct ctagatgtat tgcagttgat gacgatctct ttcaatcctt   1740
gtcatcagtc atcgggtgtc cacagatgtc catgacgaga ccccaggacc ttgcctatgt   1800
catatttaca tccggaagta ctggaatccc gaagggcagc atgatcgagc atcgaggttt   1860
tgcaagctgc gcacttgaat tcggacctca attgttaatc gatcgcaaca cgcgtgcatt   1920
acagttcgcc tctcacgctt ttggcgcatg ctttgttagg gttctggtga cgcttatgct   1980
tggaggttgt gtatgcgtcc cgtccgaaaa cgatcgcttg aacaacctgt caggtttcat   2040
tgaacaaagc ggcgtgaact ggaccctatt tacgccttct tttattggag ctctcacgcc   2100
cgagactatt cgtggggtgc acactgtcgt gctgggtgga gagccaatga caccattcat   2160
cagaagcgta tgggcatcaa aagtgcaact ctttgtccata tatggacaaa gtgagagctc   2220
gactgtgtgt agtgtggtta aaatcaagcc tgataccacc gatctgagta gcctgggcca   2280
cgctatagga gctcgcttct ggatcgttga tgctgaaaat ccgagtcgat tgcaccaat   2340
cggctgcatc ggcgagctca tggtagagag tcctggaatt gcacgcgaat acctatctgc   2400
tcaagaagca cagatgtccc cattcataac gaagacacct gcttggtatc ctatgaagca   2460
gcgttcagt cctgtcaagt tctacatgac cggcgatctt gcttgttatg gacgtgatgg   2520
caccgtcatg aatcttggac gcaaagattt gcaagtcaag atccgaggcc aacgcgtgga   2580
gcttggcgat gtggagacta atctgcgatc agtcttacct aaaacatcat acctgttgt   2640
cgaggcgatt gattcgatcc atgcatccgg aagcaaattt ctggttgcga tcctgattgg   2700
cgcaaaccat ggaatgaaaa atgaattcga tacagagcca agactctataa ct   2760
ggatgaaacc gcggtgatcc gtataaggaa gagtatgcag gatcttgttc catcttactg   2820
catacccaca cagtatatct gcatggaacg actcctgacc acgacaacag gaaggcggaa   2880
tcgcaagaga ctacgcgcga tttgcgtgga ccttctcaag ccttcaagga gcaatggt   2940
accagaatct tcggacgggc ccactcagaa actcacggca ggacaagttt tggatgaggc   3000
atggcatcga taccgcgtt ttgattctgt tctcaagtcga agttctttga   3060
tctgaatgga gactccatca cagcgatcaa gatagcaaat gcggcgagga aacacggggt   3120
aatgctcaaa gtagcagaca ttcctgctaa tcctactctc gccgacctga gagctcaatt   3180
tcagattgat ttcacacctc aaaactccat acttcgcacc tcgtaccgtg accaatcca   3240
acaatccttt gcgcaaaaca ggttgtgtt tctggaccag ctgaacgttg gcgcgtcatg   3300
gtacatagta ccagtcgcgg tgcgcttgca aggaacagtc catgtcgacg cgcttgtcac   3360
cgcactatgt gccctggaac aacgtcatga aacgttgcgt acgaccctg aagaatccga   3420
tggcgagggc atacaacgga ttcagccaag tgggcttgag cagcttaggt tgatcgacgt   3480
ggattgcgtg gactctaggg actaccagcg agtattggaa gaagagcaga cgactcccctt   3540
cgagctgagc cgcgagcctg gatggagggt agcgctgctg cgtctgggag atgacgacca   3600
cgtcctctcc atcgtcatgc atcacatcat ctccgacggt tggtctgtgg acgtgctgcg   3660
```

```
ccacgagcta ggtcagttct actcggccgc gctccggggg caggaccegt tgtcgcagat   3720
aagtcctctg ccgatccagt atcgtgactt cgctctctgg cagagacaag acgagcaagt   3780
tgcggagcat cagcgccagc tggagcattg acagagcag ttggcagaca gttcaccege   3840
cgagttgttg agcgaccacc cgaggccatc gattctttct ggccaggegg gcgctattcc   3900
cgtcaatgtt caaggctctc tgtatcaggc gcttcgggcg ttctgccgcg ctcaccaggt   3960
cacctctttc gtagtcctgc tcacggcgtt ccgcatagca cactatcgtc tgacgggtgc   4020
ggaggacgca accattggaa ctcccattgc aaatcgcaac cggccagagc tcgagaacat   4080
gatcggtttc ttcgtcaata cacaatgcat gcgcatcgtc attggcagtg acgacacatt   4140
tgaagggctg gtgcagcaag tacgctcgat aactgcagct gcccacgaga accaggacgt   4200
tccattcgag cgcatcgtgt cagcactgct tcccggttct agagacacat cacgcaatcc   4260
tctggttcag ctcatgtttg ctgtccactc gcaaagaaac cttggtcaga tcagtctaga   4320
aggcctgcag ggtgaattgc tgggagtggc atcgccaacg agattcgatg tagagttcca   4380
cctcttccaa gaggagaata tgctaagcgg aagggtgctg ttttcagacg atcttttcga   4440
gcagaagact atgcaaggca tggtcgacgt gttccagaca gtgctcagcc ggggccttga   4500
gcagccccag atacctctgg cgaccctccc gctcacgcac ggactggagg agctcaggac   4560
catgggtctt ctcgacgtgg agaagacaga ctaccctcga gagtcgagcg tggtggacgt   4620
gttccgtgag caagcggctg cctgctccga ggcgattgcg gtcaaagact cgtcggcgca   4680
gctccacctac tcggagctcg atcgacagtc ggacgagctt gccggctggc tgcgccagca   4740
acgtcttcct gcggagtcgt tggttgcagt gctggcaccc aggtcgtgcc agaccattgt   4800
cgcgttcctg ggcatcctca aggcgaatct ggcatacctg ccgctagacg tcaacgtgcc   4860
cgctactcgc ctcgagtcga tactgtctgc cgtcggcggc cggaagctgg tcttgcttgg   4920
agctgacgtg gccgaccctg gccttcgcct ggcggatgtg gagctcgtgc ggatcggcga   4980
cacactcggc cgctgtgtac ccggggcgcc cggcgacaac gaggcacctg tggtgcagcc   5040
ttctgccaca agccttgcct acgtcatctt cacttccggc tcgaccggca agccgaaggg   5100
tgtcatggtc gagcaccggg gtgtagtgcg acttgtcaag cagagcaatg ttgtctacca   5160
tctcccgtcc acatctcgcg tggcccacct gtcgaatctc gcctttgatg cctcggcgtg   5220
ggagatctat gcggcactgc ttaatgcgcg tacactcatc tgcattgact atttcacaac   5280
tctagactgc tctgctctcg gcgccaaatt catcaaggag aagatcgtcg cgaccatgat   5340
tccgccagcg cttctgaagc aatgtctggc gatcttcccg accgctctta gtgaactggt   5400
cctgctgttt gctgccggag atcgattcag cagtggcgat gccgtcgaag tgcagcgcca   5460
caccaaaggc gctgttttta acgcgtacgg accgacagaa aacaccattc ttagtacgat   5520
ctacgaagtc aagcagaatg agaacttccc gaacggtgtg cctatcggcc gcgctgtgag   5580
caactcaggg gcatatgtca tggacccgca gcagcaactg gtgcctctcg gggtgatggg   5640
cgagctcgtc gtcaccggcg acggcctggc ccgtggttac accgaccegt cactggatgc   5700
ggaccgcttt gtgcaggtct ccgtcaacgg gcagctcgtg agagcgtacc gaacaggcga   5760
tcgcgtgcgc tgcaggcctt gcgatggcca gatcgagttc tttggacgta tggaccggca   5820
agtcaagatc cgaggacatc gcatcgagct cgcagaggta gagcatgcgg tgcttggctt   5880
ggaagacgtg caagacgctg ccgttatcgc atttgacaat gtggacagcg aagagccaga   5940
aatggttgac tttgtcacta ttaccgaaga caatcctgtc cgtgaggacg aaaccagcgg   6000
tcaagtagaa gactgggcga accacttcga gataagtacc tacaccgata tcgcggcgat   6060
cgatcagggt agcattggaa gtgactttgt aggttggact tctatgtacg acggaagcga   6120
gatcgacaag gcagagatgc aagaatggct tgccgatacc atggcctcta tgctcgacgg   6180
gcaggccgcg ggcaatgtgt tagagatagg tacaggcagt ggcatggtcc tctcaatcct   6240
cggcgacgga ctgcagagct atgtcggcct cgaaccatca agatcggcgg ccgcttttgt   6300
caaccagacg attaagtcgc tccccaccct tgctggcaac gctgaagtac acattggcac   6360
tgcgaccgac gtgcccgtc tagatggcct ccgcccgac ttagtggtag tcaattcggt   6420
agtccagtac ttcccatcac cagagtacct aatggaagtc ggtggggctc ttgcacgtct   6480
gccgggcgtc gagcgaattt tcttcggaga cgtacgttcg tacgccatca acagagattt   6540
cctggctgcc agagctctac acgaacttgg cgacagagcg actaagcacg agattcggcg   6600
aaagatgcta gagatggaag aacgcgaaga ggagctgctc gtcgacccag ctttcttcac   6660
catgttgacc agcagtctcc ctggcctgat tcagcatgtc gagatcttgc cgaagctgat   6720
gagagccact aatgagctca gcgcgtatc atacactgct gtagtacacg tgtgccgtgc   6780
cggtcaagag cctcgttccg tgcatacgat cgacgacgat gcctgggtga atcttggagc   6840
ttctcggttg agtcgcccta ccctttcaag ccttttgcaa acttccgagg gcgcatcggc   6900
cgtcgcagta agcaatattc cttacagcaa gaccatcaca gagcgagcgc tcgttagtgc   6960
gctcgatgag gatgatatgc aagactcatc ggactggctg ctggccgtgc gcgagacagg   7020
cagatcttgt tcctccttct ccgcaacaga ccttgtcgag cttgctcgag agacgggctg   7080
gcgtgtggag ctcagctggg cacgacagta ctcacagaaa ggcgcactcg atgctgtctt   7140
ccacagacac cctgttttccg ctgggagcgg gcgtgtcatg ttcagtttc cagttgagac   7200
cgaagatcga ccgcacatct cacgcacgaa ccgaccttta cagcgattgc agaagaagcg   7260
aaccgagaca catgttcatg agcagttgcg ggctttgctt ccacgataca tggttcctac   7320
gcggattgtg gcgcttgata gctgcccgt caatgcaaac ggcaaggttg atcgtcaaca   7380
gctcgctagg acagcccagg ttctcccagc gagcaaggcc ccgtctgcat gcgtggcccc   7440
acgcaacgaa ttgaaatga cactgtgtga agagttctgg caggtttctg gcgtcgaggt   7500
cggcattact gacaatttct tccacctggg tggccactct ctcatggcaa caaagttcgc   7560
cgctcgtatc agccgccggc tgaatgctat cgtttcggtc aagaatgtct tcgaccaccc   7620
cgtacctatg gatcttgcag cgacaatcca agaaggctca aagcttcata ctccaatccc   7680
tcgcacggct tacagcggtc ctgtcgaaca gtctttcgca caaggacgtc tttggttcct   7740
tgaccaattc aatcctagct cgattgggta tgtgatgcct ttcgctgcgc gtcttcatgg   7800
tcaactacaa atcgaagcgc tcacagcagc attgttcgct ttggaacagc gacatgagat   7860
cctgcgaaca acgttggacg cacacgatgg tgtaggcatg cagatcgttc acgcggaaca   7920
tccgcaacag ttgagaatca ttgatgtgtc agcaaaggcg tcgagcagtt atgctcagac   7980
actgcgtgac gagcaggcgt caccttttga cctaagcaag gaaccaggtt ggagagtctc   8040
gttgctgcag tctcagtgaga tagattatgt tcttttccatt gtaatgcatc acaccattca   8100
tgacggttgg tctctcgacg tactccggcg ggagctaagt cagttttatg ccgctgccat   8160
ccgtggtcga gaacctctat cgacaatcga gccattgcct atccaatacc gcgacttttc   8220
tgtctggcaa aagcaggaag accaagtcgc agagcatcga cgacagctcc attattggat   8280
agagcagcta gatggcagct ctcctgctga gttcctaaac gataaaccac ggcctacgtt   8340
gctttctggc aaggcaggag ttgtggaaat tgctgtgaag ggcactgtat atcaacgtct   8400
```

```
gctagagttc tgcaggcttc atcaggtcac ctcgttcatg gtgctgcttg cggcattccg   8460
agcgacacac tatcgtctga caggcacaga ggacgcgact gtcggaacac ccatcgccaa   8520
tcgcaatcga cctgagctgg agaacatgat tggattgttc gtgaatactc agtgtatacg   8580
cctcaagatc gaggacaatg atactctcga ggagctagta cagcacgttc gtgccacgat   8640
cacagcatca atctcgaacc aggatgtacc ctttgaacag gtagtgtctg cattgctacc   8700
aggatcacgc gacacctcta ggaacccact agttcagctg acttttgcgg tgcattctca   8760
gcgaaatttg gctgacattc agctagaaaa cgtggagacc aatgctatgc caatttgccc   8820
ctcgacacgt ttcgacgctg aattccacct cttccaagag gagaatatgc taagcggaag   8880
ggtgctgttt tcagacgatc ttttcgagca gaagactatg caaggcatgg tcgacgtgtt   8940
ccaggaagtg ctcagccggg gccttgagca gccccagata cctctggcga ccctcccgct   9000
cacgcacgga ctgaggagc tcaggaccat gggtcttctc gacgtggaga agacagacta   9060
ccctcgagag tcgagcgtgg tggacgtgtt ccgtgagcaa gcggctgcct gctccgaggc   9120
gattgcggtc aaagactcgt cggcgcagct cacctactcg gagctcgatc gacagtcgga   9180
cgagcttgcc ggctggctgc gccagcaacg tcttcctgcg gagtcgttgg ttgcagtgct   9240
ggcacccagg tcgtgccaga ccattgtcgc gttcctgggc atcctcaagg cgaatctggc   9300
atacctgccg ctagacgtca acgtgcccgc tactcgcctc gagtcgatac tgtctgccgt   9360
cggcggccgg aagctggtct tgcttggagc tgacgtggcc gaccctggcc ttcgcctggc   9420
ggatgtggag ctcgtgcgga tcggcgacac actcggccgc tgtgtacccg gggcgcccgg   9480
cgacaatgag gcacctgtgg tgcagccttc tgccacaagc cttgcctacg tcatcttcac   9540
ttccggctcg accggcaagc cgaagggtgt catggtcgag caccgtagta tcgtccgctt   9600
gatgaggcac agcaatgtct cgagtcgcct tctgctacat ccccgcatga cccacctgtc   9660
gaatctcgcc ttcgatcgt cggtgtggga gattttcttg acgctgctca acggtggaac   9720
attgatttgt attgactacc tctcgtcact agactgtcgt gctcttgggg taagtatcct   9780
ggaacaccag gttgacgcat cggtacttcc tcctgctttg ctcaaacaat gcctagcaaa   9840
tgtccctgag gcacttgcga gcctgcaagt gctcttgtcc gctggagatc gactcgacag   9900
tcgtgatgct atagagagtt gcgcactcgt gcgcggaacg gtctacaatg ggtatggtcc   9960
cacgagaat ggcatccaga gcacaatcta tgaagtcaaa gcggacgctg agtttgtcaa   10020
tggtgtgcct atcggccgcg ctgtgagcaa ctcaggggca tatgtcatgg acccgcagca   10080
gcaactggtg cctctcgggg tgatgggcga gctcgtcgtc accggcgacg gcctggcccg   10140
tggttacacc gacccgtcac tggatgcgga ccgctttgtg caggtctccg tcaacgggca   10200
gctcgtgaga gcgtaccgaa caggcgatcg cgtgcgctgc aggccttgcg atggccagat   10260
cgagttcttt ggacgtatgg accggcaagt caagatccga ggacatcgca tcgagctcgc   10320
agaggtgagg catgcggtgc ttggcttgga agacgtgcaa gacgctgccg ttctcatagc   10380
tcaaacagcc gaaaatgaag agctagttgg cttcttcaag cttcgacaaa cccaggctgt   10440
gcagtcaaat ggtgccgctg gtgttgtgcc agagcacagc gactccgagc tggccaatc   10500
ctgctcttgc actcaaacgg agcgtcgagt ccgcaacaga ttgcaatcct gtcttcctcg   10560
ctacatggtt ccgtcgcgaa tggtccttt ggatcgactg cctgtcaacc ccaatggtaa   10620
agttgatcga caagagctca cgaggcgcgc tcaggatctc ccaataagcg agtcatcccg   10680
agtgcacgtc aaaccgcgta ctgaactgga aagtcgcgtg tgcgaggagt tgccgatgt   10740
tataggtttg gaagtcggcg ttaccgataa tttcttcgac ctaggcgggc actctctcat   10800
ggcgatgaaa ctcgcagctc gcatcagccg tcgttcgaat gcacatatat cagtcaagga   10860
cattttcgac caccgctga ttgcagatct cgcaatgaaa attcgggaag ctccgatct   10920
gcacactcca attcccacca ggatgtacgt tggacctatc cagctatcat tcgcacaggg   10980
acgcttgtgg ttcctcgacc aattgaattt gggcgcatcg tggtacgtca tgccacttgc   11040
tatgcgcctc caaggctcgc tccagctcga cgcgttagag actgcactgt ttgctatcga   11100
gcagcgacac gaaaccttac ggatgacatt tgcagaacaa gacggagtag ctgtacaagt   11160
agtgcatgca gcccactaca aacacatcaa gatgatcgac aaaccacta gacagaagat   11220
tgacgtcctg aagatgctgg aagaagaacg gacgactccc ttcgagctga gccgcgagcc   11280
tggatggagg gtagcgctgc tgcgtctggg agatgacgac cacgtcctct ccatcgtcat   11340
gcatcacatc atctccgacg gttggtctgt ggacgtgctg cgccacgagc taggtcagtt   11400
ctactcggcc gcgctccggg ggcaggacc gtttgtcgca ataagtcctc tgccgatcca   11460
gtatcgtgac ttcgctctct ggcagagaca agacgagcaa gttgcggagc atcagcgcca   11520
gctggagcat tggacagagc agttggcaga cagttcaccc gccgagttgt tgagcgacca   11580
cccgaggcca tcgattcttt ctggccaggc gggcgctatt cccgtcaatg ttcaaggctc   11640
tctgtatcag gcgcttcggg ccgttctgcc cgctcaccag gtcacctctt tcgtagtcct   11700
gctcacggcg ttccgcatag cacactatcg tctgacgggt gcggaggacg caaccattgg   11760
aactcccatt gcaaatcgca accggccaga gctcgagaac atgatcggtt tcttcgtcaa   11820
tacacaatgc atgcgcatcg tcattggcag tgacgacaca tttgaagggc tggtgcagca   11880
agtacgctcg ataactgcag ctgcccacga gaaccaggac gttccattcg agcgcatcgt   11940
gtcagcactg cttcccggtt ctagagacac atcacgcacat cctctggttc agctcatgtt   12000
tgctgtccac tcgcaaagaa accttggtca gatcagtcta gaaggcctgc agggtgaatt   12060
gctgggagtg gcagcgacta cgagattcga tgtagagttc catctcttcc aagatgacga   12120
caagctcagc ggcaacgtgc tcttcgcgac cgagctcttc gagcagaaga ctatgcaagg   12180
catggtcgac gtgttccagg aagtgctcag ccggggccct gagcagccca agatacctct   12240
ggcgaccctc ccgctcacgc acggactgga ggagctcagg accatgggtc ttctcgacgt   12300
ggagaagaca gactaccctc gagagtcgag cgtggtggac gtgttccgtg agcaagcggc   12360
tgcctgctcc gaggcgattg cggtcaaaga ctcgtcggcg cagctcacct actcggagct   12420
cgatcgacag tcggacgagc ttgccggctg gctgcgcag caacgtcttc ctgcggagtc   12480
gttggttgca gtgctggcac caggtcgtg ccagatcatt gtcgcgttcc tgggcatcct   12540
caaggcgaat ctggcatacc tgccgctaga cgtcaacgtg cccgctactc gcctcgagtc   12600
gatactgtct gccgtcggcg gccggaagct ggtcttgctt ggagctgacg tggccgaccc   12660
tggccttcgc ctgcggatg tggagctcgt gcggatcggc gacacactcg gccgctgtgt   12720
acccggggcg cccggcgaca atgaggcacc tgtggtgcag ccttctgcca caagccttgc   12780
ctacgtcatc ttcacttccg gctcgaccgg caagccgaag ggtgtcatgg tcgagcaccg   12840
tagtatcgtc cgcttgatga ggcacagcaa tgtctcgagt cgccttctgc tacatccccg   12900
catgacccac ctgtcgaatc tcgccttcga tcgcggtg tgggagattt tcttgacgct   12960
gctcaacggt ggaacattga tttgtattga ctacctctcg tcactagact gtcgtgctct   13020
tggggtaagt atcctggaac accaggttga cgcatcggta cttcctcctg ctttgctcaa   13080
acaatgccta gcaaatgtcc ctgaggcact tgcgagcctg caagtgctct tgtccgctgg   13140
```

-continued

```
agatcgactc gacagtcgtg atgctataga gagttgcgca ctcgtgcgcg gaagtgtcta  13200
caatgggtat ggtcccacgg agaatggcat ccagagcaca atctatgaag tcaaagcgga  13260
cgctgagttt gtcaatggtg tgcctatcgg ccgcgctgtg agcaactcag ggcatatgt   13320
catgacccg cagcagcaac tggtgcctct cggggtgatg ggcgagctcg tcgtcaccgg   13380
cgacggcctg gcccgtggtt acaccgaccc gtcactggat gcggaccgct ttgtgcaggt   13440
ctccgtcaac gggcagctcg tgagagcgta ccgaacaggc gatcgcgtgc gctgcaggcc   13500
ttgcgatggc cagatcgagt tctttggacg tatggaccgg caagtcaaga tccgaggaca   13560
tcgcatcgag ctcgcagagg tagagcatgc ggtgcttggc ttggaagacg tgcaagacgc   13620
tgccgttatc gcatttgaca atgtggacag cgaagagcca gaaatggttg ggtttgtcac   13680
tattaccgaa gacaatcctg tccgtgagga cgaaaccagc ggtcaagtag aagactgggc   13740
gaaccacttc gagataagta cctacaccga tatcgcggcg atcgatcagg gtagcattgg   13800
aagtgacttt gtaggttgga cttctatgta cgacggaagc gagatcgaca aggcagagat   13860
gcaagaatgg cttgccgata ccatggcctc tatgctcgac gggcaggcgc cggcaatgt    13920
gttagagata ggtacaggca ctggcatggt cctcttcaat ctcggcgacg gactgcagag   13980
ctatgtcggc ctcgaaccat caagatcggc ggccgctttt gtcaaccaga cgattaagtc   14040
gctccccacc cttgctggca acgctgaagt acacattggc actgcgaccg acgtggcccg   14100
tctagatggc ctccgcccg acttagtggt agtcaattcg gtagtccagt acttcccatc    14160
accagagtac ctaatggaag tcgtggaggc tcttgcacgt ctgccgggcg tcgagcgaat   14220
tttcttcgga gacgtacgtt cgtacgccat caacagagat ttcctggctg ccagagctct   14280
acacgaactt ggcgacagag cgactaagca cgagattcgg cgaaagatgc tagagatgga   14340
agaacgcgaa gaggagctgc tcgtcgaccc agctttcttc accatgttga ccagcagtct   14400
ccctggcctg attcagcatg tcgagatctt gccgaagctg atgagagcca ctaatgagct   14460
cagcgcgtat cgatacactg ctgtagtaca cgtgtgccgt gccggtcaag agcctcgttc   14520
cgtgcatacg atcgacacg atgcctgggg gaatcttgga gcttctcggt tgagtcgccc    14580
tacccttca agcttttgc aaacttccga gggcgcatcg gccgtcgcag taagcaatat     14640
tccttacagc aagaccatca cagagcgagc gctcgttagt gcgctcgatg aggatgatat   14700
gcaagactca tcggactggc tgctggccgt gcgcgagaca ggcagatctt gttcctcctt   14760
ctccgcaaca gaccttgtcg agcttgctcg agagacgggc tggcgtgtgg agctcagctg   14820
ggcacgacag tactcacaga aaggcgcact cgatgctgtc ttccacagac accctgtttc   14880
cgctgggagc gggcgtgtca tgttccagtt tccagttgag accgaagatc gaccgcacat   14940
ctcacgcacg aaccgacctt tacagcgatt gcagaagaag cgaaccgaga cacatgttca   15000
tgagcagttg cgggctttgc ttccacgata catggttcct acgcggattg tggcgcttga   15060
taagctgccc gtcaatgcaa acggcaaggt tgatcgtcaa cagctcgcta ggacagccca   15120
ggttctccca gcgagcaagg cgccgtctgc atgcgtggcc ccacgcaacg aattggaaat   15180
gacactgtgt gaagagttct cgcaggttct tggcgtccag gtcggcatta ctgacaattt   15240
cttccacctg ggtggccact ctctcatggc aacaaagctt gccgctcgta tcagccaccg   15300
ccttcataca cgcatatccg tcaaacacat cttcgatcac cctttgatag gcgatttgtc   15360
tgtccacata gctgactctc cggtgcctct tttgacaatc acacgtgccc agcacgctgg   15420
agcagtggag cagtcattcg cacaagctag attgtgctgc cttgtccagc taggacttga   15480
atctccttcg tacatcatac caattgtatt gcgtttacac ggttcactct caaagactga   15540
cattgaagga gctctatcag ccctgatgga acgtcatgag gtccttcgta cgacgttcga   15600
ggaccataag ggtatcggca tgcaagtggt acaagaccat cgtcaccaag acttggttgt   15660
aattgacgtt gcaggtcagg ggtcactcga ctacaagcag cacttataca tggagcacgt   15720
gaaaccttc gatctgaccc gggatcctg gtggagggta gcgctgctgc gtctgggaga     15780
tgacgaccac gtcctctcca tcgtaatgca tcacatcatc tccgatggct ggtcgattga   15840
tatcctgctg cgtgagttgg gtcagttcta ctcggccgcg ctccggggc aggacccgtt    15900
gtcacagaca agtcctctgc cgatccagta tcgtgacttc gctctctgg aaaagcagga    15960
tcatcaatta gccgatcacg agaagcagct gcggtattgg gaagagcaac tggcggagag   16020
ctctccagct gagctgctat gtgatcatgc acgtccgacg acgccctcag gtcaggcagg   16080
ctcgattccc gtcaatgttc aaggctctct gtatcaggcg cttcgggcgt tctgccgcgc   16140
tcaccagctc acctctttcg tagtcctgct cacggcgttc cgcatagcac actatcgtct   16200
gacgggtgcg gaggacgcaa ccattggaac tcccattgca aatcgcaacc ggccagagct   16260
cgagaacatg atcggtttct tcgtcaatac acaatgcatg cgcatcgtca ttggcagtga   16320
cgacacattt gaagggctgg tgcagcaagt acgctcgata actgcagctg cccacgagaa   16380
ccaggacgtt ccattcgagc gcatcgtgtc agcactgctt cccggttcta gagacacatc   16440
acgcaatcct ctggtgcagt tgttgttcgc tgttcatgcc tatcaagagg tcgaaaattt   16500
cgccatcccc ggtgtgcact ccgagttggt gcaaggaacg acctttacaa gatttgatgt   16560
cgagttccac ctgcttgaag accctgacaa gctcagcggc aacgtgctct tcgcgaccga   16620
gctcttcgag cagaagacta tgcaaggcat ggtcgacgtg ttccaggaag tgctcagccg   16680
gggccttgag cagccccaga tacctctggc gaccctcccg ctcacgcacg gactggagga   16740
gctcaggacc atgggtcttc tcgacgtgga gaagacagac tacccctcgag agtcgagcgt   16800
ggtgacgtg ttccgtgagc aagcggctgc ctgctccgag gcgattgcgg tcaaagactc    16860
gtcggcgcag ctcacctact cggagctcga tcgacagtcg gacgagcttg ccggctggct   16920
gcgccagcaa cgtcttcctg cggagtcgtt ggttgcagtg ctggcaccca ggtcgtgcca   16980
gaccattgtc gcgttcctgg gcatcctcaa ggcgaatctg gcataccgc cgctagacgt    17040
caacgtgccc gctactcgcc tcgagtcgat actgtctgcc gtcggcggcc ggaagctggt   17100
cttgcttgga gctgacgtgg ccgaccctgg ccttcgcctg cgcgatgtgg agctcgtgcg   17160
gatcggcgac acactcggcc gctgtgtacc cggggcgccc ggcacaatg aggcacctgt    17220
ggtgcagcct tctgccacaa gccttgccta cgtcatcttc acttccgtct cgaccggcaa   17280
gccgaagggt gtcatggtcg agcaccgcag tatactcagg gttgtcacgt ctcccccggc   17340
ccgtgctctg ctaccgtcca caatcatcat ggcccacctg acaaacattg cattcgatgt   17400
atcgctatgg gagatatgta cagctcttct tcacggtggt accctgatct gtattcagta   17460
tcttgcctcg ctcgatgtca gggggcttca gactacattc tctcgcgaag ctatcaacgt   17520
agctgtgttt cctcctgcct tgctaaagac tcgtcttgcc aagattccat ctgctctagc   17580
atcgctgagt gccatgttct cgtccggaga tcgtctcgac tcacgcgatg ctagcgaggg   17640
ggccacactt gtgcggcaag ggatacacaa cgcgtatggt cccacggaga atggcatcca   17700
gagcacaatc tatgaagtca aagcggacgc tgagtttgtc aatggtgtgc ctatcggccg   17760
cgctgtgagc aactcagggg catatgtcat ggacccgcag cagcaactgg tgcctctcgg   17820
ggtgatgggc gagctcgtcg tcaccggcga cggcctggcc cgtggttaca ccgacccgtc   17880
```

```
actggatgcg gaccgctttg tgcaggtctc cgtcaacggg cagctcgtga gagcgtaccg   17940
aacaggcgat cgcgtgcgct gcaggccttg cgatggccag atcgagttct ttggacgtat   18000
ggaccggcaa gtcaagatcc gaggacatcg catcgagctc gcagaggtag agcatgcgat   18060
attgtcccct gattatgtga tcgatgcagc cgtccttctg agacagctga ttgatcaaga   18120
gccacaagtg gtaggattcg tcattgtatc caccaaacgg gcttattccc gacacaacag   18180
cggctacgcg tctgaagttt cggcattctg catcaaagat cagatcgcat ggcgcattct   18240
acaacatctc tgcaggatgc tgccttccta tatggttccc tatcaaattg caattcttga   18300
tgaaatgcct atcaatgcta acggcaaggt ggatagacag aatcttgcaa gcagaactgt   18360
caacgtccaa agaatcctcg ccgctccata catggcccg cgcaatgaag tcgagatttc   18420
gctttgcgaa cagtatgctg ccctgcttga acacgacgtt ggcattcttg acgacttctt   18480
cgaacttggt ggtcactctc tcatggctac tagactggcc tcgcgtatca gctcccgatt   18540
cagcgctccg gtgtctgttc gtgatatttt cgaccatcca agaatcatgg accttgctag   18600
catcattcgt gctggagaca ttcaatggtc ccggatactg ccttctgctt atgaacgtcc   18660
agtcgagcaa tctttcgcac agaatcgcct gtggttcgtc tacaagcttg acataggtac   18720
gacacagtat aatttaccgc tggcgataca ccttcgagga ccactagata tatcagcgct   18780
gtttatcgca ttcaaggcat tgactgaaag acatgaactt ttgcgcacaa cttttgatga   18840
ggatgacgga acatgcctgc agatgttatt gcctgaatat cagcatgaag taaggatcac   18900
cgacttgcag ggatcacaca aaggtagcct cctggatatt ctcaacaaca atcagaagac   18960
tcccttcgag ctgagccgcg agcctggatg gagggtagcg ctgctgcgtc tgggagatga   19020
cgaccacgtc ctctccatcg tcatgcatca catcatctcc gacggttggt ctgtggacgt   19080
gctgcgccac gagctaggtc agttctactc ggccgcgctc cggggcagg acccgttgtc   19140
gcagataagt cctctgccga tccagtatcg tgacttcgct ctctggcaga gacaagacga   19200
gcaagttgcg gagcatcagc gccagctgga gcattggaca gagcagttgg cagacagttc   19260
acccgccgag ttgttgagcg accacccgag gccatcgatt cttctgtgcc aggcgggcgc   19320
tattcccgtc aatgttcaag gctctctgta tcaggcgctt cgggcgttct gccgcgctca   19380
ccaggtcacc tctttcgtag tcctgctcac ggcgttccgc atagcacact atcgtcgac   19440
gggtgcggaa gacgcaacca ttggaactcc cattgcaaat cgcaaccggc cagagctcga   19500
gaacatgatc ggtttcttcg tcaatacaca atgcatgcgc atcgtcattg gcagtcgacga   19560
cacatttgaa gggctggtgc agcaagtacg ctcgataact gcagctgccc acgagaacca   19620
ggacgttcca ttcgagcgca tcgtgtcagc actgcttccc ggttctagag acacatcacg   19680
caatcctctg gttcagctca tgtttgctgt ccactcgcaa agaaaccttg gtcagatcag   19740
tctagaaggc ctgcagggtg aattgctggg agtggcagcg actacgagat tcgatgtaga   19800
gttccatctc ttccaagatg acgacaagct cagcggcaac gtgctcttcg cgaccgagct   19860
cttcgagcag aagactatgc aaggcatggt cgacgtgttc caggaagtgc tcagccgggg   19920
ccttgagcag ccccagatac ctctggcgac cctcccgctc acgcacggac tggaggagct   19980
caggaccatg ggtcttctcg acgtggagaa gacagactac cctcgagagt cgagcgtggt   20040
ggacgtgttc cgtgagcaag cggctgcctg ctccgaggcg attgcggtca aagactcgtc   20100
ggcgcagctc acctactcgg agctcgatcg acagtcggac gagcttgccg gctggctgcg   20160
ccagcaacgt cttcctgcgg agtcgttggt tgcagtcgcg gacaccaggt cgtgccagac   20220
cattgtcgcg ttcctgggca tcctcaaggc gaatctggca tacctgccgc tagacgtcaa   20280
cgtgcccgct actcgcctcg agtcgatact gtctgccgtc ggcggccgga agctggtctt   20340
gcttggagct gacgtggccg accctggcct tcgcctggcg gatgtggagc tcgtgcggat   20400
cggcgacaca ctcggccgct gtgtaccgg ggcgcccggc gcaacgagg cacctgtggt   20460
gcagccttct gccacaagcc ttgcctacgt catcttcact tccggctcga ccggcaagcc   20520
gaagggtgtc atggtcgagc accggggtgt agtgcgactt gtcaagcaga gcaatgttgt   20580
ctaccatctc ccgtccacat ctcgcgtggc ccacctgtcg aatctcgcct tgatgcctc   20640
ggtcctcgag atctatgcgg cccttctgaa cggtggtact gtttactgca ttgactatct   20700
cactacccctt gaccctcacg cgcttgagtc tgttttcatc gatgctgatc tcaacacggc   20760
agtccttcct cccgctctac ttaaacaggg ccttgcttcg agcccttcta ccctccatgc   20820
ccttgattta ctccttcatag gaggagatcg attggatgct cgtgacgccc tgtacgctaa   20880
tcgtctggtt cgagggtcat tatacaatgt ctatggcccg acagagaaca ccgttctgag   20940
cgtcgtttac ctctttaatg atgacgatgc atgcattaat ggcgtcccta tcggccaagt   21000
cgtcagtaat tccgggtgtat acgtcatgga ctcagaacag aaattagtac ctcctggggt   21060
catgggagaa atcgtcgtga caggagacg tctcgcaaga gggtatactg actcaaccct   21120
aaatactgat cgtttcgttc aaatcagtgt caacggacgt gtactgcaag cataccgtac   21180
aggcgatcgt ggtcggtacc gcccgacaga cgctcgtctt gagttctttg gccgtctaga   21240
tcaacaaatc aagcttcgcg ggcatcgtgt agagctcaaa gaaatcgagc aagcgatgct   21300
tggccacaat gctgttgatg atgcaggagt tgtcgtctg gagatatctg agtgccaaga   21360
gctagagatg gttggctttg tgactctacg caatcttgga accatggaag caactaacaa   21420
tctcgcacac acaagctgga acccagtga tctcaaaacc cctttagcat cacaaatagt   21480
ggctgaggtt cggggtagac tccagcgaaa tctgccactc tatatggtac ccgctacgat   21540
tgtggtatta catactatgc cagtcaatgc caacgggaag ctcgaccgac aagcacttgt   21600
gaaagctgca atgacgcttc caaaaactgc tccactggta tggatggctc cgcgcaatga   21660
aggagagaca tcgctatgtg aggagcaac agatatcttg ggggtgaacg tcgggatcac   21720
cgataacttt tttgaccttg gggggcattc cctcctggca accagagtag ccgcgcgaat   21780
cagccgacgt cttgatgccc tggtgaccgt caaacaaata ttcgaccatc cagtcattgg   21840
agatctcgca gctgcaattc aagggggttc agtacggcat ttaccaataa ctgcaagcga   21900
ggtcgatgga cctgttcagc agtccttcgc gcaaaatcgc ttgtggttcc tagacagat   21960
gaatattgga gtacttggt acatcgtacc gttagcagtg cgtctgtacg gcacactgca   22020
agttgaggct ctgaatattg cgttgcgtac gattcagcaa cgccacgaaa cattacgaac   22080
gaccttcgaa gaactaaatg ggattgccgt tcaacgttgt gattcaacct gccaaggcca   22140
attaaggggtg gtagatttag tcgggcaggg gccagatcgc tatagagaga ttctggatgt   22200
ccagcaaact acacccattcg agctgagcca ggagcctgga tggagggtag cgctgcttcg   22260
tctgggagat gacgaccacg tcctctccat cgtcatgcat cacatcatct ccgacggttg   22320
gtctgtggac gtgctgctac gtgagatagg tcagttctac tcggccgcgc tccggggca   22380
ggacccgttg tcgcagataa gtcctctgcc gatccagtat cgtgacttcg ctctctggca   22440
gagacaagac gagcaagttg cggagcatca gcgccagctg gagcattgga cagagcagtt   22500
ggcagacagt tcacccgccg agttgttgag cgaccacccg aggccatcga ttctttctgg   22560
ccaggcgggc gctattcccg tcaatgttca aggctctctg tatcaggcgc ttcgggcgtt   22620
```

```
ctgccgcgct caccaggtca cctctttcgt agtcctgctc acggcgttcc gcatagcaca  22680
ctatcgtctg acgggtgcgg aggacgcaac cattggaact cccattgcaa atcgcaaccg  22740
gccagagctc gagaacatga tcggtttctt cgtcaataca caatgcatgc gcatcgtcat  22800
tggcagtgac gacacatttg aagggctggt gcagcaagta cgctcgataa ctgcagctgc  22860
ccacgagaac caggacgttc cattcgagcg catcgtgtca gcactgcttc ccggttctag  22920
agacacatca cgcaatcctc tggttcagct catgtttgct gtccactcgc aaagaaacct  22980
tggtcagatc agtctagaag gcctgcaggg tgaattgctg ggagtggcag cgactacgag  23040
attcgatgta gagttccatc tcttccaaga tgacgacaag ctcagcggca acgtgctctt  23100
cgcgaccgag ctcttcgagc agaagactat gcaaggcatg gtcgacgtgt tccaggaagt  23160
gctcagccgg ggccttgagc agccccagat acctctgccg accctcccgc tcacgcacgg  23220
actgaggag ctcaggacca tgggtcttct cgacgtggag aagacagact accctcgaga  23280
gtcgagcgtg gtggacgtgt tccgtgagca agccggctgcc tgctccgagg cgattgcggt  23340
caaagactcg tcggcgcagc tcacctactc ggagctcgat cgacagtcgg acgagcttgc  23400
cggctggctg cgccagcaac gtcttcctgc ggagtcgttg gttgcagtgc tggcacccag  23460
gtcgtgccag accattgtcg cgttcctggg catcctcaag gcgaatctgg catacctgcc  23520
gctagacgtc aacgtgcccg ctactcgcct cgagtcgata ctgtctgccg tcggcggccg  23580
gaagctggtc ttgcttggag ctgacgtggc cgaccctggc cttcgcctgg cggatgtgga  23640
gctcgtgcgg atcggcgaca cactcggccg ctgtgtaccc ggggcgcccg gcgacaacga  23700
ggcacctgtg gtgcagcctt ctgccacaag ccttgcctac gtcatcttca cttccgctc   23760
gaccggcaag ccgaagggtg tcatggtcga gcaccgggt gtagtgcgac ttgtcaagca  23820
gagcaatgtt gtctaccatc tcccgtccac atctcgcgtg gcccacctgt cgaatctcgc  23880
ctttgatgcc tcggcgtggg agatctatgc ggcactgctt aatggcggta cactcatctg  23940
cattgactat ttcacaactc tagactgctc tgctctcggc gccaaattca tcaaggagaa  24000
gatcgtcgcg accatgattc cgccagcgct tctgaagcaa tgtctggcga tcttcccgac  24060
cgctcttagt gaactggtcc tgctgtttgc tgccggagat cgattcagca gtggcgatgc  24120
cgtcgaagtg cagcgccaca ccaaaggcgc tgtttgtaac gcgtacggac cgacagaaaa  24180
caccattctt agtacgatct acgaagtcaa gcagaatgga aacttcccga acggtgtgcc  24240
tatcggccgc gctgtgagca actcaggggc atatgtcatg gacccgcagc agcaactggt  24300
gcctctcggg gtgatgggcg agtcgtcgt caccggcgac ggcctggccc gtggttacac  24360
cgaccgtca ctggatgcgg accgctttgt gcaggtctcc gtcaacggac agctcgtgag  24420
agcgtaccga acaggcgatc gcgtgcgctg caggccttgc gatggccaga tcgagttctt  24480
tggacgtatg gaccggcaag tcaagatccg aggacatcgc atcgagctcg cagaggtaga  24540
gcatgcggtc cttggcttgg aagacgtgca agacgctgcc gttatcgcat ttgacaatgt  24600
ggacagcgaa gagccagaaa tggttgggt tgtcactatt accgaagaca atcctgtccg  24660
tgaggacgaa accagcggtc aagtagaaga ctgggcgaac cacttcgaga taagtaccta  24720
caccgatatc gcggcgatcg atcagggtag cattggaagt gactttgtag gttggacttc  24780
tatgtacgac ggaagcgaga tcgacaaggc agagatgcaa gaatggcttg ccgataccat  24840
ggcctctatg ctcgacgggc aggcgccggg caatgtgtta gagataggta caggcactgg  24900
catggtcctc ttcaatctcg gcgacgact gcagagctat gtcggcctcg aaccatcaag  24960
atcggcggcc gcttttgtca accagacgat taagtcgctc cccacccttg ctggcaacgc  25020
tgaagtacac attggcactg cgaccgacgt ggccgtcta gatggcctcc gccccgactt  25080
agtggtagtc aattcggtag tccagtactt cccatcacca gagtacctaa tggaagtcgt  25140
ggaggctctt gcacgtctgc cgggcgtcga gcgaattttc ttcggagacg tacgttcgta  25200
cgccatcaac agagatttcc tggctgccag agctctacac gaacttggcg acagagcgac  25260
taagcacgag attcggcgaa agatgctaga gatggaagaa cgcgaagagg agctgctcgt  25320
cgacccagct ttcttcacca tgttgaccag cagtctccct ggcctgattc agcatgtcga  25380
gatcttgccg aagctgatga gagccactaa tgagctcagc gctatcgat acactgctgt  25440
agtacacgtg tgccgtgccg gtcaagagcc tcgttccgtg catacgatcg acgacgatgc  25500
ctgggtgaat cttggagctt ctcggttgag tcgccctacc cttcaagcc ttttgcaaac  25560
ttccgagggc gcatcggccg tcgcagtaag caatattcct tacagcaaga ccatcacaga  25620
gcgagcgctc gttagtcgc tcgatgagga tgatatgcaa gactcatcg actgctgct   25680
ggccgtgcgc gagacaggca gatcttgttc ctccttctcc gcaacagacc ttgtcgagct  25740
tgctcgagag acgggctggc gtgtggagct cagctgggca cgacagtact cacagaaagg  25800
cgcactcgat gctgtcttcc acagacaccc tgtttccgct gggagcgggc gtgtcatgtt  25860
ccagttttcca gttgagaccg aagatcgacc gcacatctca cgcacgaacc gaccttaca   25920
gcgattgcag aagaagcgaa ccgagacaca tgttcatgag cagttgcggg ctttgcttcc  25980
acgatacatg gttcctacgc ggattgtggc gcttgataag ctgcccgtca atgcaaacgg  26040
caaggttgat cgtcaacagc tcgctaggac agcccaggtt ctcccagcga gcaaggcgcc  26100
gtctgcatgc gtggcccac gcaacgaatt ggaaatgaca ctgtgtgaag agttctcgca  26160
ggttcttggc gtcgaggtcg gcattactga caatttcttc cacctgggtg gccactctct  26220
catggcaaca aagttcgccg ctcgtatcag ccgccggctg aatgctatcg tttcggtcaa  26280
gaatgtcttc gaccaccccg tacctatgga tcttgcagcg acaatccaag aaggctcaaa  26340
gcttcatact ccaatccctc gcacggctta cagcggtcct gtcgaacagt ctttcgcaca  26400
aggacgtctt tggttccttg accaattcaa tcctagctcg attgggtatg tgatgccttt  26460
cgctgcgcgt cttcatggtc aactacaaat cgaagcgctc acagcagcat tgttcgcttt  26520
ggaacagcga catgagatcc tgcgaacaac gttggacgca cacgatggtg taggcatgca  26580
gatcgttcac gcggaacatc cgcaacagtt gagaatcatt gatgtgtcag caaaggcgtc  26640
gagcagttat gctcagacac tgcgtgacga gcaggcgtca cctttcgacg taagcaagga  26700
accaggttgg agagtcgt tgctgcagct cagtgagata gattatgttc tttccattgt   26760
aatgcatcac accatctatg acggttggtc tctcgacgta ctccggcggg agctaagtca  26820
gttttatgcc gctgccatcc gtggtcgaga acctctatcg acaatcgagc cattgcctat  26880
ccaataccgc gacttttctg tctggcaaaa gcaggaagac caagtcgcag agcatcgacg  26940
acagctccat tattggatag agcagctaga tggcagctct cctgctgagt tcctaaacga  27000
taaaccacgg cctacgttgc tttctgcgcaa gcgaggagt tggaaattg ctgtgaaggg   27060
cactgtatat caacgtctgc tagagttctg caggcttcat caggtcacct cgttcatggg  27120
gctgcttgcg gcattccgag cgacacacta tcgtctgaca ggcacagagg acgcgactgt  27180
cggaacaccc atcgccaatc gcaatcgacc tgagctggaa acatgattg gattgttcgt   27240
gaatactcag tgtatacgcc tcaagatcga ggacaatgat actctcgagg agctagtaca  27300
gcacgttcgt gccacgatca cagcatcaat ctcgaaccag gatgtacctt ttgaacaggt  27360
```

```
agtgtctgca ttgctaccag gatcacgcga cacctctagg aacccactag ttcagctgac   27420
ttttgcggtg cattctcagc gaaatttggc tgacattcag ctagaaaacg tggagaccaa   27480
tgctatgcca atttgcccct cgacacgttt cgacgctgaa ttccacctct tccaagagga   27540
gaatatgcta agcggaaggg tgctgttttc agacgatctt ttcgagcaga agactatgca   27600
aggcatggtc gacgtgttcc aggaagtgct cagccgggggc cttgagcagc cccagatacc   27660
tctggcgacc ctcccgctca cgcacggact ggaggagctc aggaccatgg gtcttctcga   27720
cgtgagaag acagactacc ctcgagagtc gagcgtggtg gacgtgttcc gtgagcaagc   27780
ggctgcctgc tccgaggcga ttgcggtcaa agactcgtcg gcgcagctca cctactcgga   27840
gctcgatcga cagtcggacg agcttgccgg ctggctgcgc cagcaacgtc ttcctgcgga   27900
gtcgttggtt gcagtgctgg cacccaggtc gtgccagacc attgtcgcgt tcctgggcat   27960
cctcaaggcg aatctggcat acctgccgct agacgtcaac gtgcccgcta ctcgcctcga   28020
gtcgatactg tctgccgtcg gcggccgaaa gctggtcttg cttggagctg acgtggccga   28080
ccctggcctt cgcctggcgg atgtggagct cgtgcggatc ggcgacacac tcggccgctg   28140
tgtacccggg gcgcccggcg acaacgaggc acctgtggtg cagccttctg ccacaagcct   28200
tgcctacgtc atcttcactt ccggctcgac cggcaagccg aagggtgtca tggtcgagca   28260
ccggggtgta gtgcgacttg tcaagcagag caatgttgtc taccatctcc cgtccacatc   28320
tcgcgtggcc cacctgtcga atctcgcctt tgatgcctcg gcgtgggaga tctatgcggc   28380
actgcttaat ggcggtacac tcatctgcat tgactatttc accatcatag acgctcgcgc   28440
acttggcgtt atctttgcgc aacaaagtat caacgcaacc atgctgtcac ctctactcct   28500
caaacaattt ttgtcagatg caccattcgt gctgcgatct ctgcatgccc tttatctagg   28560
gggggacaga cttcagggtc gtgacgcaat ccaggcttgt cgtgtaggtt gcgcatttgt   28620
catcaatgcc tatgcccaa cagagaattc tgtcatcagt actacttaca cacttgtgaa   28680
gggaaatgcg gacttcccga acggtgtgcc tatcggccgc gctgtgagca actcaggggc   28740
atatgtcatg gacccgcagc agcaactggt gcctctcggg gtgatgggcg agctcgtcgt   28800
caccggcgac ggcctggccc gtggttacac cgacccgtca ctggatgcgg accgctttgt   28860
gcaggtctcc gtcaacgggc agctcgtgag agcgtaccga acaggcgatc gcgtgcgctg   28920
caggccttgc gatggccaga tcgagttctt tggacgtatg gaccggcaag tcaagatccg   28980
aggacatcgc atcgagctcg cagaggtaga gcatgcggtg cttggcttgg aagacgtgca   29040
agacgctgcc gttctcatag ctcaaacagc cgaaaatgaa gagctagttg gcttcttcac   29100
gcttcgacaa acccaggctg tgcagtcaaa tggtgccgct ggtgttgtgc cagagcacag   29160
cgactccgag ctggcgcaat cctgctcttg cactcaaacg gagcgtcgag tccgcaacag   29220
attgcaatcc tgtcttcctc gctacatggt tccgtcgcga atggtccttt tggatcgact   29280
gcctgtcaac cccaatggta agttgatcg acaagagctc acgaggcgcg ctcaggatct   29340
cccaataagc gagtcatccc cagtgcacgt caaaccgcgt actgaactgg aaaggtcgca   29400
gtgcgaggag ttcgccgatg ttataggttt ggaagtcggc gttaccgata atttcttcga   29460
cctaggcggg cactctctca tggcgatgaa actcgcagct cgcatcagcc gtcgttcgaa   29520
tgcacatata tcagtcaagg acattttcga ccacccgctg attgcagatc tcgcaatgaa   29580
aattcgggaa ggctccgatc tgcacactcc aattccccac aggatgtacg ttggacctat   29640
ccagctatca ttcgcacagg gacgcttgtg gttcctcgac caattgaatt tgggcgcaat   29700
gtggtacgtc atgccacttg ctatgcgcct ccaaggctcg ctccagctcg acgcgttaga   29760
gactgcactg tttgctatcg agcagcgaca cgaaaaccttta cggatgacat ttgcagaaca   29820
agacggagta gctgtacaag tagtgcatgc agcccctac aaaacacatca agatgatcga   29880
caaaccactt agacagaaga ttgacgtcct gaagatgctg gagaagaac ggacgactcc   29940
cttcgagctg agccgcgagc ctggatggag ggtagccctg ctgcgtctgg gagatgacga   30000
ccacgtcctc tccatcgtca tgcatcacat catctccgac ggtggtctg tggacgtgct   30060
gcgccacgag ctaggtcagt tctactcggc cgcgctccgg gggcaggacc cgttgtcgca   30120
gataagtcct ctgccgatcc agtatcgtga ctttcgctct tggcagagac aagacgagca   30180
agttgcggag catcagcgcc agctggagca ttggacagag cagttggcag acagttcacc   30240
cgccgagttg ttgagcgacc acccgaggcc atcgattctt tctggccagg cgggcgctat   30300
tcccgtcaat gttcaaggct ctctgtatca ggcgcttcgg gcgttctgcc gcgctcacca   30360
ggtcacctct ttcgtagtcc tgctcacggc gttccgcata cacacactc gtctgacggg   30420
tgcggaggac gcaaccattg gaactcccat tgcaaatcgc aaccggccag agctcgagaa   30480
catgatcggt ttcttcgtca atacacaatg catgcgcatc gtcattggca gtgacgacac   30540
atttgaaggg ctggtgcagc aagtacgctc gataactgca gctgcccacg agaaccagga   30600
cgttccattc gagcgcatcg tgtcagcact gcttcccgt tctagagaca catcacgcaa   30660
tcctctggtt cagctcatgt ttgctgtcca ctcgcaaaga aaccttggtc agatcagtct   30720
agaaggcctg cagggtgaat tgctgggagt ggcagcgact acgagattcg atgtagagtt   30780
ccatctcttc caagatgacg acaagctcag cggcaacgtg ctcttcgcga ccgagctctt   30840
cgagcagaag actatgcaag gcatggtcga cgtgttccga gaagtgctca gccgggggcct   30900
tgagcagccc cagatacctc tggcgaccct cccgctcacg cacggactgg aggagctcag   30960
gaccatgggt cttctcgacg tggagaagac agactaccct cgagagtcga gcgtggtgga   31020
cgtgttccgt gagcaagcgg ctgcctgctc cgaggcgatt gcggtcaaag actcgtcggc   31080
gcagctcacc tactcggagc tcgatcgaca gtcggacgag cttgccggct ggctgcgcca   31140
gcaacgtctt cctgcggagt cgttggttgc agtgctggca cccaggtcgt gccagaccat   31200
tgtcgcgttc ctgggcatcc tcaaggcgaa tctggcatac ctgccgctag acgtcaacgt   31260
gcccgctact cgcctcgagt cgatactgtc tgccgtcggc ggccgaaagc tggtcttgct   31320
tggagctgac gtggccgacc ctggccttcg cctggcggat gtggagctcg tgcggatcgg   31380
cgacacactc ggccgctgtg tacccggggc gcccggcgac aacgaggcac ctgtggtgca   31440
gccttctgcc acaagccttg cctacgtcat cttcacttcc ggctcgaccg gcaagccgaa   31500
gggtgtcatg gtcgagcacc ggggtgtagt gcgacttgtc aagcagagca atgttgtcta   31560
ccatctcccg tccacatctc gcgtggccca cctgtcgaat ctcgcctttg atgcctcggc   31620
gtgggagatc tatgcggcac tgcttaatgg cggtacactc atctgcattg actatttcac   31680
aactctagac tgctctgctc tcggcgccaa attcatcaag gagaagatcg tcgcgaccat   31740
gattccgcca gcgcttctga gcaatgtctc ggcgatctct ttagtgaact   31800
ggtcctgctg tttgctgccg gagatcgatt cagcagtggc gatgccgtcg aagtgcagcg   31860
ccacaccaaa ggcgctgttt gtaacgcgta cggaccgaca gaaaacacca ttcttagtac   31920
gatctacgaa gtcaagcaga atgagaactt cccgaacggt gtgcctatcg gccgcgctgt   31980
gagcaactca ggggcatatg tcatggaccc gcagcagcaa ctggtgcctc tcggggtgat   32040
gggcgagctc gtcgtcaccg gcgacggcct ggcccgtggt tacaccgacc cgtcactgga   32100
```

```
tgcggaccgc tttgtgcagg tctccgtcaa cgggcagctc gtgagagcgt accgaacagg   32160
cgatcgcgtg cgctgcaggc cttgcgatgc ccagatcgag ttctttggac gtatggaccg   32220
gcaagtcaag atccgaggac atcgcatcga gctcgcagag gtagagcatg cggtgcttgg   32280
cttggaagac gtgcaagacg ctgccgttat cgcatttgac aatgtggaca gcgaagagcc   32340
agaaatggtt gggtttgtca ctattaccga agacaatcct gtccgtgagg acgaaaccag   32400
cggtcaagta gaagactggg cgaaccactt cgagataagt acctacaccg atatcgcggc   32460
gatcgatcag ggtagcattg gaagtgactt tgtaggttgg acttctatgt acgacggaag   32520
cgagatcgac aaggcagaga tgcaagaatg gcttgccgat accatggcct ctatgctcga   32580
cgggcaggcg ccgggcaatg tgtttagagat aggtacaggc actggctggt tcctcttcaa   32640
tctcggcgac ggactgcaga gctatgtcgg cctcgaacca tcaagatcgg cggccgcttt   32700
tgtcaaccag acgattaagt cgctccccac ccttgctggc aacgctgaag tacacattgg   32760
cactgcgacc gacgtggccc gtctagatgg cctccgcccc gacttagtgg tagtcaattc   32820
ggtagtccag tacttcccat caccagagta cctaatggaa gtcgtggagg ctcttgcacg   32880
tctgccgggc gtcgagcgaa ttttcttcgg agacgtacgt tcgtacgcca tcaacagaga   32940
tttcctggct gccagagctc tacacgaact tggcgacaga gcgactaagc acgagattcg   33000
gcgaaagatg ctagagatgg aagaacgcga gaggagctg ctcgtcgacc cagctttctt   33060
caccatgttg accagcagtc tccctggcct gattcagcat gtcgagatct tgccgaagct   33120
gatgagagcc actaatgagc tcagcgcgta tcgatacact gctgtagtac acgtgtgccg   33180
tgccggtcaa gagcctcgtt ccgtgcatac gatcgacgac gatgcctggg tgaatcttgg   33240
agcttctcgg ttgagtcgcc ctacccttc aagccttttg caaacttccg agggcgcatc   33300
ggccgtcgca gtaagcaata ttccttacag caagaccatc acagagcgag cgctcgttag   33360
tgcgctcgat gaggatgata tgcaagactc atcgtgctgg cgcgagac   33420
aggcagatct tgttcctcct tctccgcaac agacccttgtc gagcttgctc gagagacggg   33480
ctggcgtgtg gagctcagct gggcacgaca gtactcacag aaaggcgcac tcgatgctgt   33540
cttccacaga caccctgttt ccgctgggag cgggcgtgtc atgttccagt tccagttga   33600
gaccgaagat cgaccgcaca tctcacgcac gaaccgacct ttacagcgat tgcagaagaa   33660
gcgaaccgag acacatgttc atgagcagtt gcgggctttg cttccacgat acatggttcc   33720
tacgcggatt gtggcgcttg ataagctgcc cgtcaatgca aacggcaagg ttgatcgtca   33780
acagctcgct aggacagccc aggttctccc agcgagcaag gcgccgtctg catgcgtggc   33840
cccacgcaac gaattggaaa tgacactgtg tgaagagttc tcgcaggttc ttggcgtcga   33900
ggtcggcatt actgacaatt tcttccaccct gggtggccac tctctcatgg caacaaagct   33960
tgccgctcgt atcagccgtc aactaaatat ccaagtctca gtccgagaca tctttgacta   34020
tcccgttata gtcgacctca cagacagatt gagactccat catacgcgta tccttactca   34080
tgatcatgga caactggac agccagacct caagccattc accttgctac caaccaacaa   34140
tcctcaagaa ttcctacagc atcacatttt gccacaactt gttcccgatc atgcgaagat   34200
cctcgatgtg tatcccgtta caagaataca gagaaggttt cttcatcatc cgaagcgcgg   34260
cctccctcgt tttccctcca tggtcttctt tgacttccct cctggttcag acccacacaa   34320
gctaagatta gcttgtatgg cattagtcca gcgttcgac attcttcgca caatcttcct   34380
ttctgttttcg ggtcaattct tccaagtggt cctggatgga tatggattg tcataccggt   34440
catcgaggtt gacgaagagc tagacgacgc caccccgtaaa ttacacgatt ccgatattca   34500
gcagcccttta cggttgggaa aaccgttaat acgcattgct gtcttgaaa ggcagcactc   34560
cagagtacga gcagtcttgc gcttgtcgca tgctctctat gatggtttga gctttgagca   34620
tatcatccaa tctcttcatg ccctttatct cgatatccact cttcggcacc tgctcggaagt   34680
tggactctac gtacaacata tgatacaaag tcgcgcagaa ggttatgctt tctggcggtc   34740
tgtcttgaag ggctcgtcga tgacaattct cgagcgttct agcacccttc aatcgcggca   34800
gccgcatctt ggacgttttc tctctgcgga gaaaattatt aaggctcctt tacacgccaa   34860
caagtctgga atcacacagg caacagtgtt cgccggccgca aacgcactca tgcttgcgaa   34920
tcttactggt actaatgacg ttgtgtttgc ccgcattgtc tctggacgtc aatctttgcc   34980
taagaacttt cagcacgttg tgggaccttg cacgaacgat gtgcccgttc gcgtacgcat   35040
ggagcctggc gtgggaccaa aagcttact cagacaggtg caagaccagt atgttcatag   35100
cttcccttc gaaacactag gattcgacga gatcaaggag aactgtacgg actgaccgaa   35160
aagaatcacg aattttgggt gttctacaac ttaccagaa tttgacattt ttcccaaaag   35220
tcagattgac caccagcaga ttcaaatggc tagcttggca agcgagtatc agaatcgaga   35280
aacctgggac gaagcgccgc tatacgacct caatgtcaca ggagtacctc agcctgacgg   35340
acgtcatatc aagatatacg tgggtgtaga cgggcagctt tcgcatgaaa gcacgcttga   35400
ttgcattctc tcggatattt gtgagggtgt ggtctcgctc acagacgctt gcaagaact   35460
tcccgctgct agcattactg agtagaatcc caagagagca acaccctatc atgatagcga   35520
cagcacgttt tcagttcgtc agagcttgac tgaaatgctt ttcgtctact acatctagcg   35580
tgtcatacca gctagtagct acaacggagc aacgattggc tgatgagcca ggacctgaaa   35640
agaagaagaa gatggaaata tagccttgga atctataata aag                     35683

SEQ ID NO: 6              moltype = AA  length = 11659
FEATURE                   Location/Qualifiers
source                    1..11659
                          mol_type = protein
                          note = Aureobasidium pullulans strain BP-1938
                          organism = unidentified
SEQUENCE: 6
MSRMPQGAAR RNDCVSEHQG TTDLEDIVRF WERHLDGVNA SAFPALSSSL VVPKPKLQTE   60
HRISLGTAVS DQWSDAVICR AALAVILARY THATEALYGI VVEQPSVSNA QKRSADDASS  120
IVVPIRVQCA SGQFGNDILA AIATHDASCR SLSAIGLDGI RCLDDAKTVA RGLQTVLTVT  180
SRKSVDASSP NILDLENIAS SHGRALMIEC QMSTTSACLR AQYDAGILRN EQVVRLLKQL  240
ALSIQHFRGN AANDLLRDFC FISPGEEMEI AYWNRRSIRT NEVCIHDVIF KRATYMPTDT  300
AVSAWDGEWT YADLDVVSSC LADYVRSLDL RSGQAIPLCF EKSRNTIAAM VAVLKAGHPF  360
CLIDPSTPSA RITQMCEQMS ATVAFASRAL CSIMQAGVSR CIAVDDDLFQ SLSSVIGCPQ  420
MSMTRPQDLA YVIFTSGSTG IPKGSMIEHR GFASCALEFG PQLLIDRNTR ALQFASHAFG  480
ACLLEVLVTL MLGGCVCVPS ENDRLNNLSG FIEQSGVNWT LFTPSFIGAL TPETIRGVHT  540
VVLGGEPMTP FIRDVWASKV QLLSIYGQSE SSTVCSVVKI KPDTTDLSSL GHAIGARFWI  600
VDAENPSRLA PIGCIGELMV ESPGIAREYL SAQEAQMSPF ITKTPAWYPM KQRCSPVKFY  660
```

```
MTGDLACYGR DGTVMNLGRK DSQVKIRGQR VELGDVETNL RSVLPKHIIP VVEAIDSIHA     720
SGSKFLVAIL IGANHGMKNE FDTEPRREVS ILDETAVIRI RKSMQDLVPS YCIPTQYICM     780
ERLLTTTTGK ADRKRLRAIC VDLLKPSRRA MVPESSDGPT LKLTAGQVLD EAWHRYLRFD     840
SVLDGSKSKF FDLNGDSITA IKIANAARKH GVMLKVADIL ANPTLADLRA QFQIDFTPQN     900
SILRTSYRGP IQQSFAQNRL WFLDQLNVGA SWYIVPVAVR LQGTVHVDAL VTALCALEQR     960
HETLRTTFEE SDGEGIQRIQ PSGLEQLRLI DVDCVDSRDY QRVLEEEQTT PFELSREPGW    1020
RVALLRLGDD DHVLSIVMHH IISDGWSVDV LRHELGQFYS AALRGQDPLS QISPLPIQYR    1080
DFALWQRQDE QVAEHQRQLE HWTEQLADSS PAELLSDHPR PSILSGQAGA IPVNVQGSLY    1140
QALRAFCRAH QVTSFVVLLT AFRIAHYRLT GAEDATIGTP IANRNRPELE NMIGFFVNTQ    1200
CMRIVIGSDD TFEGLVQQVR SITAAAHENQ DVPFERIVSA LLPGSRDTSR NPLVQLMFAV    1260
HSQRNLGQIS LEGLQGELLG VASPTRFDVE FHLFQEENML SGRVLFSDDL FEQKTMQGMV    1320
DVFQEVLSRG LEQPQIPLAT LPLTHGLEEL RTMGLLDVEK TDYPRESSVV DVFREQAAAC    1380
SEAIAVKDSS AQLTYSELDR QSDELAGWLR QQRLPAESLV AVLAPRSCQT IVAFLGILKA    1440
NLAYLPLDVN VPATRLESIL SAVGGRKLVL LGADVADPGL RLADVELVRI GDTLGRCVPG    1500
APGDNEAPVV QPSATSLAYV IFTSGSTGKP KGVMVEHRGV VRLVKQSNVV YHLPSTSRVA    1560
HLSNLAFDAS AWEIYAALLN GGTLICIDYF TTLDCSALGA KFIKEKIVAT MIPPALLKQC    1620
LAIFPTALSE LVLLFAAGDR FSSGDAVEVQ RHTKGAVCNA YGPTENTILS TIYEVKQNEN    1680
FPNGVPIGRA VSNSGAYVMD PQQQLVPLGV MGELVVTGDG LARGYTDPSL DADRFVQVSV    1740
NGQLVRAYRT GDRVRCRPCD GQIEFFGRMD RQVKIRGHRI ELAEVEHAVL GLEDVQDAAV    1800
IAFDNVDSEE PEMVGFVTIT EDNPVREDET SGQVEDWANH FEISTYTDIA AIDQGSIGSD    1860
FVGWTSMYDG SEIDKAEMQE WLADTMASML DGQAPGNVLE IGTGTGMVLF NLGDGLQSYV    1920
GLEPSRSAAA FVNQTIKSLP TLAGNAEVHI GTATDVARLD GLRPDLVVVN SVVQYFPSPE    1980
YLMEVVEALA RLPGVERIFF GDVRSYAINR DFLAARALHE LGDRATKHEI RRKMLEMEER    2040
EEEELLVDPA FTMLTSSLPG LIQHVEILPK LMRATNELSA YRYTAVVHVC RAGQEPRSVH    2100
TIDDDAWVNL GASRLSRPTL SSLLQTSEGA SAVAVSNIPY SKTITERALV SALDEDDMQD    2160
SSDWLLAVRE TGRSCSSFSA TDLVELARET GWRVELSWAR QYSQKGALDA VPHRHPVSAG    2220
SGRVMFQFPV ETEDRPHISR TNRPLQRLQK KRTETHVHEQ LRALLPRYMV PTRIVALDKL    2280
PVNANGKVDR QQLARTAQVL PASKAPSACV APRNELEMTL CEEFSQVLGV EVGITDNFFH    2340
LGGHSLMATK FAARISRRLN AIVSVKNVFD HPVPMDLAAT IQEGSKLHTP IPRTAYSGPV    2400
EQSFAQGRLW FLDQFNPSSI GYVMPFAARL HGQLQIEALT AALFALEQRH EILRTTLDAH    2460
DGVGMQIVHA EHPQQLRIID VSAKASSSYA QTLRDEQASP FDLSKEPGWR VSLLQLSEID    2520
YVLSIVMHHT IYDGWSLDVL RRELSQFYAA AIRGREPLST IEPLPIQYRD FSVWQKQEDQ    2580
VAEHRRQLHY WIEQLDGSSP AEFLNDKPRP TLLSGKAGVV EIAVKGTVYQ RLLEFCRLHQ    2640
VTSFMVLLAA FRATHYRLTG TEDATVGTPI ANRNRPELEN NMIGFFVNTQC IRLKIEDNDT    2700
LEELVQHVRA TITASISNQD VPFEQVVSAL LPGSRDTSRN PLVQLTFAVH SQRNLADIQL    2760
ENVETNAMPI CPSTRFDAEF HLFQEENMLS GRVLFSDDLF EQKTMQGMVD VFQEVLSRGL    2820
EQPQIPLATL PLTHGLEELR TMGLLDVEKT DYPRESSVVD VFREQAAACS EAIAVKDSSA    2880
QLTYSELDRQ SDELAGWLRQ QRLPAESLVA VLAPRSCQTI VAFLGILKAN LAYLPLDVNV    2940
PATRLESILS AVGGRKLVLL GADVADPGLR LADVELVRIG DTLGRCVPGA PGDNEAPVVQ    3000
PSATSLAYVI FTSGSTGKPK GVMVEHRSIV RLMRHSNVSS RLLLHPRMTH LSNLAFDASV    3060
WEIFLTLLNG GTLICIDYLS SLDCRALGVS ILEHQVDASV LPPALLKQCL ANVPEALASL    3120
QVLLSAGDRL DSRDAIESCA LVRGSVYNGY GPTENGIQST IYEVKADAEF VNGVPIGRAV    3180
SNSGAYVMDP QQQLVPLGVM GELVVTGDGL ARGYTDPSLD ADRFVQVSVN GQLVRAYRTG    3240
DRVRCRPCDG QIEFFGRMDR QVKIRGHRIE LAEVEHAVLG LEDVQDAAVL IAQTAENEEL    3300
VGFFTLRQTQ AVQSNGAAGV VPEHSDSELA QSCSCTQTER RVRNRLQSCL PRYMVPSRMV    3360
LLDRLPVNPN GKVDRQELTR RAQDLPISES SPVHVKPRTE LERSLCEEFA DVIGLEVGVT    3420
DNFFDLGGHS LMAMKLAARI SRRSNAHISV KDIFDHPLIA DLAMKIREGS DLHTPIPHRM    3480
YVGPIQLSFA QGRLWFLDQL NLGASWYVMP LAMRLQGSLQ LDALETALFA IEQRHETLRM    3540
TFAEQDGVAV QVVHAAHYKH IKMIDKPLRQ KIDVLKMLEE ERTTPFELSR EPGWRVALLR    3600
LGDDDHVLSI VMHHIISDGW SVDVLRHELG QFYSAALRGQ DPLSQISPLP IQYRDFALWQ    3660
RQDEQVAEHQ RQLEHWTEQL ADSSPAELLS DHPRPSILSG QAGAIPVNVQ GSLYQALRAF    3720
CRAHQVTSFV VLLTAFRIAH YRLTGAEDAT IGTPIANRNR PELENMIGFF VNTQCMRIVI    3780
GSDDTFEGLV QQVRSITAAA HENQDVPFER IVSALLPGSR DTSRNPLVQL MFAVHSQRNL    3840
GQISLEGLQG ELLGVAATTR FDVEFHLFQD DDKLSGNVLF ATELFEQKTM QGMVDVFQEV    3900
LSRGLEQPQI PLATLPLTHG LEELRTMGLL DVEKTDYPRE SSVVDVFREQ AAACSEAIAV    3960
KDSSAQLTYS ELDRQSDELA GWLRQQRLPA ESLVAVLAPR SCQTIVAFLG ILKANLAYLP    4020
LDVNVPATRL ESILSAVGGR KLVLLGADVA DPGLRLADVE LVRIGDTLGR CVPGAPGDNE    4080
APVVQPSATS LAYVIFTSGS TGKPKGVMVE HRSIVRLMRH SNVSSRLLLH PRMTHLSNLA    4140
FDASVWEIFL TLLNGGTLIC IDYLSSLDCR ALGVSILEHQ VDASVLPPAL LKQCLANVPE    4200
ALASLQVLLS AGDRLDSRDA IESCALVRGS VYNGYGPTEN GIQSTIYEVK ADAEFVNGVP    4260
IGRAVSNSGA YVMDPQQQLV PLGVMGELVV TGDGLARGYT DPSLDADRFV QVSVNGQLVR    4320
AYRTGDRVRC RPCDGQIEFF GRMDRQVKIR GHRIELAEVE HAVLGLEDVQ DAAVIAFDNV    4380
DSEEPEMVGF VTITEDNPVR EDETSGQVED WANHFEISTY TDIAAIDQGS IGSDFVGWTS    4440
MYDGSEIDKA EMQEWLADTM ASMLDGQAPG NVLEIGTGTG MVLFNLGDGL QSYVGLEPSR    4500
SAAAFVNQTI KSLPTLAGNA EVHIGTATDV ARLDGLRPDL VVVNSVVQYF PSPEYLMEVV    4560
EALARLPGVE RIFFGDVRSY AINRDFLAAR ALHELGDRAT KHEIRRKMLE MEEREEELLV    4620
DPAFFTMLTS SLPGLIQHVE ILPKLMRATN ELSAYRYTAV VHVCRAGQEP RSVHTIDDDA    4680
WVNLGASRLS RPTLSSLLQT SEGASAVAVS NIPYSKTITE RALVSALDED DMQDSSDWLL    4740
AVRETGRSCS SFSATDLVEL ARETGWRVEL SWARQYSQKG ALDAVFHRHP VSAGSGRVMF    4800
QFPVETEDRP HISRTNRPLQ RLQKKRTETH VHEQLRALLP RYMVPTRIVA LDKLPVNANG    4860
KVDRQQLART AQVLPASKAP SACVAPRNEL EMTLCEEFSQ VLGVEVGITD NFFHLGGHSL    4920
MATKLAARIS HRLHTRISVK HIFDHPLIGD LSVHIADSPV PLLTITRAQH AGAVEQSFAQ    4980
ARLWFLVQLG LESPSYIIPI VLRLHGSLSK TAIEGALSAL MERHEVLRTT FEDHKGIGMQ    5040
VVQDHRHQDL VVIDVAGQGS LDYKQHLYME HVKPFDLTRD PGWRVALLRL GDDDHVLSIV    5100
MHHIISDGWS IDILLRELGQ FYSAALRGQD PLSQTSPLPI QYRDFALWQK QDHQLADHEK    5160
QLRYWEEQLA ESSPAELLCD HARPTTPSGQ AGSIPVNVQG SLYQALRAFC RAHQVTSFVV    5220
LLTAFRIAHY RLTGAEDATI GTPIANRNRP ELENMIGFFV NTQCMRIVIG SDDTFEGLVQ    5280
QVRSITAAAH ENQDVPFERI VSALLPGSRD TSRNPLVQLL FAVHAYQEVE NFAIPGVHSE    5340
LVQGTTFTRF DVEFHLLEDP DKLSGNVLFA TELFEQKTMQ GMVDVFQEVL SRGLEQPQIP    5400
```

```
LATLPLTHGL EELRTMGLLD VEKTDYPRES SVVDVFREQA AACSEAIAVK DSSAQLTYSE  5460
LDRQSDELAG WLRQQRLPAE SLVAVLAPRS CQTIVAFLGI LKANLAYLPL DVNVPATRLE  5520
SILSAVGGRK LVLLGADVAD PGLRLADVEL VRIGDTLGRC VPGAPGDNEA PVVQPSATSL  5580
AYVIFTSGST GKPKGVMVEH RSILRVVTSP PARALLPSTI IMAHLTNIAF DVSLWEICTA  5640
LLHGGTLICI QYLASLDVRG LQTTFSREAI NVAVFPPALL KTCLAKIPSA LASLSAMFSS  5700
GDRLDSRDAS EGATLVRQGI HNAYGPTENG IQSTIYEVKA DAEFVNGVPI GRAVSNSGAY  5760
VMDPQQQLVP LGVMGELVVT GDGLARGYTD PSLDADRFVQ VSVNGQLVRA YRTGDRVRCR  5820
PCDGQIEFFG RMDRQVKIRG HRIELAEVEH AILSLDYVID AAVLLRQLID QEPQVVGFVI  5880
VSTKRAYSRH NSGYASEVSA FCIKDQIAWR IRQHLCRMLP SYMVPYQIAI LDEMPINANG  5940
KVDRQNLASR TVNVQRILAA PYMAPRNEVE ISLCEQYAAL LEHDVGILDD FFELGGHSLM  6000
ATRLASRISS RFSAPVSVRD IFDHPRIMDL ASIIRAGDIQ WSRILPSAYE RPVEQSFAQN  6060
RLWFLYKLDI GTTQYNLPLA IHLRGPLDIS ALFIAFKALT ERHELLRTTF DEDDGTCLQM  6120
LLPEYQHEVR ITDLQGSHKG SLLDILNNNQ KTPFELSREP GWRVALLRLG DDDHVLSIVM  6180
HHIISDGWSV DVLRHELGQF YSAALRGQDP LSQISPLPIQ YRDFALWQRQ DEQVAEHQRQ  6240
LEHWTEQLAD SSPAELLSDH PRPSILSGQA GAIPVNVQGS LYQALRAFCR AHQVTSFVVL  6300
LTAFRIAHYR LTGAEDATIG TPIANRNRPE LENMIGFFVN TQCMRIVIGS DDTFEGLVQQ  6360
VRSITAAAHE NQDVPFERIV SALLPGSRDT SRNPLVQLMF AVHSQRNLGQ ISLEGLQGEL  6420
LGVAATTRFD VEFHLFQDDD KLSGNVLFAT ELFEQKTMQG MVDVFQEVLS RGLEQPQIPL  6480
ATLPLTHGLE ELRTMGLLDV EKTDYPRESS VVDVFREQAA ACSEAIAVKD SSAQLTYSEL  6540
DRQSDELAGW LRQQRLPAES LVAVLAPRSC QTIVAFLGIL KANLAYLPLD VNVPATRLES  6600
ILSAVGGRKL VLLGADVADP GLRLADVELV RIGDTLGRCV PGAPGDNEAP VVQPSATSLA  6660
YVIFTSGSTG KPKGVMVEHR GVVRLVKQSN VVYHLPSTSR VAHLSNLAFD ASVLEIYAAL  6720
LNGGTVYCID YLTTLDPHAL ESVFIDADLN TAVLPPALLK QVLASSPSTL HALDLLFIGG  6780
DRLDARDALY ANRLVRGSLY NVYGPTENTV LSVVYLFNDD DACINGVPIG QVVSNSGVYV  6840
MDSEQKLVPP GVMGEIVVTG DGLARGYTDS TLNTDRFVQI SVNGRVLQAY RTGDRGRYRP  6900
TDARLEFFGR LDQQIKLRGH RVELKEIEQA MLGHNAVDDA GVVALEISEC QELEMVGFVT  6960
LRNLGTMEAT NNLAHTSWNP VTLKTPLASQ IVAEVRGRLQ RNLPLYMVPA TIVVLHTMPV  7020
NANGKLDRQA LVKAAMTLPK TAPLVWMAPR NEGETSLCEE LTDILGVNVG ITDNFFDLGG  7080
HSLLATRVAA RISRRLDALV TVKQIFDHPV IGDLAAAIQG GSVRHLPITA SEVDGPVQQS  7140
FAQNRLWFLE QMNIGATWYI VPLAVRLYGT LRVEALNIAL RTIQQRHETL RTTFEELNGI  7200
AVQRCDSTCQ GQLRVVDLVG QGPDRYREIL DVQQTTPFEL SQEPGWRVAL LRLGDDDHVL  7260
SIVMHHIISD GWSVDVLLRE IGQFYSAALR GQDPLSQISP LPIQYRDFAL WQRQDEQVAE  7320
HQRQLEHWTE QLADSSPAEL LSDHPRPSIL SGQAGAIPVN VQGSLYQALR AFCRAHQVTS  7380
FVVLLTAFRI AHYRLTGAED ATIGTPIANR NRPELENMIG FFVNTQCMRI VIGSDDTFEG  7440
LVQQVRSITA AAHENQDVPF ERIVSALLPG SRDTSRNPLV QLMFAVHSQR NLGQISLEGL  7500
QGELLGVAAT TRFDVEFHLF QDDDKLSGNV LFATELFEQK TMQGMVDVFQ EVLSRGLEQP  7560
QIPLATLPLT HGLEELRTMG LLDVEKTDYP RESSVVDVFR EQAACSEAI AVKDSSAQLT  7620
YSELDRQSDE LAGWLRQQRL PAESLVAVLA PRSCQTIVAF LGILKANLAY LPLDVNVPAT  7680
RLESILSAVG GRKLVLLGAD VADPGLRLAD VELVRIGDTL GRCVPGAPGD NEAPVVQPSA  7740
TSLAYVIFTS GSTGKPKGVM VEHRGVVRLV KQSNVVYHLP STSRVAHLSN LAFDASAWEI  7800
YAALLNGGTL ICIDYFTTLD CSALGAKFIK EKIVATMIPP ALLKQCLAIF PTALSELVLL  7860
FAAGDRFSSG DAVEVQRHTK GAVCNAYGPT ENTILSTIYE VKQNENFPNG VPIGRAVSNS  7920
GAYVMDPQQQ LVPLGVMGEL VVTGDGLARG YTDPSLDADR FVQVSVNGQL VRAYRTGDRV  7980
RCRPCDGQIE FFGRMDRQVK IRGHRIELAE VEHAVGLED VQDAAVIAFD NVDSEEPEMV  8040
GFVTITEDNP VREDETSGQV EDWANHFEIS TYTDIAAIDQ GSIGSDFVGW TSMYDGSEID  8100
KAEMQEWLAD TMASMLDGQA PGNVLEIGTG TGMVLFNLGD GLQSYVGLEP SRSAAAFVNQ  8160
TIKSLPTLAG NAEHVIGTAT DVARLDGLRP DLVVVNSVVQ YFPSPEYLME VVEALARLPG  8220
VERIFFGDVR SYAINRDFLA ARALHELGDR ATKHEIRRKM LEMEEREEEL LVDPAFFTML  8280
TSSLPGLIQH VEILPKLMRA TNELSAYRYT AVVHVCRAGQ EPRSVHTIDD DAWVNLGASR  8340
LSRPTLSSLL QTSEGASAVA VSNIPYSKTI TERALVSALD EDDMQDSSDW LLAVRETGRS  8400
CSSFSATDLV ELARETGWRV ELSWARQYSQ KGALDAVFHR HPVSAGSGRV MFQFPVETED  8460
RPHISRTNRP LQRLQKKRTE THVHEQLRAL LPRYMVPTRI VALDKLPVNA NGKVDRQQLA  8520
RTAQVLPASK APSACVAPRN ELEMTLCEEF SQVLGVEVGI TDNFFHLGGH SLMATKFAAR  8580
ISRRLNAIVS VKNVFDHPVP MDLAATIQEG SKLHTPIPRT AYSGPVEQSF AQGRLWFLDQ  8640
FNPSSIGYVM PFAARLHGQL QIEALTAALF ALEQRHETLR TTLDAHDGVG MQIVHAEHPQ  8700
QLRIIDVSAK ASSSYAQTLR DEQASPFDLS KEPGWRVSLL QLSEIDYVLS IVMHHTIYDG  8760
WSLDVLRREL SQFYAAAIRG REPLSTIEPL PIQYRDFSVW QKQEDQVAEH RRQLHYWIEQ  8820
LDGSSPAEFL NDKPRPTLLS GKAGVVEIAV KGTVYQRLLE FCRLHQVTSF MVLLAAFRAT  8880
HYRLTGTEDA TVGTPIANRN RPELENMIGL FVNTQCIRLK IEDNDTLEEL VQHVRATITA  8940
SISNQDVPFE QVVSALLPGS RDTSRNPLVQ LTFAVHSQRN LADIQLENVE TNAMPICPST  9000
RFDAEFHLFQ EENMLSGRVL FSDDLFEQKT MQGMVDVFQE VLSRGLEQPQ IPLATLPLTH  9060
GLEELRTMGL LDVEKTDYPR ESSVVDVFRE QAACSEAIA VKDSSAQLTY SELDRQSDEL  9120
AGWLRQQRLP AESLVAVLAP RSCQTIVAFL GILKANLAYL PLDVNVPATR LESILSAVGG  9180
RKLVLLGADV ADPGLRLADV ELVRIGDTLG RCVPGAPGDN EAPVVQPSAT SLAYVIFTSG  9240
STGKPKGVMV EHRGVVRLVK QSNVVYHLPS TSRVAHLSNL AFDASAWEIY AALLNGGTLI  9300
CIDYFTIIDA RALGVIFAQQ SINATMLSPL LLKQFLSDAP FVLRSLHALY LGGDRLQGRD  9360
AIQACRVGCA FVINAYGPTE NSVISTTYTL VKGNADFPNG VPIGRAVSNS GAYVMDPQQQ  9420
LVPLGVMGEL VVTGDGLARG YTDPSLDADR FVQVSVNGQL VRAYRTGDRV RCRPCDGQIE  9480
FFGRMDRQVK IRGHRIELAE VEHAVGLED VQDAAVLIAQ TAENEELVGF FTLRQTQAVQ  9540
SNGAAGVVPE HSDSELAQSC SCTQTERRVR NRLQSCLPRY MVPSRMVLLD RLPVNPNGKV  9600
DRQELTRRAQ DLPISESSPV HVKPRTELER SLCEEFADVI GLEVGVTDNF FDLGGHSLMA  9660
MKLAARISRS SNAHISVKDI FDHPLIADLA MKIREGSDLH TPIPHRMYVG PIQLSFAQGR  9720
LWFLDQLNLG ASWYVMPLAM RLQGSLQLDA LETALREQL RHETLRMTFA EQDGVAVQVV  9780
HAAHYKHIKM IDKPLRQKID VKMLEEERT TPFELSREPQ WRVALLRGLD DDHVLSIVMH  9840
HIISDGWSVD VLRHELGQFY SAALRGQDPL SQISPLPIQY RDFALWQRQD EQVAEHQRQL  9900
EHWTEQLADS SPAELLSDHP RPSILSGQAG AIPVNVQGSL YQALRAFCRA HQVTSFVVLL  9960
TAFRIAHYRL TGAEDATIGT PIANRNRPEL ENMIGFFVNT QCMRIVIGSD DTFEGLVQQV 10020
RSITAAAHEN QDVPFERIVS ALLPGSRDTS RNPLVQLMFA VHSQRNLGQI SLEGLQGELL 10080
GVAATTRFDV EFHLFQDDDK LSGNVLFATE LFEQKTMQGM VDVFQEVLSR GLEQPQIPLA 10140
```

```
TLPLTHGLEE LRTMGLLDVE KTDYPRESSV VDVFREQAAA CSEAIAVKDS SAQLTYSELD   10200
RQSDELAGWL RQQRLPAESL VAVLAPRSCQ TIVAFLGILK ANLAYLPLDV NVPATRLESI   10260
LSAVGGRKLV LLGADVADPG LRLADVELVR IGDTLGRCVP GAPGDNEAPV VQPSATSLAY   10320
VIFTSGSTGK PKGVMVEHRG VVRLVKQSNV VYHLPSTSRV AHLSNLAFDA SAWEIYAALL   10380
NGGTLICIDY FTTLDCSALG AKFIKEKIVA TMIPPALLKQ CLAIFPTALS ELVLLFAAGD   10440
RFSSGDAVEV QRHTKGAVCN AYGPTENTIL STIYEVKQNE NFPNGVPIGR AVSNSGAYVM   10500
DPQQQLVPLG VMGELVVTGD GLARGYTDPS LDADRFVQVS VNGQLVRAYR TGDRVRCRPC   10560
DGQIEFFGRM DRQVKIRGHR IELAEVEHAV LGLEDVQDAA VIAFDNVDSE EPEMVGFVTI   10620
TEDNPVREDE TSGQVEDWAN HFEISTYTDI AAIDQGSIGS DFVGWTSMYD GSEIDKAEMQ   10680
EWLADTMASM LDGQAPGNVL EIGTGTGMVL FNLGDGLQSY VGLEPSRSAA AFVNQTIKSL   10740
PTLAGNAEVH IGTATDVARL DGLRPDLVVV NSVVQYFPSP EYLMEVVEAL ARLPGVERIF   10800
FGDVRSYAIN RDFLAARALH ELGDRATKHE IRRKMLEMEE REEELLVDPA FFTMLTSSLP   10860
GLIQHVEILP KLMRATNELS AYRYTAVVHV CRAGQEPRSV HTIDDDAWVN LGASRLSRPT   10920
LSSLLQTSEG ASAVAVSNIP YSKTITERAL VSALDEDDMQ DSSDWLLAVR ETGRSCSSFS   10980
ATDLVELARE TGWRVELSWA RQYSQKGALD AVFHRHPVSA GSGRVMFQFP VETEDRPHIS   11040
RTNRPLQRLQ KKRTETHVHE QLRALLPRYM VPTRIVALDK LPVNANGKVD RQQLARTAQV   11100
LPASKAPSAC VAPRNELEMT LCEEFSQVLG VEVGITDNFF VLGGHSLMAT KLAARISRQL   11160
NIQVSVRDIF DYPVIVDLTD RLRLHHTRIL THDHGQHGQP DLKPFTLLPT NNPQEFLQHH   11220
ILPQLVPDHA KILDVYPVTR IQRRFLHHPK RGLPRFPSMV FFDFPPGSDP HKLRLACMAL   11280
VQRFDILRTI FLSVSGQFFQ VVLDGYGIVI PVIEVDEELD DATRKLHDSD IQQPLRLGKP   11340
LIRIAVLKRQ HSRVRAVLRL SHALYDGLSF EHIIQSLHAL YLDITLSAPP KFGLYVQHMI   11400
QSRAEGYAFW RSVLKGSSMT ILERSSTLQS RQPHLGRFLS AEKIIKAPLH ANKSGITQAT   11460
VFAAANALML ANLTGTNDVV FARIVSGRQS LPKNFQHVVG PCTNDVPRV RMEPGVGPKA   11520
LLRQVQDQYV HSFPPFETLGF DEIKENCTDW PERITNFGCS TTYQNFDIFP KSQIDHQQIQ   11580
MASLASEYQN RETWDEAPLY DLNVTGVPQP DGRHIKIYVG VDGQLCDEST LDCILSDICE   11640
GVVSLTDALQ ELPAASITE                                                11659

SEQ ID NO: 7            moltype = DNA   length = 2103
FEATURE                 Location/Qualifiers
source                  1..2103
                        mol_type = unassigned DNA
                        note = Aureobasidium melanogenum strain W5-2
                        organism = unidentified
SEQUENCE: 7
atggcttcat ctaatggccc gatgaattcc cccttttgaat tgatcccccaa ggtcgtcaat    60
aagaagaatt actatactga cttcttgaag cgcgatgagc aattcctcgc atttcgcctt   120
caaggcgagg agaaccgtaa tcgcatgatc aaagctgcgc gcgataagga ccgcgcaatg   180
gctcaggctg cttctaatgg agtctcagct gatgctgcgc aagctgagat tgacgatgat   240
gccgccgagg atgaagctgc tgaagctgaa gcctttgcct caaagacgat tgtcattcat   300
cctggcagtc gcaacctacg tattggtctt gcaacagacg cccttcccaa gacaatcccg   360
atggtgattg cacgcaaggc ttcacatgca gaagacgagg agcctggcgc tgaaccgcgg   420
ccaaagcgag tcaagatgca ggatggtacg gcagagcctg ctggcgagag tgcgttcggc   480
gaagatttcg caaaggaata cagtagcatg gcagctgact tcaaaatcta ccgtcgcaac   540
aacaaacgta gagtcttgcc caactcgcgt gaactggtcg tcaactggaa ctcgcgcaat   600
gctccggaaa ccatttctga acataacgat cctcagcgtg ttgactggac agaaattgtg   660
tcacctgcac ccgaaatctt cactggacat gcagctctgc gaataccaca gcattccaaa   720
ccccgataca gactctactg gccactcaaa tgtggttggc tcaatgaaca agactattcg   780
agcaaatcta gcttatttcg cgacttcttc agcatcatcg aagaggccat caagaacgag   840
cttcacctga accgtaagag agactgggca cagtactctt gcgtgttcat cattcccgat   900
ctgtacgaga agttttcgt gacatccatc ctcgaggaaa tgttcagaga cttcggtttc   960
cagcgtgtt gcttcatcca agaaagtctg gcagcaactc ttggagctgg atactcgagc  1020
agttgtattg ttgatgttgg tgcacaaaag acttctatct gctcgcgttga ggaaggcatg  1080
tgcgtcgaga actcccgcat gaacctgaag tttggcggag aagatgttac agaaacattc  1140
atcaagatga tgctgtacga ccacttcaat tatgccaaca tggatctgct gaggagacat  1200
gactacctc ttgcggaaga gctgaagcaa aagttctgca cgctcgagga tgcacatatc  1260
agcgtacagc tttatgagtt ccatctccgt gcgttcggcc aagacactcg caaataccag  1320
ttcaagacgt atgatgaagt catgctggca cctatgggtt tcttcaggcc aacaatattt  1380
gatcattcag acaagctcgc tggcagacgc aagctcatcg tcgctcaac tgacacttac  1440
gatgataaac ctaatgatcc catgtcactc gctcaactgc aggtctacaa gtactcgtcc  1500
gataatgttc cctcagctgt agcagaatca agtacaccgg cacctggtgg cgtgcctgca  1560
acacccagca aacccttgaa cctgaccgc ctaacgcatc ttgccgatgt agcggaaagt  1620
acacctcgtt cctctccagc aggatcgcct gctcctgacg acacggcaac accagtacca  1680
ggagctggac acgcaacacc agccgtagca ggtggcggga tcgaaggtgc acagccaaat  1740
actgaagatg tgctgcctgt gatgccctg gatcaagcaa ttgtcacatg catcaccgaa  1800
ggcgccaagg gtgatgagaa gaagacgcgt gacttcttcg gtggtatcat ggtgatcgga  1860
ggcggtagca agacttacaa tttcaacgtc tatctcgagc agagacttcg cgcgctacag  1920
ccaaacttcc agaaggaaat cttggttgga cctccgccta gagagctcga tcctcaggtt  1980
ctggtgtgga agggcggtag tgtgtttggc aagatgagag gcactaatga cagctggatc  2040
ggacagttgg agtttgacag actgggtgcc agaatcttga accagaagtg tatgtgggca  2100
tac                                                                 2103

SEQ ID NO: 8            moltype = DNA   length = 1377
FEATURE                 Location/Qualifiers
source                  1..1377
                        mol_type = unassigned DNA
                        note = Aureobasidium melanogenum strain W5-2
                        organism = unidentified
SEQUENCE: 8
atgggtaagg aaaagtccca cattaacgtc gtcgttatcg gccacgtcga ctccggtaag    60
```

```
tcgaccacca ccggtcactt gatctacaag tgcggtggta tcgacaagcg taccatcgag    120
aagttcgaga aggaagccgc cgaactcggc aaggggttcct tcaagtacgc ctgggtcctc    180
gacaagctga agtctgagcg tgagcgtggt atcactatcg atatcgccct gtggaagttc    240
gagacccca agtacatggt caccgtcatc gacgccccg gtcaccgtga tttcatcaag    300
aacatgatca ctggtacctc gcaggctgac tgcgccattc tcatcattgc cgccggtact    360
ggtgagttcg aggctggtat ctccaaggat ggccagaccc gtgagcacgc ccttctcgcc    420
tacaccctcg gtgtcaagca gctcatcgtt gccatcaaca agatgacac caccaagtgg    480
tccgaggccc gttaccagga gatcatcaag gagacctccg gtttcatcaa gaaggtcggc    540
tacaacccca agcacgttcc cttcgtcccc atctccggtt tcaacggtca acatgatc    600
gaggtttcca ccaactgccc ctggtacaag ggttgggaga aggagaccaa ggccaaggcc    660
accggcaaga ctctcctcga agccattgac gccatcgacc ctcctacccg ccccaccgac    720
aagcccctcc gtcttcccct ccaggatgtc tacaagatcg tggtattgg cacggtgccc    780
gtcggccgtg tcgagaccgg taccatcaag ggtggtatgg tcgtcacctt cgcccccgct    840
ggtgtcacca ctgaggtcaa gtccgtcgag atgcaccacg agcagctcgc cgagggtctt    900
cccggtgaca acgtcggctt caacgtcaag aacgtctccg tcaaggagat ccgtcgtggt    960
aacgttgccg tgactccaa gaacgacccc ccaagggtt gtgactcctt caacgcccag   1020
gtcatcgtc tgaaccaccc cggtcaggtc ggtgctggtt acgcacccgt cctcgactgc   1080
cacactgccc acatccgctc caagttctcc gagcttgttg agaagatcga ccgccgtacc   1140
ggcaagtccg ttgaggccgc ccccaagttc atcaagtctg tgacgccgc cattgtcaag   1200
atggttccct ccaagcccat gtgtgttgag gccttcactg actaccctcc tctcggtcgt   1260
ttcgccgtcc gtgacatgag acagaccgtc gccgtcggtc atcaagtc tgtcgccaag   1320
tccgacaagg gtggtgccgg taaggtcact aaggccgccc tcaaggctgg caagaag     1377

SEQ ID NO: 9              moltype = DNA   length = 1341
FEATURE                   Location/Qualifiers
source                    1..1341
                          mol_type = unassigned DNA
                          note = Aureobasidium melanogenum strain W5-2
                          organism = unidentified
SEQUENCE: 9
atgcgtgaga ttgtccacct ccagaccggc caatgcggta accaagttgg tgctgccttc    60
tggcagacca tctctggcga gcacggcctt gacggtgctg gtgtctacaa cggtacctca   120
gatctccagc tggagcgcat gaacgtctac ttcaacgagg cctctggtaa caaatatgtt   180
ccccgtgccg tcctcgtcga cttggagcct ggtaccatgg acgccgtccg tgctggtatc   240
ttcggtcagc tcttccgtcc cgacaacttc gtcttcgtc agtccggtgc tggcaacaac   300
tgggccaagg tcactacac tgagggtgcc gagttggtcg accaggtctt ggatgtcgtt   360
cgtcgtgagg ccgagagctg tgactgcctc caaggtttcc agatcactca ctcgctcggt   420
ggtggtaccg gtgccggtat gggaacgctc ctcatctcca agatccgtga ggagttcccc   480
gaccgtatga tggccacctt ctccgtcatg ccctccccca aggtctccga caccgttgtc   540
gagccttaca acgctaccct ctccgtccac cagctcggtcg agaactctga cgagaccttc   600
tgtatcgaca accaggctct ctacgacatc tgcatgagca ccctcaagct caacaacccc   660
tcctacggcg acctgaacta cctcgtctcc gccgtcatgt ccggtgttac cgtctcgctc   720
cgtttccctg gccagtcaa ctccgacttg cgcaagctcg ccgtcaacat ggtgcccttc    780
ccccgtctcc acttcttcat ggtcggtttt gctcctctca ccagccgtaa cgccactcg    840
ttccgcgccg tctcggttcc cgagctcacc cagcaaatct tcgacccaa gaacatgatg    900
gccgccaccg atttccgcaa cggccgctac ctgacctgct ctgccatctt ccgtggtaag    960
gtctccatga aggaggtcga ggaccagatg cgcaacgtcc agaacaagaa ctccgcctac   1020
ttcgttgagt ggatccccaa caacgtccga accgccctct gctccattcc tcctcgtggt   1080
cttaagatgt catcgaccct cgtcggtaac tcgacctcga tccaggagct gttcaagcgt   1140
gtcggtgacc agtttctctgc catgttccgt cgcaaggctt tcttgcactg gtacactggt   1200
gagggtatgg acgagatgga gttcactgag gctgagtcta acatgaacga cttggtcagc   1260
gagtaccagc agtaccagga ggcttccatc tccgagggta aggaggagta cgacgaggag   1320
gctcctatgg aggctgagga g                                            1341

SEQ ID NO: 10             moltype = DNA   length = 6093
FEATURE                   Location/Qualifiers
source                    1..6093
                          mol_type = unassigned DNA
                          note = Aureobasidium melanogenum strain W5-2
                          organism = unidentified
SEQUENCE: 10
cggccggcgc cttgcaacat caacgcccgt catatcctcg acctcaccct tgctgctacc    60
acgccctcac caaccgcatc gccgcgcatc acctccattg cgcgcaatcg ccgtctcgag   120
tcgcgtcgct cctccatcgc ctgtcgattt ctctgttttcg ccgctgtccg cctgcgcacg   180
cgccgttcga aaggccagtc gctcgacacg cgctcttccg ccagaggcaa ccctcttaca   240
tccacaatca tccaccttat caccactttc atctgtcctg gagatccacg ctcaacctct   300
ccgtcgacag cgccctgaag gcggcagccg ctgatacgat tcttacacaa tttctcttag   360
ctattgctat caacatccgc caccatgaac atccactctt ttcccctattc cagcgctccg   420
ctgaagacca ttcaggagat tcagttttggt ctcttctctc ctgaggagat caagaacatg   480
agtgtgtgtc acatcgagta cccagagacc atggacgagc aacggatgcg tccgcgagag   540
aagggcttaa cgaccccaa gctgggctct atcgatcgct cagttgcctg tggtacctgc   600
ggtgaagaca tgctggagtg tccggtcac tttggtcata ttgagcttgc tgtgcccgtc   660
ttccacgtcg gttttgtcac caagatcaag aagattctcg aaaccgtctg ccacaactgt    720
ggcaaagtct tgccttgatga agcattcct gccttcgtcc aagctgtccg cataagagat    780
cccaagcgcg gcttcgatgc tgttcacaga ctgtgcaagg ccaagacgac ctgcgatccc    840
gatgaggctg gtgacgatgg agaagacccg aagacgcctt gaagaaggg caagcgatca    900
cacggtggct gcggtaaacct gcaacccaca attcgcaagg acgtcttaa gcttaccggc    960
acctacacat accccaagga cgccgataca gaacaaaagc ccgtggagaa gaaggtcatc   1020
accctcaga tggcactgaa cgtttccgc aacatttcga catacgactt ggccagaatg   1080
```

-continued

```
ggcctcaacg cagactacgc tcgtcccgaa tggatgatcc tgaccgtgtt gcccgtaccg   1140
ccaccagctg ttcgtcccag tgtttcggtc gatggaacca accaaggaat gcgttccgag   1200
gatgatttga ctttcaaact cagtgatatt atccgcgcca atgccaacgt tcgcaagtgt   1260
gagctcgagg gctctccaca ccacgttatt gcagagtttg aggctttgct gcagttccac   1320
gtcgctacat acatggacaa cgatattgca ggacagccta agctctgca aaaatccggt   1380
agacctgtca aggctattcg tgcgcgcctg aagtccaagg agggtcgtct tcgtggtaac   1440
cttatgggca agcgtgtcga tttctccgct cgtacagtca tcactggtga cccgaacttg   1500
tctctggatg aagtaggtgt tcctagaagt accgccgca tccttacctt ccccgagacc    1560
gtcaacgctt tcaacatcga caagctacaa caactcgttc gcaacggtcc caacgaacac   1620
cctggagcaa agtatgtcat tcgagacact ggcgagcgca tcgatttgcg ccatcacaag   1680
cgcgctggcg agattcaact gcaatatggc tacaaagtcg aaagacatat cgtcgatggt   1740
gatgttatta tcttcaaccg tcaaccttcg ctgcacaagg agtctatgat gggtcacaga   1800
gtccgtgtca tgccctactc tactttccgt ctcaaccttt ccgttacttc gccatacaac   1860
gccgatttcg atggtgatga gatgaacttc cacgttcctc agagtcacga aactcgctca   1920
gaagtcatga acctttgcat ggttcccctc aacatcgtct ctcctcagcg taacggtccc   1980
ttgatgggta tcgtgcaaga cactcttttg ggtatctaca agatgtgccg tcgtgatgtt   2040
ttcctggacc aggaacacgt catgaacatt ctcatgtggg tgcctgattg ggacggtgtc   2100
atcccaccac cttctatcct caaacctcgc cctagatgga ctggtaagca gattatcagc   2160
ttgatcgtcc ccactggttt gaaccttgtt cgtggtgatg ctgagggcat gcatcccctc   2220
aacgacaacg gtttgatggt acatggtggc gagctcatgt acggtctgtt cagcaagaag   2280
tccgtcggtg ccagtggagg tggtatcatc cacatcgtct acaacgaaaa gggctgggaa   2340
gctgctgtca gtttcttcaa cggagctcag cgtgtcgtca actactggct gctccacaa    2400
ggtttcagta tcggtattgg tgacacagtt cctgacgagg cgactgccga gccatcaca    2460
gacgcagtca atgagcagaa ggcagaagta gctgctcatca ccgaggctgc tactgctaac   2520
gagcttgaag ctctgcctgg tatgaacgtt cgtgagacgt tcgagagcag agtgtccaag   2580
gctttgaaca gtgctcgtga caacgctggt gaccgtacgg aaaagagttt gaaggatttg   2640
aacaacgcca ttcagatggc tcgttcaggt tccaagggtt cggctatcaa catttcgcag   2700
atgaccgctg tcgtcggcca acaatccgtc gagggaaagc gtattccttt cggcttcaag   2760
tacagatcgc ttccccactt caccaaggac gattactctc ccgagtctcg tggtttcgtc   2820
gagaactcct atctccgcgg attgacacct tcagaattct tcttccacgc catggctgtt   2880
cgtgagggtc tgatcgatac tgctgtcaag actgccgaaa ctggttacat tcagcgtcgt   2940
ctcgtcaagg ctcttgaaga agtcatggcc aagtatgatg gcactgttcg taactccttg   3000
ggcgatatcg tgcaattcgt ctacggtgaa gatggtttgg atgctgtgca tatcgaaggt   3060
caaaagttgg atatcatcaa ctgctccgac agtcaattcg agaagaagtt ccgtattgat   3120
gtcatgactc ccaagatgtc tctttcaccc gacattctcg agcaagcaca cgagattgct   3180
ggagatgttg aggtccagcg tcacctcgac gctgagtatg aagcattgtt ggctgacaga   3240
gctctgctca gagatggccg taccgatgac gaagaaaccc accaacttcc tcttaacatc   3300
acccgtatcg tcgagagtgc taagaccaga ttccgcatca aggatggcgc tcgcagtgat   3360
cttcacccgt ccgacgttat tcccaaggtt cagaacttgc ttgaccagat tgttgttgtt   3420
cgtgagggacg accctcttttc ccaagaagca caatacaacg ccactatcct cttcaaggcc   3480
ctgctcagat cacgtctcgc ttttaagcgt ctggtcaagg agtactcttt gaacaagctc   3540
gcgcttgaca acattcttgg tgatattctg aacagattct caagatcgct tgtcagtccc   3600
ggtgaaatgg ttggtgtctt ggccgcacag tctattggag aacccgcaac acagatgacg   3660
ctcaacactt tccatttcgc tggtgtctcg tccaagaacg ttaccctcgg tgtgcccgt    3720
ctgaaggaaa ttctgaacgt tgctaccaac atcaagacac cttccatgac tgtctaccaa   3780
tctgccgaaa accgccttga tcaggaagct tgcaagcgac ttcgtagtct ggttgagtac   3840
accagtttgc gctccattac tgagaagacc gaaatttgat tcgaccctga cattcaatca   3900
accgttgttg aacaagacag ggatatggtc gagtcttact tcatcatccc gaagagaat    3960
gcagagagtc ccgagactta ctccaagtgg ttgctgcgta tcgttcttgg tcgtagacag   4020
cttttgacaa agggtctttc ggtcgctgat gtcgccgctg ctatcaagaa tgtctaccac   4080
caggagatgt ctattatctt cagtgacgac aacgctgatg agcttgttat tcgtatcaga   4140
ccttcgaacg tgcttatgga gtccaaagaa gacgatgata ccgctcttga ggccgatctg   4200
atcatcggaa gactcgaaac tcatctgttg gacgagcca gacttcgtgg tgtcttgggc    4260
gtcgatcgtc ctttcgtcaa cttcaaggaa cgtctgcgcg tcaaggaaga cggtgctctt   4320
actatgtcca agagcgatcc tcttttgcaag gaatgtttct tggataccag cggaactgct   4380
ctcaaggaag ttcttactgt tgagggcact gatcctaccc gcacttacac taaccacttc   4440
attgacatct tcagtgtgtt cggtattgag gctactagat ccgcattgat gagagaactc   4500
aagcaagtgc tttcgttcga cggttcttat gtcaaccatc gccatcttgc cctcctggtc   4560
gatattatga ccgctcgcgg taaccttatg gctgtcaccc gtcacggtat caaccgtgct   4620
gacactggtg cactgatgcg ttgttcgttc gaagagacgt tcgagattct gttcgaagct   4680
gcctcctcag gtgaacttga cgactgccgt ggtgtttccg aaaacatcat tcttggtcag   4740
cttgcacctt cgggtactgg tgagtttgat gttctttttgg accagcagat gctcagcact   4800
gttgtctctc gtcaccatgg tatgggtgct ggtactcaag ctggcgccgc tcctcttgac   4860
ggtgctatga ctcccctacga tatgggtctt cctcttgccg ggactga gttcttgtt     4920
gactatggtg cttccttctc tcctatggtc caggcaggtg gcgacgagat gggtggtttc   4980
tctgcctacc aaggtggaag cttcagccct tacagtggcg gtcagagccc tggttacgca   5040
cctaccagtc cattcagcat gggtacaagc catcatctc ccggatatgc ctcgccatct    5100
tctcctggct attcacccag atcacctggt gcagctcttg gcagcccgg ctacggcatg   5160
ggttcacctg ccagtccggc gtacaaccca acatcgccca cttactcgcc tacatctcct   5220
gcctacggca agggctctcc cacctcacct tcttactctc ctacatctcc cagctattcg   5280
ccaacttcac ccagctactc gcctacgtcg cctagctact ctcctacctc tccttatac    5340
agccccactt ctcctgctca cagaggatcg ggcatttctc caacctctcc acgatacagc   5400
ccgacatctc cggcttactc gcccacttca cctgcataca gcccgaccag cccctcctac   5460
aaccctggcg gagcctcgca ctcgcctacg tcgcccagct acagcccgca gtcgccagtg   5520
tacagcccaa ccagtccggc acagcagggc tattctccta cctcaccaca gtacactccc   5580
aactctcctg gtcaagcttc gcctaagtat tcacctacta gccccaagta ctcgcccaac   5640
tcgcctggcc aataagcgaa tgaagcgagc agttacccaa ctgggacgta cccttttgctg   5700
ggcccacgtc ttgtcatggg ctagggttaa tatcaaggtc accaacattc cgaaacaact   5760
cgtagtctgg gttttggttc acgaagacga tgcacgagcg ataagagcac aagcaggtac   5820
```

```
attgcgggag attttacaag gcgttcttct ttttctttt ctgctagtct tgttttgag    5880
agaaggaaag ttctccaagg tttgttttc aggctcacaa aattgcatat ggagaacgag    5940
ccaagtgtag tatcagagag gattttcga ggcaaagata aaccaaagat gagataacac    6000
aaatgcgaac aagcaagtcc aaatttctgc tttcgttgaa agtgactgct ggccgagggc    6060
aaaaagcaag tgtaatattt ttttatgtag tcg                                  6093

SEQ ID NO: 11            moltype = AA  length = 11659
FEATURE                  Location/Qualifiers
source                   1..11659
                         mol_type = protein
                         note = Aureobasidium pullulans strain BP-
                         organism = unidentified
SEQUENCE: 11
MSRMPQGAAR RNDCVSEHQG TTDLEDIVRF WERHLDGVNA SAFPALSSSL VVPKPKLQTE     60
HRISLGTAVS DQWSDAVICR AALAVILARY THATEALYGI VVEQPSVSNA QKRSADDASS    120
IVVPIRVQCA SGQFGNDILA AIATHDASCR SLSAIGLDGI RCLDDAKTVA RGLQTVLTVT    180
SRKSVDASSP NILDLENIAS SHGRALMIEC QMSTTSACLR AQYDAGILRN EQVVRLLKQL    240
ALSIQHFRGN AANDLLRDFC FISPGEEMEI AYWNRRSIRT NEVCIHDVIF KRATYMPTDT    300
AVSAWDGEWT YADLDVVSSC LADYVRSLDL RSGQAIPLCF EKSRNTIAAM VAVLKAGHPF    360
CLIDPSTPSA RITQMCEQMS ATVAFASRAL CSIMQAGVSR CIAVDDDLFQ SLSSVIGCPQ    420
MSMTRPQDLA YVIFTSGSTG IPKGSMIEHR GFASCALEFG PQLLIDRNTR ALQFASHAFG    480
ACLLEVLVTL MLGGCVCVPS ENDRLNNLSG FIEQSGVNWT LFTPSFIGAL TPETIRGVHT    540
VVLGGEPMTP FIRDVWASKV QLLSIYGQSE SSTVCSVVKI KPDTTDLSSL GHAIGARFWI    600
VDAENPSRLA PIGCIGELMV ESPGIAREYL SAQEAQMSPF ITKTPAWYPM KQRCSPVKFY    660
MTGDLACYGR DGTVMNLGRK DSQVKIRGQR VELGDVETNL RSVLPKHIIP VVEAIDSIHA    720
SGSKFLVAIL IGANHGMKNE FDTEPRREVS ILDETAVIRI RKSMQDLVPS YCIPTQYICM    780
ERLLTTTTGK ADRKRLRAIC VDLLKPSRRA MVPESSDGPT LKLTAGQVLD EAWHRYLRFD    840
SVLDGSKSKF FDLNGDSITA IKIANAARKH GVMLKVADIL ANPTLADLRA QFQIDFTPQN    900
SILRTSYRGP IQQSFAQNRL WFLDQLNVGA SWYIVPVAVR LQGTVHVDAL VTALCALEQR    960
HETLRTTFEE SDGEGIQRIQ PSGLEQLRLI DVDCVDSDPV QRVLEEEQTT PPELSREPGW   1020
RVALLRLGDD DHVLSIVMHH IISDGWSVDV LRHELGQFYS AALRGQDPLS QISPLPIQYR   1080
DPFALWQRQDE QVAEHQRQLE HWTEQLADSS PAELLSDHPR PSILSGQAGA IPVNVQGSLY   1140
QALRAFCRAH QVTSFVVLLT AFRIAHYRLT GAEDATIGTP IANRNRPELE NMIGFFVNTQ   1200
CMRIVIGSDD TFEGLVQQVR SITAAAHENQ DVPFERIVSA LLPGSRDTSR NPLVQLMFAV   1260
HSQRNLGQIS LEGLQGELLG VASPTRFDVE FHLFQEENML SGRVLFSDDL FEQKTMQGMV   1320
DVFQEVLSRG LEQPQIPLAT LPLTHGLEEL RTMGLLDVEK TDYPRESSVV DVFREQAAAC   1380
SEAIAVKDSS AQLTYSELDR QSDELAGWLR QQRLPAESLV AVLAPRSCQT IVAFLGILKA   1440
NLAYLPLDVN VPATRLESIL SAVGGRKLVL LGADVADPGL RLADVELVRI GDTLGRCVPG   1500
APGDNEAPVV QPSATSLAYV IFTSGSTGKP KGVMVEHRGV VRLVKQSNVV YHLPSTSRVA   1560
HLSNLAFDAS AWEIYAALLN GGTLICIDYF TTLDCSALGA KFIKEKIVAT MIPPALLKQC   1620
LAIFPTALSE LVLLFAAGDR FSSGDAVEVQ RHTKGAVCNA YGPTENTILS TIYEVKQNEN   1680
FPNGVPIGRA VSNSGAYVMD PQQQLVPLGV MGELVVTGDG LARGYTDPSL DADRFVQVSV   1740
NGQLVRAYRT GDRVRCRPCD GQIEFFGRMD RQVKIRGHRI ELAEVEHAVL GLEDVQDAAV   1800
IAFDNVDSEE PEMVGFVTIT EDNPVREDET SGQVEDWANH FEISTYTDIA AIDQGSIGSD   1860
FVGWTSMYDG SEIDKAEMQE WLADTMASML DGQAPGNVLE IGTGTGMVLF NLGDGLQSYV   1920
GLEPSRSAAA FVNQTIKSLP TLAGNAEVHI GTATDVARLD GLRPDLVVVN SVVQYFPSPE   1980
YLMEVVEALA RLPGVERIFF GDVRSYAINR DFLAARALHA LGDRATKHEI RRKMLEMEER   2040
EEELLVDPAF FTMLTSSLPG LIQHVEILPK LMRATNELSA YRYTAVVHVC RAGQEPRSVH   2100
TIDDDAWVNL GASRLSRPTL SSLLQTSEGA SAVAVSNIPY SKTITERALV SALDEDDMQD   2160
SSDWLLAVRE TGRSCSSFSA TDLVELARET GWRVELSWAR QYSQKGALDA VFHRHPVSAG   2220
SGRVMFQFPV ETEDRPHISR TNRPLQRLQK KRTETHVHEQ LRALLPRYMV PTRIVALDKL   2280
PVNANGKVDR QQLARTAQVL PASKAPSACV APRNELEMTL CEEFSQVLGV EVGITDNFFH   2340
LGGHSLMATK FAARISRRLN AIVSKNVFD HPVPMDLAAT IQEGSKLHTP IPRTAYSGPV   2400
EQSFAQGRLW FLDQFNPSSI GYVMPFAARL HGQLQIEALT AALFALEQRH EILRTTLDAH   2460
DGVGMQIVHA EHPQQLRIID VSAKASSSYA QTLRDEQASP FDLSKEPGWR VSLLQLSEID   2520
YVLSIVMHHT IYDGWSLDVL RRELSQFYAA AIRGREPLST IEPLPIQYRD FSVWQKQEDQ   2580
VAEHRRQLHY WIEQLDGSSP AEFLNDKPRP TLLSGKAGVV EIAVKGTVYQ RLLEFCRLHQ   2640
VTSFMVLLAA FRATHYRLTG TEDATVGTPI ANRNRPELEN MIGLFVNTQC IRLKIEDNDT   2700
LEELVQHVRA TITASISNQD VPFEQVVSAL LPGSRDTSRN PLVQLTFAVH SQRNLADIQL   2760
ENVETNAMPI CPSTRFDAEF HLFQEENMLS GRVLFSDDLF EQKTMQGMVD VFQEVLSRGL   2820
EQPQIPLATL PLTHGLEELR TMGLLDVEKT DYPRESSVVD VFREQAAACS EAIAVKDSSA   2880
QLTYSELDRQ SDELAGWLRQ QRLPAESLVA VLAPRSCQTI VAFLGILKAN LAYLPLDVNV   2940
PATRLESILS AVGGRKLVLL GADVADPGLR LADVELVRIG DTLGRCVPGA PGDNEAPVVQ   3000
PSATSLAYVI FTSGSTGKPK GVMVEHRSIV RLMRHSNVSS RLLLHPRMTH LSNLAFDASV   3060
WEIFLTLLNG GTLICIDYLS SLDCRALGVS ILEHQVDASV LPPALLKQCL ANVPEALASL   3120
QVLLSAGDRL DSRDAIESCA LVRGSVYNGY GPTENGIQST IYEVKADAEF VNGVPIGRAV   3180
SNSGAYVMDP QQQLVPLGVM GELVVTGDGL ARGYTDPSLD ADRFVQVSVN GQLVRAYRTG   3240
DRVRCRPCDG QIEFFGRMDR QVKIRGHRIE LAEVEHQDAA VL IAQTAENEEL   3300
VGFFTLRQTQ AVQSNGAAGV VPEHSDSELA QSCSCTQTER RVRNRLQSCL PRYMVPSRMV   3360
LLDRLPVNPN GKVDRQELTR RAQDLPISES SPVHVKPRTE LERSLCEEFA DVIGLEVGVT   3420
DNFFDLGGHS LMAMKLAARI SRRSNAHISV KDIFDHPLIA DLMKIREGS DLHTPIPHRM   3480
YVGPIQLSFA QGRLWFLDQL NLGASWYVMP LAMRLQGSLQ LDALETALFA IEQRHETLRM   3540
TFAEQDGVAV QVVHAAHYKH IKMIDKPLRQ KIDVLKMLEE ERTTPFELSR EPGWRVALLR   3600
LGDDDHVLSI VMHHIISDGW SVDVLRHELG QFYSAALRGQ DPLSQISPLP IQYRDFALWQ   3660
RQDEQVAEHQ RQLEHWTEQL ADSSPAELLS DHPRPSILSG QAGAIPVNVQ GSLYQALRAF   3720
CRAHQVTSFV VLLTAFRIAH YRLTGAEDAT IGTPIANRNR PELENMIGFF VNTQCMRIVI   3780
GSDDTFEGLV QQVRSITAAA HENQDVPFER IVSALLPGSR DTSRNPLVQL MFAVHSQRNL   3840
GQISLEGLQG ELLGVAATTR FDVEFHLFQD DDKLSGNVLF ATELFEQKTM QGMVDVFQEV   3900
LSRGLEQPQI PLATLPLTHG LEELRTMGLL DVEKTDYPRE SSVVDVFREQ AAACSEAIAV   3960
```

```
KDSSAQLTYS ELDRQSDELA GWLRQQRLPA ESLVAVLAPR SCQTIVAFLG ILKANLAYLP  4020
LDVNVPATRL ESILSAVGGR KLVLLGADVA DPGLRLADVE LVRIGDTLGR CVPGAPGDNE  4080
APVVQPSATS LAYVIFTSGS TGKPKGVMVE HRSIVRLMRH SNVSSRLLLH PRMTHLSNLA  4140
FDASVWEIFL TLLNGGTLIC IDYLSSLDCR ALGVSILEHQ VDASVLPPAL LKQCLANVPE  4200
ALASLQVLLS AGDRLDSRDA IESCALVRGS VYNGYGPTEN GIQSTIYEVK ADAEFVRGVI  4260
IGRAVSNSGA YVMDPQQQLV PLGVMGELVV TGDGLARGYT DPSLDADRFV QVSVNGQLVR  4320
AYRTGDRVRC RPCDGQIEFF GRMDRQVKIR GHRIELAEVE HAVLGLEDVQ DAAVIAFDNV  4380
DSEEPEMVGF VTITEDNPVR EDETSGQVED WANHFEISTY TDIAAIDQGS IGSDFVGWTS  4440
MYDGSEIDKA EMQEWLADTM ASMLDGQAPG NVLEIGTGTG MVLFNLGDGL QSYVGLEPSR  4500
SAAAFVNQTI KSLPTLAGNA EVHIGTATDV ARLDGLRPDL VVVNSVVQYF PSPEYLMEVV  4560
EALARLPGVE RIFFGDVRSY AINRDFLAAR ALHELGDRAT KHEIRRKMLE MEEREEELLV  4620
DPAFFTMLTS SLPGLIQHVE ILPKLMRATN ELSAYRYTAV VHVCRAGQEP RSVHTIDDDA  4680
WVNLGASRLS RPTLSSLLQT SEGASAVAVS NIPYSKTITE RALVSALDED DMQDSSDWLL  4740
AVRETGRSCS SFSATDLVEL ARETGWRVEL SWARQYSQKG ALDAVFHRHP VSAGSGRVMF  4800
QFPVETEDRP HISRTNRPLQ RLQKKRTETH VHEQLRALLP RYMVPTRIVA LDKLPVNANG  4860
KVDRQQLART AQVLPASKAP SACVAPRNEL EMTLCEEFSQ VLGVEVGITD NFFHLGGHSL  4920
MATKLAARIS HRLHTRISVK HIFDHPLIGD LSVHIADSPV PLLTITRAQH AGAVEQSFAQ  4980
ARLWFLVQLG LESPSYIIPI VLRLHGSLSK TAIEGALSAL MERHEVLRTT FEDHKGIGMQ  5040
VVQDHRHQDL VVIDVAGQGS LDYKQHLYME HVKPFDLTRD PGWRVALLRL GDDDHVLSIV  5100
MHHIISDGWS IDILLRELGQ FYSAALRGQD PLSQTSPLPI QYRDFALWQK QDHQLADHEK  5160
QLRYWEEQLA ESSPAELLCD HARPTTPSGQ AGSIPVNVQG SLYQALRAFC RAHQVTSFVV  5220
LLTAFRIAHY RLTGAEDATI GTPIANRNRP ELENMIGFFV NTQCMRIVIG SDDTFEGLVQ  5280
QVRSITAAAH ENQDVPFERI VSALLPGSRD TSRNPLVQLL FAVHAYQEVE NFAIPGVHSE  5340
LVQGTTFTRF DVEFHLLEDP DKLSGNVLFA TELFEQKTMQ GMVDVFQEVL SRGLEQPQIP  5400
LATLPLTHGL EELRTMGLLD VEKTDYPRES SVVDVFREQA AACSEAIAVK DSSAQLTYSE  5460
LDRQSDELAG WLRQQRLPAE SLVAVLAPRS CQTIVAFLGI LKANLAYLPL DVNVPATRLE  5520
SILSAVGGRK LVLLGADVAD PGLRLADVEL VRIGDTLGRC VPGAPGDNEA PVVQPSATSL  5580
AYVIFTSGST GKPKGVMVEH RSILRVVTSP PARALLPSTI IMAHLTNIAF DVSLWEICTA  5640
LLHGGTLICI QYLASLDVRG LQTTFSREAI NVAVFPPALL KTCLAKIPSA LASLSAMFSS  5700
GDRLDSRDAS EGATLVRQGI HNAYGPTENG IQSTIYEVKA DAEFVNGVPI GRAVSNSGAY  5760
VMDPQQQLVP LGVMGELVVT GDGLARGYTD PSLDADRFVQ VSVNGQLVRA YRTGDRVRCR  5820
PCDGQIEFFG RMDRQVKIRG HRIELAEVEH AILSLDYVID AAVLLRQLID QEPQVVGFVI  5880
VSTKRAYSRH NSGYASEVSA FCIKDQIAWR IRQHLCRMLP SYMVPYQIAI LDEMPINANG  5940
KVDRQNLASR TVNVQRILAA PYMAPRNEVE ISLCEQYAAL LHDVGILDD FFELGGHSLM  6000
ATRLASRISS RFSAPVSVRD IFDHPRIMDL ASIIRAGDIQ WSRILPSAYE RPVEQSFAQN  6060
RLWFLYKLDI GTTQYNLPLA IHLRGPLDIS ALFIFAFKALT ERHELLRTTF DEDDGTCLQM  6120
LLPEYQHEVR ITDLQGSHKG SLLDILNNNQ KTPFELSREP GWRVALLRLG DDDHVLSIVM  6180
HHIISDGWSV DVLRHELGQF YSAALRGQDP LSQISPLPIQ YRDFALWQRQ DEQVAEHQRQ  6240
LEHWTEQLAD SSPAELLSDH PRPSILSGQA GAIPVNVQGS LYQALRAFCR AHQVTSFVVL  6300
LTAFRIAHYR LTGAEDATIG TPIANRNRPE LENMIGFFVN TQCMRIVIGS DDTFEGLVQQ  6360
VRSITAAAHE NQDVPFERIV SALLPGSRDT SRNPLVQLMF AVHSQRNLGQ ISLEGLQGEL  6420
LGVAATTRFD VEFHLFQDDD KLSGNVLFAT ELFEQKTMQG MVDVFQEVLS RGLEQPQIPL  6480
ATLPLTHGLE ELRTMGLLDV EKTDYPRESS VVDVFREQAA ACSEAIAVKD SSAQLTYSEL  6540
DRQSDELAGW LRQQRLPAES LVAVLAPRSC QTIVAFLGIL KANLAYLPLD VNVPATRLES  6600
ILSAVGGRKL VLLGADVADP GLRLADVELV RIGDTLGRCV PGAPGDNEAP VVQPSATSLA  6660
YVIFTSGSTG KPKGVMVEHR GVVRLVKQSN VVYHLPSTSR VAHLSNLAFD ASVLEIYAAL  6720
LNGGTVYCID YLTTLDPHAL ESVFIDADLN TAVLPPALLK QVLASSPSTL HALDLLFIGG  6780
DRLDARDALY ANRLVRGSLY NVYGPTENTV LSVVYLFNDD DACINGVPIG QVVSNSGVYV  6840
MDSEQKLVPP GVMGEIVVTG DGLARGYTDS TLNTDRFVQI SVNGRVLQAY RTGDRGRYRP  6900
TDARLEFFGR LDQQIKLRGH RVELKEIEQA MLGHNAVDDA GVVALEISEC QELEMVGFVT  6960
LRNLGTMEAT NNLAHTSWNP VTLKTPLASQ IVAEVRGRLQ RNLPLYMVPA TIVVLHTMPV  7020
NANGKLDRQA LVKAAMTLPK TAPLVWMAPR NEGETSLCEE LTDILGVNVG ITDNFFDLGG  7080
HSLLATRVAA RISRRLDALV TVKQIFDHPV IGDLAAAIQG GSVRHLPITA SEVDGPVQQS  7140
FAQNRLWFLE QMNIGATWYI VPLAVRLYGT LRVEALNIAL RTIQQRHETL RTTFEELNGI  7200
AVQRCDSTCQ GQLRVDLVG QGPDRYREIL DVQQTTPFEL SQEPGWRVAL LRLGDDDHVL  7260
SIVMHHIISD GWSVDVLLRE IGQFYSAALR GQDPLSQISP LPIQYRDFAL WQRQDEQVAE  7320
HQRQLEHWTE QLADSSPAEL LSDHPRPSIL SGQAGAIPVN VQGSLYQALR AFCRAHQVTS  7380
FVVLLTAFRI AHYRLTGAED ATIGTPIANR NRPELENMIG FFVNTQCMRI VIGSDDTFEG  7440
LVQQVRSITA AAHENQDVPF ERIVSALLPG SRDTSRNPLV QLMFAVHSQR NLGQISLEGL  7500
QGELLGVAAT TRFDVEFHLF QDDDKLSGNV LFATELFEQK TMQGMVDVFQ EVLSRGLEQP  7560
QIPLATLPLT HGLEELRTMG LLDVEKTDYP RESSVVDVFR EQAAACSEAI AVKDSSAQLT  7620
YSELDRQSDE LAGWLRQQRL PAESLVAVLA PRSCQTIVAF LGILKANLAY LPLDVNVPAT  7680
RLESILSAVG GRKLVLLGAD VADPGLRLAD VELVRIGDTL GRCVPGAPGD NEAPVVQPSA  7740
TSLAYVIFTS GSTGKPKGVM VEHRGVVRLV KQSNVVYHLP STSRVAHLSN LAFDASAWEI  7800
YAALLNGGTL ICIDYFTTLD CSALGAKFIK EKIVATMIPP ALLKQCLAIF PTALSELVLL  7860
FAAGDRFSSG DAVEVQRHTK GAVCNAYGPT ENTILSTIYE VKQNENFPNG VPIGRAVSNS  7920
GAYVMDPQQQ LVPLGVMGEL VVTGDGLARG YTDPSLDADR FVQVSVNGQL VRAYRTGDRV  7980
RCRPCDGQIE FFGRMDRQVK IRGHRIELAE VEHAVLGLED VQDAAVIAFD NVDSEEPEMV  8040
GFVTITEDNP VREDETSGQV EDWANHFEIS TYTDIAAIDQ GSIGSDFVGW TSMYDGSEID  8100
KAEMQEWLAD TMASMLDGQA PGNVLEIGTG TGMVLFNLGD GLQSYVGLEP SRSAAAFVNQ  8160
TIKSLPTLAG NAEVHIGTAT DVARLDGLRP DLVVVNSVVQ YFPSPEYLME VVEALARLPG  8220
VERIFFGDVR SYAINRDFLA ARALHELGDR ATKHEIRRKM LEMEEREEEL LVDPAFFTML  8280
TSSLPGLIQH VEILPKLMRA TNELSAYRYT AVVHVCRAGQ EPRSVHTIDD DAWVNLGASR  8340
LSRPTLSSLL QTSEGASAVA VSNIPYSKTI TERALVSALD EDDMQDSSDW LLAVRETGRS  8400
CSSFSATDLV ELARETGWRV ELSWARQYSQ KGALDAVFHR HPVSAGSGRV MFQFPVETED  8460
RPHISRTNRP LQRLQKKRTE THVHEQLRAL LPRYMVPTRI VALDKLPVNA NGKVDRQQLA  8520
RTAQVLPASK APSACVAPRN ELEMTLCEEF SQVLGVEVGI TDNFFHLGGH SLMATKFAAR  8580
ISRRLNAIVS VKNVFDHPVP MDLAATIQEG SKLHTPIPRT AYSGPVEQSF AQGRLWFLDQ  8640
FNPSSIGYVM PFAARLHGQL QIEALTAALF ALEQRHEILR TTLDAHDGVG MQIVHAEHPQ  8700
```

```
QLRIIDVSAK ASSSYAQTLR DEQASPFDLS KEPGWRVSLL QLSEIDYVLS IVMHHTIYDG    8760
WSLDVLRREL SQFYAAAIRG REPLSTIEPL PIQYRDFSVW QKQEDQVAEH RRQLHYWIEQ    8820
LDGSSPAEFL NDKPRPTLLS GKAGVVEIAV KGTVYQRLLE FCRLHQVTSF MVLLAAFRAT    8880
HYRLTGTEDA TVGTPIANRN RPELENMIGL FVNTQCIRLK IEDNDTLEEL VQHVRATITA    8940
SISNQDVPFE QVVSALLPGS RDTSRNPLVQ LTFAVHSQRN LADIQLENVE TNAMPICPST    9000
RFDAEFHLFQ EENMLSGRVL FSDDLFEQKT MQGMVDVFQE VLSRGLEQPQ IPLATLPLTH    9060
GLEELRTMGL LDVEKTDYPR ESSVVDVFRE QAAACSEAIA VKDSSAQLTY SELDRQSDEL    9120
AGWLRQQRLP AESLVAVLAP RSCQTIVAFL GILKANLAYL PLDVNVPATR LESILSAVGG    9180
RKLVLLGADV ADPGLRLADV ELVRIGDTLG RCVPGAPGDN EAPVVQPSAT SLAYVIFTSG    9240
STGKPKGVMV EHRGVVRLVK QSNVVYHLPS TSRVAHLSNL AFDASAWEIY AALLNGGTLI    9300
CIDYFTIIDA RALGVIFAQQ SINATMLSPL LLKQFLSDAP FVLRSLHALY LGGDRLQGRD    9360
AIQACRVGCA FVINAYGPTE NSVISTTYTL VKGNADFPNG VPIGRAVSNS GAYVMDPQQQ    9420
LVPLGVMGEL VVTGDGLARG YTDPSLDADR FVQVSVNGQL VRAYRTGDRV RCRPCDGQIE    9480
FFGRMDRQVK IRGHRIELAE VEHAVLGLED VQDAAVLIAQ TAENEELVGF FTLRQTQAVQ    9540
SNGAAGVVPE HSDSELAQSC SCTQTERRVR NRLQSCLPRY MVPSRMVLLD RLPVNPNGKV    9600
DRQELTRRAQ DLPISESSPV HVKPRTELER SLCEEFADVI GLEVGVTDNF FDLGGHSLMA    9660
MKLAARISRR SNAHISVKDI FDHPLIADLA MKIREGSDLH TPIPHRMYVG PIQLSFAQGR    9720
LWFLDQLNLG ASWYVMPLAM RLQGSLQLDA LETALFAIEQ RHETLRMTFA EQDGVAVQVV    9780
HAAHYKHIKM IDKPLRQKID VLKMLEEERT TPFELSREPG WRVALLRLGD DDHVLSIVMH    9840
HIISDGWSVD VLRHELGQFY SAALRGQDPL SQISPLPIQY RDFALWQRQD EQVAEHQRQL    9900
EHWTEQLADS SPAELLSDHP RPSILSGQAG AIPVNVQGSL YQALRAFCRA HQVTSFVVLL    9960
TAFRIAHYRL TGAEDATIGT PIANRNRPEL ENMIGFFVNT QCMRIVIGSD DTFEGLVQQV   10020
RSITAAAHEN QDVPFERIVS ALLPGSRDTS RNPLVQLMFA VHSQRNLGQI SLEGLQGELL   10080
GVAATTRFDV EFHLFQDDDK LSGNVLFATE LFEQKTMQGM VDVFQEVLSR GLEQPQIPLA   10140
TLPLTHGLEE LRTMGLLDVE KTDYPRESSV VDVFREQAAA CSEAIAVKDS SAQLTYSELD   10200
RQSDELAGWL RQQRLPAESL VAVLAPRSCQ TIVAFLGILK ANLAYLPLDV NVPATRLESI   10260
LSAVGGRKLV LLGADVADPG LRLADVELVR IGDTLGRCVP GAPGDNEAPV VQPSATSLAY   10320
VIFTSGSTGK PKGVMVEHRG VVRLVKQSNV VYHLPSTSRV AHLSNLAFDA SAWEIYAALL   10380
NGGTLICIDY FTTLDCSALG AKFIKEKIVA TMIPPALLKQ CLAIFPTALS ELVLLFAAGD   10440
RFSSGDAVEV QRHTKGAVCN AYGPTENTIL STIYEVKQNE NFPNGVPIGR AVSNSGAYVM   10500
DPQQQLVPLG VMGELVVTGD GLARGYTDPS LDADRFVQVS VNGQLVRAYR TGDRVRCRPC   10560
DGQIEFFGRM DRQVKIRGHR IELAEVEHAV LGLEDVQDAA VIAFDNVDSE EPEMVGFVTI   10620
TEDNPVREDE TSGQVEDWAN HFEISTYTDI AAIDQGSIGS DFVGWTSMYD GSEIDKAEMQ   10680
EWLADTMASM LDGQAPGNVL EIGTGTGMVL FNLGDGLQVS VGLEPSRSAA AFVNQTIKSL   10740
PTLAGNAEVH IGTATDVARL DGLRPDLVVV NSVVQYFPSP EYLMEVVEAL ARLPGVERIF   10800
FGDVRSYAIN RDFLAARALH ELGDRATKHE IRRKMLEMEE REEELLVDPA FFTMLTSSLP   10860
GLIQHVEILP KLMRATNELS AYRYTAVVHV CRAGQEPRSV HTIDDDAWVN LGASRLSRPT   10920
LSSLLQTSEG ASAVAVSNIP YSKTITERAL VSALDEDDMQ DSSDWLLAVR ETGRSCSSFS   10980
ATDLVELARE TGWRVELSWA RQYSQKGALD AVFHRHPVSA GSGRVMFQFP VETEDRPHIS   11040
RTNRPLQRLQ KKRTETHVHE QLRALLPRYM VPTRIVALDK LPVNANGKVD RQQLARTAQV   11100
LPASKAPSAC VAPRNELEMT LCEEFSQVLG VEVGITDNFF HLGGHSLMAT KLAARISRQL   11160
NIQVSVRDIF DYPVIVDLTD RLRLHHTRIL THDHGQHGQP DLKPFTLLPT NNPQEFLQHH   11220
ILPQLVPDHA KILDVYPVTR IQRRFLHHPK RGLPRFPSMV FFDFPPGSDP HKLRLACMAL   11280
VQRFDILRTI FLSVSGQFFQ VVLDGYGIVI PVIEVDEELD DATRKLHDSD IQQPLRLGKP   11340
LIRIAVLKRQ HSRVRAVLRL SHALYDGLSF EHIIQSLHAL YLDITLSAPP KFGLYVQHMI   11400
QSRAEGYAFW RSVLKGSSMT ILERSSTLQS RQPHLGRFLS AEKIIKAPLH ANKSGITQAT   11460
VFAAANALML ANLTGTNDVV FARIVSGRQS LPKNFQHVVG PCTNDVPVRV RMEPGVGPKA   11520
LLRQVQDQYV HSFPPETLGF DEIKENCTDW PERITNFGCS TTYQNFDIFP KSQIDHQQIQ   11580
MASLASEYQN RETWDEAPLY DLNVTGVPQP DGRHIKIYVG VDGQLCDEST LDCILSDICE   11640
GVVSLTDALQ ELPAASITE                                                11659
```

METHODS FOR FERMENTATIVE PRODUCTION OF MASSOIA LACTONE

CROSS-REFERENCE TO RELATED APPLICATIONS

The present application is a division of U.S. patent application Ser. No. 16/712,672 filed on 12 Dec. 2019, now U.S. Pat. No. 11,639,492, which is a division of U.S. patent application Ser. No. 15/750,584, filed on 6 Feb. 2018, now abandoned, which is a national stage filing under 35 U.S.C. § 371 of PCT/SG2016/050395, filed on 16 Aug. 2016, which is related to and claims the benefit of priority to U.S. Provisional patent application Ser. No. 62/205,996 filed 17 Aug. 2015, the disclosures of which are incorporated herein by reference in their entireties.

REFERENCE TO AN ELECTRONIC SEQUENCE LISTING

The contents of the electronic sequence listing (2577-249US4.xml; Size: 98,304 bytes; and Date of Creation: Jul. 27, 2023) are herein incorporated by reference in their entireties.

BACKGROUND OF THE INVENTION

The present invention relates to the field of fermentation biotechnology, more particularly to methods for the fermentative production of *Massoia* lactone by *Aureobasidium* species.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

C-10 *Massoia* lactone [C-10 (5,6-dihydro-6-pentyl-2H-pyran-2-one)] and C-12 *Massoia* lactone [C-12 (5,6-dihydro-6-heptyl-2H-pyran-2-one)] are the major constituent of bark oil of *Massoia* (*Cryptocarya Massoia*) [1]. *Massoia* lactones can also be found in cane sugar molasses, cured tobacco and the essential oil of Sweet Osmanthus (*Osmanthus fragrans*) and jasmine [2]. At 20 ppm, it has a taste described as creamy, coconut, green and slightly fruity. *Massoia* bark oil is used in the flavor industry as an additive in butter and milk flavors (international FEMA code 3744). Current global supply of *Massoia* bark oil comes from Indonesia, using primitive and costly extraction process that destroy precious native forest.

*Massoia* lactone is the substrate for the production of saturated delta-decanolide or delta-dodecanolide, which is the key molecule for peach flavor. It can be made by biohydrogenation using a wide range of microorganisms, e.g., yeast (*Saccharomyces, Candida, Pichia*), molds (*Cladosporium*), and bacteria (*Pseudomonas, Sarcina*), [3,4].

Although methods for the chemical synthesis of *Massoia* lactone have been available, the process is a rather complicated and requires multi-step reactions using costly raw materials and catalysts [5]. Previously, *Massoia* lactone was found in the alkali-hydrolyzed glycolipid secreted by *Aureobasidium* pullalan A-21 that was cultured under a calcium-deficient condition. It has been reported that, in the presence of calcium, polymalic acid was produced instead [6]. The interaction between various trace elements on the production of *Massoia* lactone has not been reported.

Certain strains of *A. pullulans* are known to produce extracellular "heavy oils", or polyol lipids, when $CaCO_3$ is not present in the medium. The oils have been described as 3,5-dihydroxydecanoyl and 5-hydroxy-2-decenoyl esters of arabitol and mannitol. Medium for oil production is composed of 50 g/l sucrose, 0.6 g/l (w/v) peptone, 0.4 g/l yeast extract, 5 g/l $K_2HPO_4$, 0.4% g/l $MgSO_4*7H_2O$, and 1 g/l NaCl [7]. Another reported medium uses nitrate as the sole nitrogen source with low phosphate content and is composed of 120 g/l glucose, 1.5 g/l $NaNO_3$, 1 g/l $KNO_3$, 0.05 g/l $KH_2PO_4$, 0.2 g/l $MgSO_4*7H_2O$, 2 ppm $ZnSO_4*7H_2O$, and 0.2 g/l yeast extract [6].

It is desired to develop new fermentation methods for the production of *Massoia* lactone.

SUMMARY OF THE INVENTION

The present invention relates to the field of fermentation biotechnology, more particularly to methods for the fermentative production of *Massoia* lactone by *Aureobasidium* species.

In one aspect, the present invention provides a method for the fermentative production of *Massoia* lactone by *Aureobasidium* species. In one embodiment, the *Aureobasidium* species is *Aureobasidium melanogenum*. In another embodiment, the *A. melanogenum* is a strain of *A. melanogenum* that does not express a functional Aureobasidin A (AbA) biosynthesis complex (aba1) gene mRNA when cultured. In one embodiment, the functional mRNA is not expressed in the culture medium described herein. In a further embodiment, the *A. melanogenum* that does not express a functional aba1 gene mRNA when cultured is the W5-2 strain of *A. melanogenum* as described herein. In one embodiment, the *Aureobasidium* species described herein is cultured in a culture medium described in further detail herein to produce a fermentation product containing *Massoia* lactone. In one embodiment, the culturing is performed for about 4 days to about 12 days, preferably for about 5 days to about 12 days, more preferably for about 7 days to about 10 days. In another embodiment, the culturing is performed at about 25° C. to about 35° C., preferably about 28° C. to about 32° C. In some embodiments, the *Massoia* lactone is purified from the fermentation product using conventional techniques and/or as described in further detail herein.

In a second aspect, the present invention provides a culture medium for the fermentative production of *Massoia* lactone. In one embodiment, the culture medium comprises high levels of phosphate ions, ammonium ions and calcium ions as described in further detail herein. In some embodiments, the culture medium comprises $KH_2PO_4$, $Na_2HPO_4$, $(NH4)_2SO_4$, $MgSO_4$ and $CaCl_2$. In another embodiment, the culture medium further comprises at least two trace elements as described in further detail herein. In some embodiments, the trace elements may be selected from $Fe^{2+}$, $Cu^{2+}$, $Zn^{2+}$ and $MoO_4^{2-}$. In other embodiments, each trace element that may be present in the culture medium may be present in an amount from about 0.1 µM to about 1.0 mM. In a further embodiment, the culture medium comprises urea as a nitrogen source. In another embodiment, the culture medium comprises glucose, mannose, xylose or mixtures thereof as a carbon source. In one embodiment, glucose is used as the sole carbon source. In one embodiment, the culture medium has a pH from about 5.5 to about 6.5, preferably about 6.0. The fermentation method produces high levels of glycolipids. Biochemically, hydroxyl fatty acids conjugate to produce sugars and eventually produce *Massoia* lactone. Thus, the method produces high levels of *Massoia* lactone—a commercially desirable feature of the present invention.

In a third aspect, the present invention provides a novel strain of *A. melanogenum* designated W5-2. In some embodiments, *A. melanogenum* W5-2 does not express a functional Aureobasidin A biosynthesis complex gene mRNA when cultured. In one embodiment, a functional mRNA is not expressed in the culture medium described herein. In other embodiments, *A. melanogenum* W5-2 has been deposited with the Agricultural Research Culture Collection (NRRL), 1815 N. University Street, Peoria, Illinois 61604, USA on 28 May 2015 and assigned accession number NRRL 67063.

BRIEF DESCRIPTION OF THE FIGURES

FIGS. 3A-3D show the characterization of Nile Red staining substance in W5-2 cells. Cell were cultured in HMDC medium with 10% glucose in shaking flasks for 5 day. Cells were stained with Nile Red and imaged by Confocal microscopy. FIG. 3A: Red channel. FIG. 3B: bright field image. FIG. 3C: Over-lay of FIG. 3A and FIG. 3B. Scale bar=10 µM. FIG. 3D: TLC image of total ethyl acetate extract. The positions for triacylglyceride (TAG) and glycolipid are indicated on the right.

FIG. 4A: GCMS spectra of methanol-esterified products of methanol and chloroform extract of freeze-dried cell biomass. Arrows indicate the peaks for major fatty acid methyl esters and *Massoia* lactone. FIG. 4B: Database search and the comparison of MS spectrum of the peak shown in upper panel to that of standard *Massoia* lactone, 6-Pentyl-5,6-dihydro-2H-pyran-2-one, shown in lower panel.

FIG. 7A: Factorial Design was used to evaluate the effects of FeSO4, MnSO4, ZnSO4, CuCl2 and AlCl3. Run #6 (T2) and Run #12 (T3) were selected for further optimization. FIG. 7B: Factorial Design was used to evaluate the effects of H3BO4, CoCl2 and NaMoO4 based on Medium 2 of step 5.

FIG. 9A: *Massoia* lactone. FIG. 9B: Dry biomass yield. FIG. 9C: Residual $NH_4^+$ in the medium.

FIGS. 12A-12C show production of *Massoia* lactone. FIG. 12A: GCMS chromatograph of W5-2 Sample cultured in R15 Medium in shake flask. FIG. 12B: GCMS chromatograph of W5-2 Sample cultured in T3 medium in 2 L fermenter. FIG. 12C: database search of ML *Massoia* lactone peak of (FIG. 12B).

DETAILED DESCRIPTION OF THE INVENTION

Figure 1:
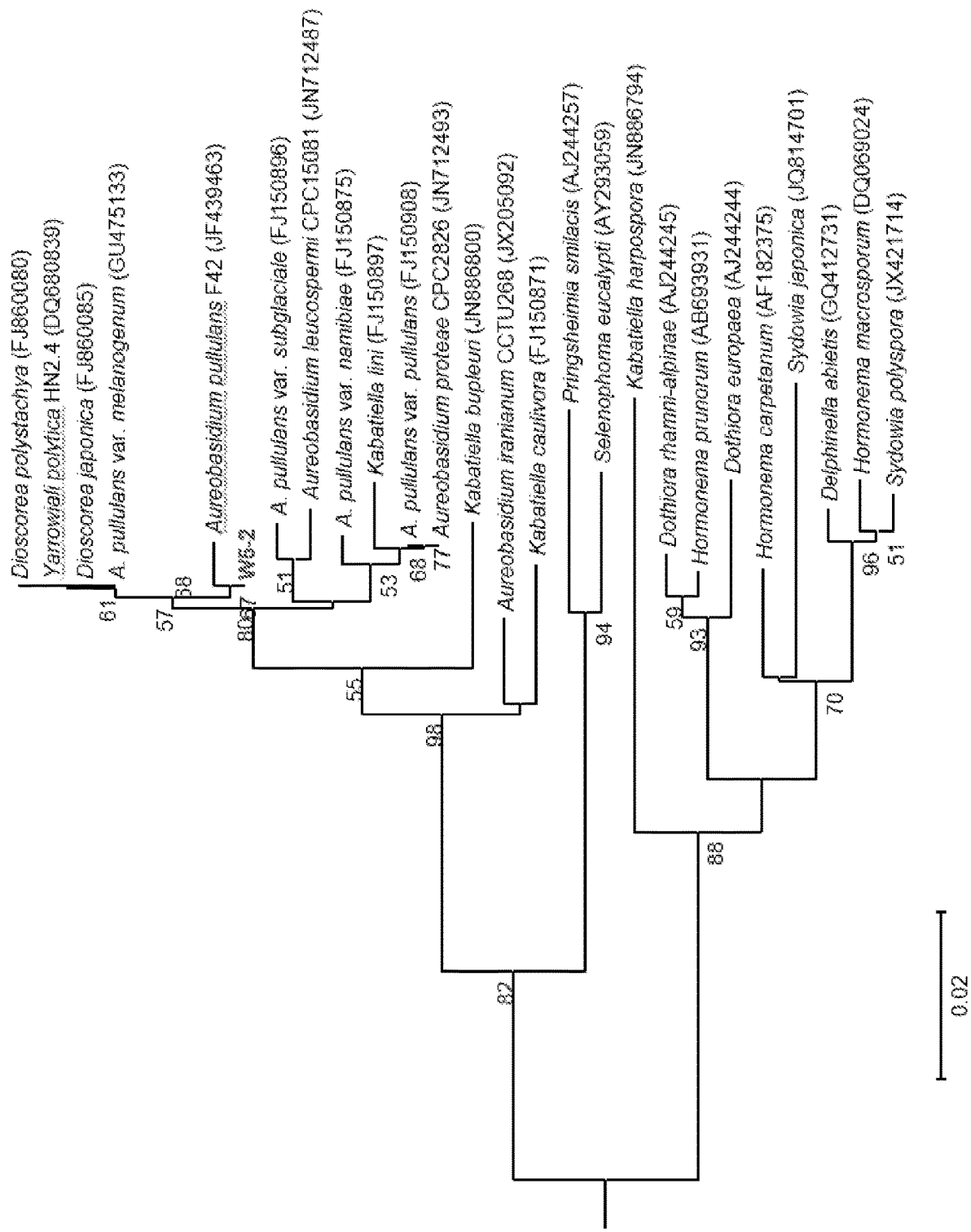
FIG. 1 shows a phylogenetic dendrogram, based on 18S rRNA gene, the first internal transcribed spacer (ITS1), the 5.8S rRNA gene, the second ITS region and the 5' end of the 28S rRNA gene sequences and constructed from evolutionary distances, showing the position of *Aureobasidium* strain W5-2 within the radiation of members of the family Dothioraceae, order Dothideales [36]. Numbers at branching points refer to bootstrap percentages (based on 1000 resamplings); only values above 50% are shown. GenBank accession number of each sequence is shown in parentheses.

The present invention relates to the field of fermentation biotechnology, more particularly to methods for the fermentative production of *Massoia* lactone by *Aureobasidium* species.

Unless defined otherwise, all technical and scientific terms used herein have the same meaning as is commonly understood by one of skill in the art to which the invention belongs.

The term "about" or "approximately" means within a statistically meaningful range of a value. Such a range can be within an order of magnitude, preferably within 50%, more preferably within 20%, more preferably still within 10%, and even more preferably within 5% of a given value or range. The allowable variation encompassed by the term "about" or "approximately" depends on the particular system under study, and can be readily appreciated by one of ordinary skill in the art.

The term "as described in further detail herein" means the description of the embodiments set forth in the detailed description of the invention and in the Examples. In this context, the Examples comprise additional details of the general nature of the invention, as well as certain specific aspects not found elsewhere in the specification.

The term "*Massoia* lactone" as used herein means C-10 *Massoia* lactone [C-10 (5,6-dihydro-6-pentyl-2H-pyran-2-one)] and/or C-12 *Massoia* lactone [C-12 (5,6-dihydro-6-heptyl-2H-pyran-2-one)].

The term "*Aureobasidium melanogenum* W5-2" or "*A. melanogenum* W5-2" or "W5-2" refers to a novel strain of *A. melanogenum* isolated and characterized as described herein and a culture of which has been deposited as described herein.

In one aspect, the present invention provides a method for the fermentative production of *Massoia* lactone by *Aureobasidium* species. In one embodiment, the *Aureobasidium* species is *Aureobasidium melanogenum*. In another embodiment, the *A. melanogenum* is a strain of *A. melanogenum* that does not express a functional Aureobasidin A (AbA) biosynthesis complex (aba1) gene mRNA when cultured. In one embodiment, the functional mRNA is not expressed in the culture medium described herein. The sequence of a functional aba1 gene is set forth in Genbank Accession No. EU886741 (SEQ ID NO:5). In a further embodiment, the *A. melanogenum* that does not express a functional aba1 gene mRNA when cultured is the W5-2 strain of *A. melanogenum* as described herein. In one embodiment, the *Aureobasidium* species described herein is cultured in a culture medium described in further detail herein to produce a fermentation product containing *Massoia* lactone. In one embodiment, the culturing is performed for about 4 days to about 12 days, preferably for about 5 days to about 12 days, preferably for about 5 days to about 11 days, preferably for about 6 days to about 11 days, more preferably for about 7 days to about 10 days. In another embodiment, the culturing is performed at about 25° C. to about 35° C., preferably at about 27° C. to about 32° C., more preferably at about 28° C. to about 32° C. In a further embodiment, the culturing is performed in shake flasks agitated with a speed from about 175 rpm to about 225 rpm, preferably about 200 rpm. In some embodiments, the *Massoia* lactone is purified from the fermentation product using conventional techniques and/or as described in further detail herein.

In some embodiments, the *Massoia* lactone is purified from the fermentation product using conventional techniques, e.g., by alkaline hydrolysis and solvent extraction [6]. In other embodiments, a strong inorganic acid is added to the fermentation product to hydrolyze the fermentation product. In one embodiment, the strong organic acid is sulfuric acid or hydrochloric acid. In a further embodiment, the *Massoia* lactone is purified by solvent extraction or distillation. In some embodiments, the solvent is ethyl acetate or hexane.

In a second aspect, the present invention provides a culture medium for the fermentative production of *Massoia* lactone. In one embodiment, the culture medium comprises high levels of phosphate ions, ammonium ions and calcium ions as described in further detail herein. In some embodiments, the culture medium comprises $KH_2PO_4$, $Na_2HPO_4$, $(NH_4)_2SO_4$, $MgSO_4$ and $CaCl_2$. In some embodiments, the culture medium comprises about 10.0 g/l to about 15 g/l, preferably about 12.5 g/l $KH_2PO_4$, about 0.5 g/l to about 2.0 g/l, preferably about 1.0 g/l $Na_2HPO_4$, about 3.5 g/l to about 6.5 g/l, preferably about 5.0 g/l $(NH_4)_2SO_4$, about 1.0 g/l to about 4.0 g/l, preferably about 2.5 g/l $MgSO_4 \cdot 7H_2O$ and about 0.10 g/l to about 0.40 g/l, preferably about 0.25 g/l $CaCl_2 \cdot 2H_2O$. In another embodiment, the culture medium further comprises at least two trace elements. In a further embodiment, the culture medium comprises at least three trace elements. In an additional embodiment, the culture medium comprises four trace elements. In some embodiments, the trace elements may be selected from $Fe^{2+}$, $Cu^{2+}$, $Zn^{2+}$ and $MoO_4^{2-}$. In other embodiments, each trace element that may be in the culture medium may be present in an amount from about 0.1 µM to about 1.0 mM, from about 1.0 µM to about 1.0 mM, from about 10.0 µM to about 1.0 mM, or from about 100 µM to about 1.0 mM. In a further embodiment, the culture medium comprises urea or ammonium as a nitrogen source. In some embodiments, the urea is present in the culture medium in an amount from about 1.5 g/l to about 2.5 g/l, preferably from about 1.8 g/l to about 2.2 g/l, more preferably about 2 g/1. In some embodiments, ammonium is present in the culture medium in an amount to provide the same amount of nitrogen as provided by the noted urea amounts. In another embodiment, the culture medium comprises glucose, mannose, xylose or mixtures thereof as a carbon source. In some embodiments, the carbon source is present in the culture medium in an amount from about 4% to about 12%, preferably from about 5% to about 12%, preferably from about 5% to about 11%, more preferably from about 5% to about 10%. In some embodiments, glucose is the sole carbon source. In one embodiment, the culture medium has a pH from about 5.5 to about 6.5, preferably about 6.0.

In a third aspect, the present invention provides a novel strain of *A. melanogenum* designated W5-2, including a pure culture of the novel strain or the isolated novel strain or the isolated and biologically pure culture of the novel strain. In some embodiments, *A. melanogenum* W5-2 does not express a functional Aureobasidin A synthase gene mRNA when cultured. In one embodiment, the functional mRNA is not expressed in the culture medium described herein. In other embodiments, *A. melanogenum* W5-2 was deposited on 28 May 2015 under terms of the Budapest Treating with the Agricultural Research Culture Collection (NRRL) located at 1815 N. University Street, Peoria, Illinois 61604, USA and assigned Accession Number NRRL 67063.

In some embodiments, *Aureobasidium melanogenum* and/or *Aureobasidium melanogenum* strain W5-2 is characterized by the sequence of its genome. In one embodiment, the *Aureobasidium melanogenum* GDP1 genomic sequence shares at least 97.5% identity over at least 98.5% of SEQ ID NO:2, preferably 99%-100% identity to over at least 98% of SEQ ID NO:2. In another embodiment, the *Aureobasidium melanogenum* TEF1A genomic sequence shares at least 98% identity over at least 94% of SEQ ID NO:8, preferably 99%-100% identity to over at least 99% of SEQ ID NO:8. In an additional embodiment, the *Aureobasidium melanogenum* RBP1 genomic sequence shares at least 91% identity over at least 92% of SEQ ID NO:10, preferably 96%-100% identity to over at least 98% of SEQ ID NO:10. In a further embodiment, the *Aureobasidium melanogenum* GDP1 genomic sequence shares at least 97.5% identity over at least 98.5% of SEQ ID NO:2, preferably 99%-100% identity to over at least 98% of SEQ ID NO:2, the *Aureobasidium melanogenum* TEF1A genomic sequence shares at least 98% identity over at least 94% of SEQ ID NO:8, preferably 99%-100% identity to over at least 99% of SEQ ID NO:8 and the *Aureobasidium melanogenum* RBP1 genomic sequence shares at least 91% identity over at least 92% of SEQ ID NO:10, preferably 96%-100% identity to over at least 98% of SEQ ID NO:10.

In other embodiments, the *Aureobasidium melanogenum* and/or *Aureobasidium melanogenum* strain W5-2 is characterized by the amount of fatty acids stored in the fungal cells. In one embodiment, the *Aureobasidium melanogenum* and/or *Aureobasidium melanogenum* strain W5-2 fungal cells can store fatty acids at about 40% of its dry weight.

In accordance with the present invention, it has surprisingly been found that the fermentation of *A. melanogenum* W5-2 in the culture medium that contains all of the components described herein for the culture medium produces a very high yield of *Massoia* lactone. For example, as shown in the Examples, batch fermentation of *A. melanogenum* W5-2 in this culture medium produced *Massoia* lactone at a 7 day peak of 10.268 g/l in a 2 L bioreactor, with a volume productivity of 61.11 mg/hr/l. Thus, in one embodiment, the batch fermentation of *A. melanogenum* W5-2 in this culture medium yields 10.268 g/l of crude *Massoia* lactone. In another embodiment, the batch fermentation of *A. melanogenum* W5-2 in this culture medium yields more than 10 g/l of crude *Massoia* lactone. In some embodiments, the yield of crude *Massoia* lactone is at least 11 g/l, or at least 12 g/l, or at least 13 g/l, or at least 14 g/l or at least 15 g/l. In other embodiments, the yield of crude *Massoia* lactone is from about 10 g/l to about 25 g/l, or from about 10 g/l to about 24 g/l, or from about 10 g/l to about 23 g/l, or from about 10 g/l to about 22 g/l, or from about 10 g/l to about 21 g/l, or from about 10 g/l to about 20 g/l, or from about 10 g/l to about 19 g/l, or from about 10 g/l to about 18 g/l, or from about 10 g/l to about 17 g/l, or from about 10 g/l to about 16 g/l, or from about 10 g/l to about 15 g/l, or from about 10 g/l to about 14 g/l.

In some embodiments, the yield of purified *Massoia* lactone from the crude extract is at least 50%. In other embodiments, the yield of purified *Massoia* lactone from the crude extract is more than 5 g/l. In some embodiments, the yield of purified *Massoia* lactone from the crude extract is at least 5.5 g/l, or at least 6 g/l, or at least 6.5 g/l, or at least 7 g/l or at least 7.5 g/l. In other embodiments, the yield of purified *Massoia* lactone from the crude extract from about 5 g/l to about 12.5 g/l, or from about 5 g/l to about 12 g/l, or from about 5 g/l to about 11.5 g/l, or from about 5 g/l to about 11 g/l, or from about 5 g/l to about 10.5 g/l, or from about 5 g/l to about 10 g/l, or from about 5 g/l to about 9.5 g/l, or from about 5 g/l to about 9 g/l, or from about 5 g/l to about 8.5 g/l, or from about 5 g/l to about 8 g/l, or from about 5 g/l to about 7.5 g/l, or from about 10 g/l to about 7 g/l.

It has surprisingly been found that the fermentation method using strain W5-2, as described herein, has several advantages.

The method produces high levels of glycolipids. Biochemically hydroxyl fatty acids conjugate to produce sugars and eventually produce *Massoia* lactone. Thus, the method produces high levels of *Massoia* lactone—a commercially desirable feature of the invention.

*Massoia* lactone is exuded into the medium and about 80% of the supernatant contains *Massoia* lactone—reflecting the ability to obtain high amounts of *Massoia* lactone.

The method can produce more than 10 g/l *Massoia* lactone within 5 days at lab scale using glucose as a sole carbon source.

The crude extract has more than 10 g/l of *Massoia* lactone. Upon purification the yield is more than 5 g/l of the crude extract, which is at least about 50% distillation recovery.

Use of 2 liter bioreactor yields high amounts of *Massoia* lactone.

The method is highly efficient—the crude extract has less of impurities, including negligible or minimum intermediates. The method is highly time and cost efficient.

The *Massoia* lactone is capable of producing multiple odors and/or flavorsflavors, e.g., coconut, waxy, oily aroma, creamy, green and slightly fruity flavors and/or odors. The *Massoia* lactone can be converted into delta-decanolide or delta-dodecanolide to produce a peachy flavor and/or odor.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, New York); Sambrook et al., 1989, Molecular Cloning, 2nd Ed. (Cold Spring Harbor Laboratory Press, Cold Spring Harbor, New York); Sambrook and Russell, 2001, *Molecular Cloning*, 3rd Ed. (Cold Spring Harbor Laboratory Press, Cold Spring Harbor, New York); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, Antibodies, (Cold Spring Harbor Laboratory Press, Cold Spring Harbor, New York); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols* (*Methods in Molecular Biology*), Human Press, Totowa, N J, 2004; Sohail, *Gene Silencing by RNA Interference: Technology and Application*, C R C, 2004.

EXAMPLES

The present invention is described by reference to the following Examples, which are offered by way of illustration and are not intended to limit the invention in any manner. Standard techniques well known in the art or the techniques specifically described below were utilized.

Example 1

Materials and Methods

Isolation of microbial strains: Microbial samples were collected from various regions in Singapore. Samples were mixed with 100 ml autoclaved sea water and incubated overnight at 28° C. A 100 μl of the overnight culture was withdrawn and streaked on modified seawater-YPD (Yeast Peptone Dextrose) medium (containing 1 g/l peptone, 2 g/l yeast extract, 4 g/l glucose, and 8 g/l agar, pH 7), which was further supplemented with 0.5 μg/ml Nile red and an antibiotic selected from ampicillin (25 μg/ml), kanamycin (25 μg/ml) and streptomycin (100 μg/ml). Potato dextrose agar (PDA) was also used for the initial screening. The plates were incubated at 28° C. for 48 hr and the strongly Nile red staining strains were identified by examining the plates under a Nikon C-DSS230 stereomicroscope microscope (Nikon, Japan) equipped with Digital Sight DS-L1 camera. Candidate strains were purified by 2 rounds of single colony isolation on seawater-YPD plates followed by verification of Nile red staining in small scale liquid cultures. Florescence was measured using the TECAN infinite M200 fluorometer with the excitation wave-length and emission wave-length set at of 530 nm and 575 nm respectively (TECAN, USA).

Phylogenetic analysis of the microbial strains by ITS sequencing: Yeast isolates were cultured in YPD medium at 30° C. Genomic DNAs were extracted from 2 ml of 48 hr cultures using the MasterPure™ Yeast DNA Purification Kit (Epicentre Biotechnologies, USA) according to the manufacturer's instructions. PCR amplification reactions were performed in 40 µl 1× buffer with 2.5 mM dNTP, 50 µM each primer, 50 ng of total DNA and 3 units of Taq DNA polymerase (i-DNA Biotechnology, Singapore). PCR cycling conditions were as followed: 95° C./10 min, 30 cycles of 95° C./1 min, 61.8° C./1 min and 72° C./1 min and final extension for 5 min/72° C. The ITS1(5'-tccgtaggt-gaacctgcgg; SEQ ID NO:3) and ITS4 (5'-tcctccgcttattgatatgc SEQ ID NO:4) [8] primers were used to amplify the ITS region of the nuclear rRNA operon spanning the 3' end of the 18S rRNA gene, the first internal transcribed spacer (ITS1), the 5.8S rRNA gene, the second ITS region and the 5' end of the 28S rRNA gene. [9]. Gel-purified PCR products were sequenced with the Big-Dye sequencing method in Applied Biosystems 3730xl DNA Analyzer (Life technologies, USA). Sequences were analyzed by BLAST against the NCBI database and aligned using the CLUSTAL W tool in MEGA version 5.05 [10]. Phylogenetic analyses were performed by the Neighbour-Joining [11], Maximum-Likelihood [12] and Maximum-Parsimony methods [13] using the MEGA version 5.05 with the bootstrap values set at 1000 replications.

Small scale culture and fed-batch fermentation: *Aureobasidium* strain W5-2 was cultured in 100 ml liquid medium in 250 ml shake flasks, agitated with a speed of 200 rpm and constant temperature of 30° C. The High Density Culture Medium (HDCM) developed for *Rhodotorula glutinis* [14] was used as the basic culture medium. It contains 90 g/l glucose, 12.5 g/l $KH_2PO_4$, 1.0 g/l $Na_2HPO_4$, 5.0 g/l $(NH4)_2SO_4$, 1.9 g/l yeast extract, 2.5 g/l $MgSO_4·7H_2O$, 0.25 g/l $CaCl_2·2H_2O$ and 0.25 ml/l trace element mix (pH 5.5). Trace elements mix was made in 5N HCl and contains 40 g/l $FeSO_4·7H_2O$, 40 g/l $CaCl_2·2H_2O$, 10 g/l $MnSO_4·7H_2O$, 10 g/l $AlCl_3·6H_2O$, 4 g/l $CoCl_2$, 2 g/l $ZnSO_4·7H_2O$, 2 g/l $Na_2MoO_4$, 1 g/l $CuCl_2·2H_2O$ and 0.5 g/l $H_3BO_3$. Where indicated, levels of trace elements and various nitrogen sources were varied. For comparison purpose, the strain was also cultured in the A-21M medium reported previously [6], which contains 120 g/l glucose, 1.5 g/l $NaNO_3$, 1.0 g/l $KNO_3$, 0.05 g/l $KH_2PO_4$, 0.2 g/l $MgSO_4·7H_2O$, 2 ppm $ZnSO_4$, 0.2 g/l yeast extract (pH 5.5).

Fed-batch fermentation was carried out in a 2 L Biostat B plus bioreactor (Sartorius Stedim Biotech, Germany). Dissolved oxygen level (pO$_2$) and air flow was maintained at 30% and 1.5 vvm, respectively. 25 ml samples were taken daily to monitor glucose, ammonium, $NO^{2-}$ and $NO^{3-}$ levels.

Optimization of massaio lactone production by Design of Experiment (DOE): Optimization of massaio lactone production by Design of Experiment (DOE) was aided with the Design-Expert® V8 Software (Stat-Ease, USA) using both the Optimised Factorial Design and Central Composite Design (CCD). Seed cultures prepared in the HDCM medium were harvested by centrifugation, washed with sterile distilled water and suspended in sterile distilled water. A fraction of which (2 ml) was inoculated into 100 ml of the respective designed medium in a 250 ml shake flask, which was cultured in a 30° C. shaking platform agitated at 200 rpm. Culture samples (15 ml) were taken daily for the analyses of cell biomass, $OD_{600}$ and metabolites.

Extraction and quantification of glycolipids: Ethyl acetate was added to cell culture at a volumetric ratio of 1:1 in a 15 ml Falcon tube. The mixture was vortexed vigorously for 20 seconds; centrifuged at 3,500 g for 10 minutes and 1 ml of the upper phase was transferred to a 1.5 ml Eppendorf tube and left to air dry overnight at room temperature in an exhaust hood. The resultant dried residue was weighed with a microbalance before being added with 10 µl menthol in methanol (10% w/v) (as the internal standard) and 300 µl of 2M NaOH. The suspended mixture was allowed to hydrolyze overnight in a shaking platform at room temperature. After mixing with 150 µl of 5M $H_2SO_4$, 450 µl ethyl acetate was added and vortexed vigorously. After centrifugation, the upper phase was used for GCMS analysis directly. Alternatively, glycolipids were extracted directly from wet cell biomass collected by centrifugation from 10 ml culture. 2 ml of 72% $H_2SO_4$ was added to the cell pellet, mixed well and allowed to stand for half an hour and then mixed with 4 ml water. After boiling for one hour, 4 ml of the mixture was added with equal volume of ethyl acetate; vortexed vigorously for 20 seconds; centrifuged at 3,500 g for 10 minutes and 1 ml of the upper phase was analyzed by GCMS or thin-layer chromatography (TLC). Conditions used TLC were as described previously [15]. Hexane can be used in place of ethyl acetate in this procedure. HCl can be used in place of $H_2SO_4$ in this procedure.

Preparation and quantification of *Massoia* lactone: Equal volume of $H_2SO_4$ was added to 2 ml of cell culture in a 15 ml Falcon tube. Samples were vortexed briefly and left in room temperature for 30 mins. After adding 4 ml of water, Falcon tubes were boiled in a water-bath for 60 min; cooled for 10 mins at room temperature, and then 4 ml of ethyl acetate was added into the tubes, which were mixed vigorously with a vortex for 20 seconds. Samples were centrifuged for 10 mins at 3,500 rcf and 1 ml of the top organic layer was transferred to a 2 ml glass vial containing 50 mg of $Na_2SO_4$ and 10 µl menthol solution in methanol (10%). *Massoia* lactone was quantified using GCMS using menthol as the internal standard. HCl can be used in place of $H_2SO_4$ in this procedure.

Quantification of fatty acid: Cell biomass was collected from 20 ml culture by centrifugation and dried in a 60° C. oven until constant weight is reached. The resultant dried pellets were frozen in liquid nitrogen and grinded to a fine powder using mortar and pestle. A 250 mg sample was transferred to a 15 ml Falcon tube and then mixed with 2 ml of 72% $H_2SO_4$ and 10 µl of 10% (w/v) pentadeconoic acid in methanol (as the internal standard). The samples were hydrolyzed at room temperature for 30 mins and then mixed with 4 ml water. After boiling for 1 hour, a 500 µl fraction was transferred to a 2 ml Eppendorf tube and fatty acids were extracted by mixing with 1 ml methanol/chloroform mixture (1:1 v/v). After centrifugation, the bottom layer was collected by pipetting and washed once with PBS buffer in an Eppendorf tube. The methanol/chloroform bottom layer was collected after centrifugation and left to dry at room temperature in an exhaust hood. 300 µl petroleum ester (Fisher Chemicals, CAS: 64742-49-0)/benzene (QREC Asia SDN BDH, CAS 71-43-2) mixture (1:1 v/v) and 300 µl 0.4 M KOH in methanol was added to solubilize the dried residues. Esterification was performed at room temperature for 3 hours. After separation by centrifugation, 50 μl of the top layer was diluted with 450 μl of methanol and subjected to analysis by GC-MS.

GC-MS analysis: GC-MS analysis was performed using GCMS-QP2010 Ultra (Shimadzu Corporation, Japan). Samples (10) were injected into a HP-88 column (30 m×0.25 mm ID×0.20 μm) (Agilent Technologies, USA) and run with helium as the carrier gas maintained at 10 psi. A split-less injection time of 0.5 min was used. The GC started at an initial temperature of 50° C. for 1 minute, ramped at 15° C. per minute up to 150° C. and 3° C. per minute to a final temperature 240° C. The spectrometer was scanned from 41-400 amu. The compounds were identified by searching against the NIST 08 mass spectral library. Quantification of fatty acid ester and *Massoia* lactone was done by comparing the peak area between the target compounds and the respective internal standards.

Other quantification methods: Glucose levels were quantified using a Shimadzu Prominence UFLC (Shimadzu, Japan). Samples were run through an Aminex HPX-87H column (Bio-rad, USA) maintained at 50° C. 5 mM $H_2SO_4$ was used as the mobile phase and run at a flow rate of 0.7 ml/min. Total nitrates, nitrites and ammonia levels were determined using the method as described [16, 17].

RNA Sampling and RNA-sequencing: Cell cultures (1 ml) were collected at day 1, 2, 3 and RNAs were immediately extracted with RiboPure™ RNA Purification Kit, yeast (Life Technologies, USA). After determination of the RNA quantity and quality by Nanodrop and agarose gel electrophoresis, the RNA samples were sent to Macrogen Inc. (Korea) for cDNA shotgun library construction and sequencing using Illumina Hiseq 2000.

Computational analysis: Computational analysis was performed in the Galaxy platform (http://galaxyproject.org/) installed locally [18]. Raw reads (100 bp paired-end) were analyzed with NGS QC toolkit [19] for their quality. Then, Tophat and Cufflinks [20-22] were used to identify differential gene/transcript expression based on published genome sequences as the references. de novo assembly was performed with Trinity [23, 24], which produced ~18 k isoforms or transcripts. Differentially expressed (DE) transcripts and expression profile clusters were done with Bioconductor with rsem and edgeR packages [25, 26].

Example 2

Identification of *Massoia* Lactone-Producing Microbial Strains

Nile red is an uncharged hydrophobic molecule whose fluorescence is strongly influenced by the polarity of its environment and it is often used as a marker for hydrophobic substances, such as lipid, glycolipids and hydrophobic proteins [27-29]. By screening water and soil samples obtained from local costal environment using Nile red as a marker, 32 candidates were identified that showed significant red fluorescence, among which strain W5-2 was identified as fungus closely related to *Aureobasidium* species based on the sequence comparison of the rDNA ITS region (SEQ ID NO. 1) (FIG. 1). W5-2 colonies turned black after 7 days of culture on solid medium (not shown).

Because *Aureobasidium* species are identified by phylogenetic analysis of their whole genome sequences as well as certain phylogenetically important genes, such as housekeeping genes encoding Actin, β-tubulin, calmodulin, chytin synthase, NAD-dependent glycerol-3-phosphate dehydrogenase and translation elongation factor 1α (TEF1A), the whole transcriptome of W5-2 was chosen to compare those of the type *Aureobasidium* strains [30].

The overall alignment rates of raw reads to the 4 reference genomes of *Aureobasidium* species [31] were low, ~55.7% to *A. melanogenum* and ~15-19% to the rest *Aureobasidium* species (Table 1). Therefore, de novo assembly of RNA-seq data was performed using the Trinity program [32], producing a sequence library of ~18 k isoforms/transcripts. The overall alignment rate of raw reads to this local reference was increased to above 95%.

TABLE 1

Mapping Rates to Reference Genomes of Aurebasidium Species

|  | T0-1 d | T0-2 d | T0-3 d | T2-1 d | T2-2 d | T2-3 d | Average |
| --- | --- | --- | --- | --- | --- | --- | --- |
| *A. melanogenum* | 60.47% | 52.76% | 52.10% | 58.24% | 56.73% | 54.06% | 55.72% |
| *A. pullulans* | 21.68% | 15.71% | 15.81% | 16.80% | 15.06% | 13.86% | 16.49% |
| *A. subglaciale* | 19.80% | 14.23% | 14.41% | 15.46% | 13.48% | 12.41% | 14.97% |
| *A. namibiae* | 24.90% | 18.11% | 18.23% | 20.08% | 18.04% | 16.32% | 19.28% |

Note: Raw reads were mapped to reference genome using TopHat software [33]. RNA samples were extracted from W5-2 cell culture in Medium T0 and Medium T2 at Day, 1, 2 and 3 respectively.

Figure 2:
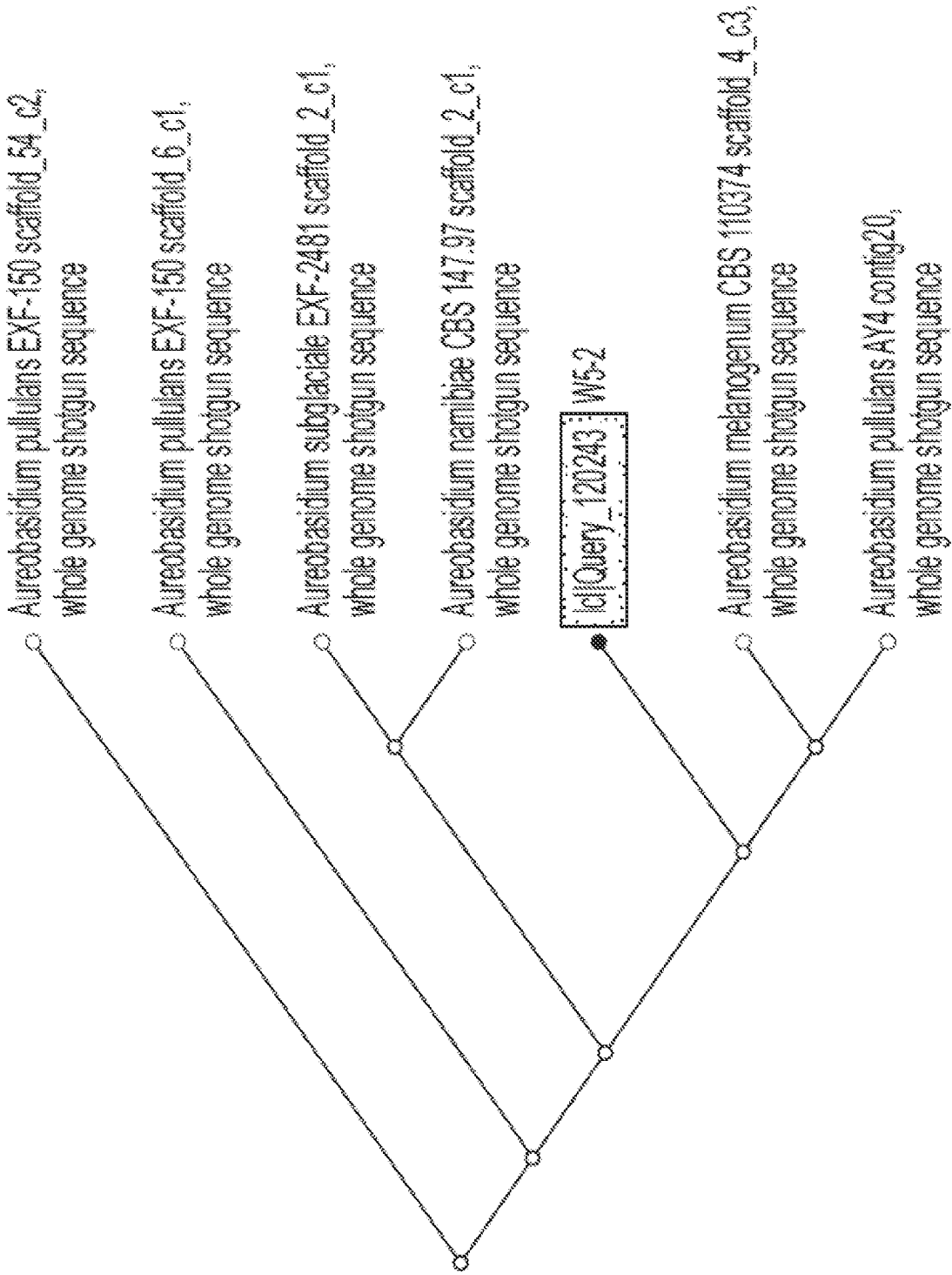
FIG. 2 shows results of a GPD1 CDS search by BLASTn against the Whole Genome Shortgun Motifs of *Aureobasidium* species. This search identified two highly related genomic sequences from *Aureobasidium melanogenum* CBS 110374 scaffold_4_c3 and *Aureobasidium pullulans* AY4 contig20 (which is in fact *A. melanogenum*). *Aureobasidium namibiae* CBS, *Aureobasidium subglaciale* EXF-2481 and *Aureobasidium pullulans* EXF-150 had only partial sequences in the region. The phylogenic tree is generated Blast Tree View at NCBI using fast minimal evolution method.

DNA sequence divergence in GPD1 gene is used as an important indicator for phylogenetic analysis in *Aureobasidium* species [30]. GPD1 CDS sequence (SEQ ID NO:2) was searched by BLASTn against the Whole Genome Shortgun sequences of *Aureobasidium* species at NCBI. Six highly related sequences were identified. Phylogenic tree generated Blast Tree View using fast minimal evolution method is shown in FIG. 2, which clearly places the W5-2 GPD1 sequence between *A. melanogenum* CBS 110374/*A. pullulans* AY4, which has been re-classified as *A. melanogenum* [30], and *A. namibiae* CBS 147.97/*A. subglaciale* EXF-2481. W5-2 showed highest divergence from *A. pullulans* EXF-150 and lowest divergence to *A. melanogenum*.

*A. pullulans* is known to produce antibiotic aureobasidin A [34], which is made by a huge polyketide synthase Aba1[35]. A search of ABA1 CDS (Genbank no. EU886741) against the W5-2 whole transcriptome failed to identify any homologs in the genome. Therefore, strain W5-2 does not encode a functional ABA1 gene and is not likely to produce any antibiotics.

Figure 4A:
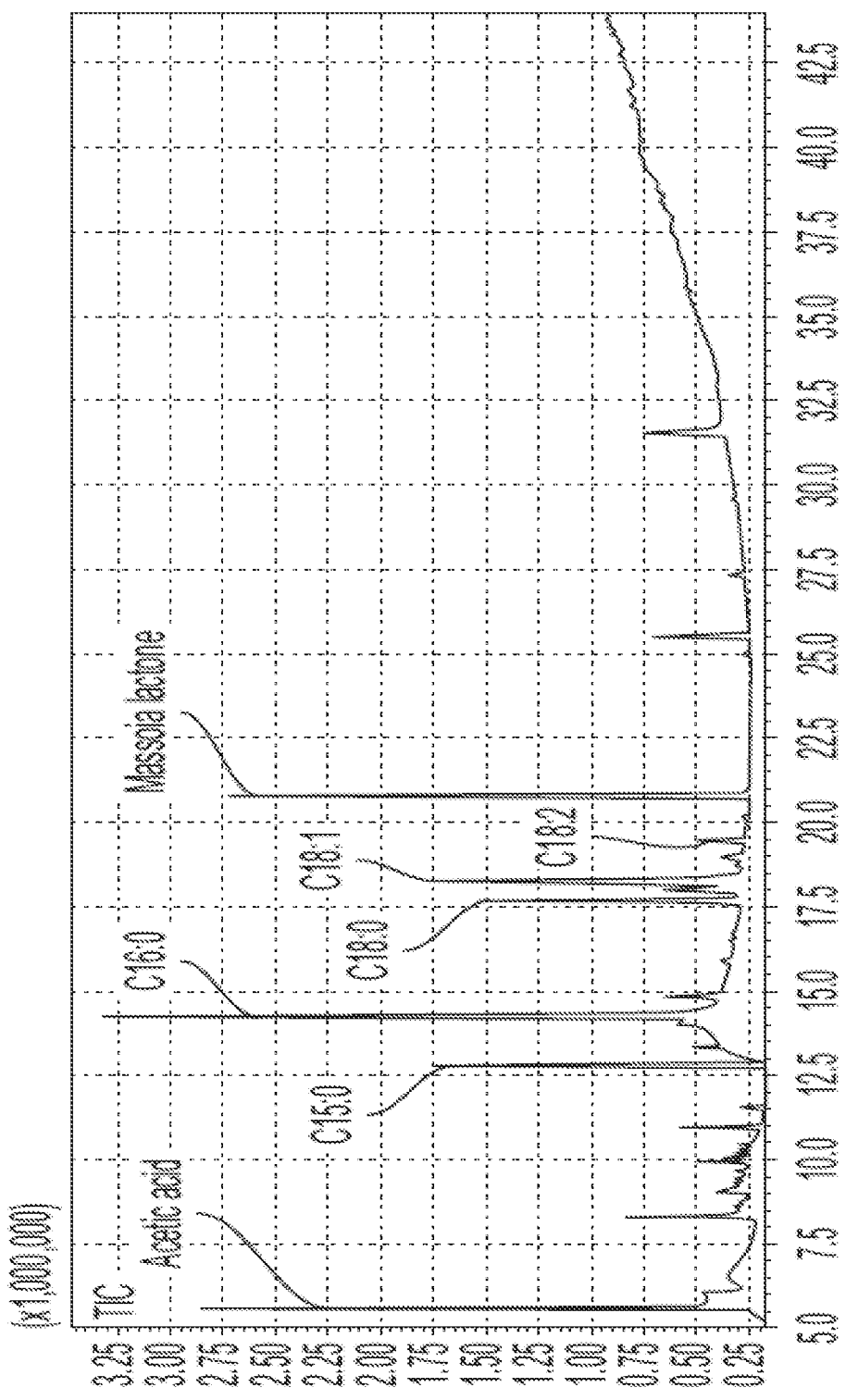
FIGS. 4A and 4B show GCMS analysis of *Aureobasidium* isolate W5-2.
Figure 4B:
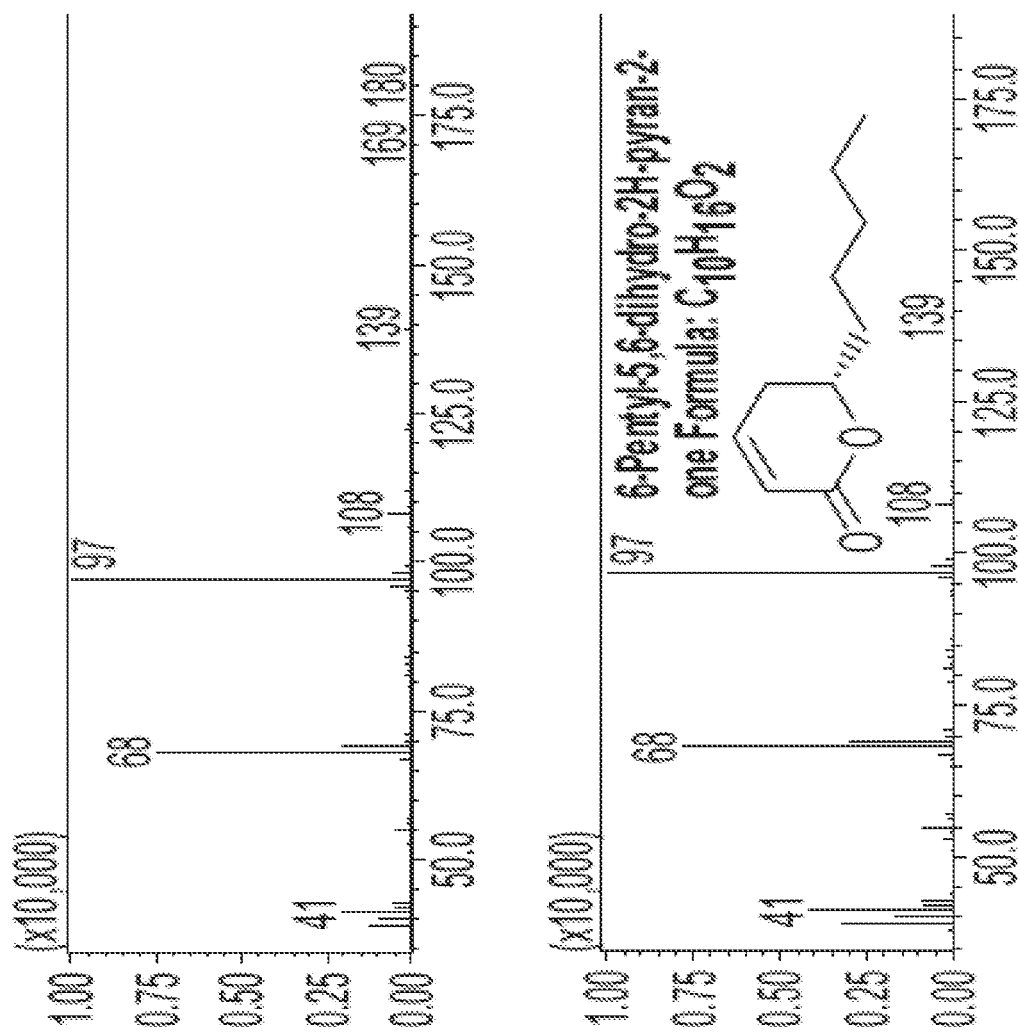

Confocal imaging confirmed that Nile red stained the cytoplasm intensely with little signal in the cytoplasmic membrane, suggesting the high accumulation of hydrophobic substance in the cells (FIG. 3C). Fatty acid profiling by GCMS revealed that the total ethyl acetate extract contained 52.28% oleic acid, 33.9% palmitic acid, 3.98% linoleic acid, 1.31% palmatolic acid and about 1.3% of long chain (C24 and above) fatty acids (Table 2). Thin layer chromatography (TLC) confirmed the production of triacylglyceride (TAG) and glycolipids (FIG. 3D). Unexpectedly, the GCMS profile showed a significant peak with a retention time of approximately 25.7 min, which had >93% similarity to *Massoia* lactone, i.e., 6-pentyl-5,6-dihydro-2H-pyran-2-one (FIGS. 4A and 4B). Sensory test of the dried cell pellet confirmed the presence a strong coconut-like aroma.

TABLE 2

Fatty Acid Profile of W5-2

| | C16 | C16:1 | C18 | C18:1 | C18:2 | C24 |
|---|---|---|---|---|---|---|
| W5-2 | 33.91% | 1.31% | 7.24% | 52.28% | 3.98% | 1.29% |

Example 3

Medium Optimization Using Central Composite Designs (CCD)

Figure 5:
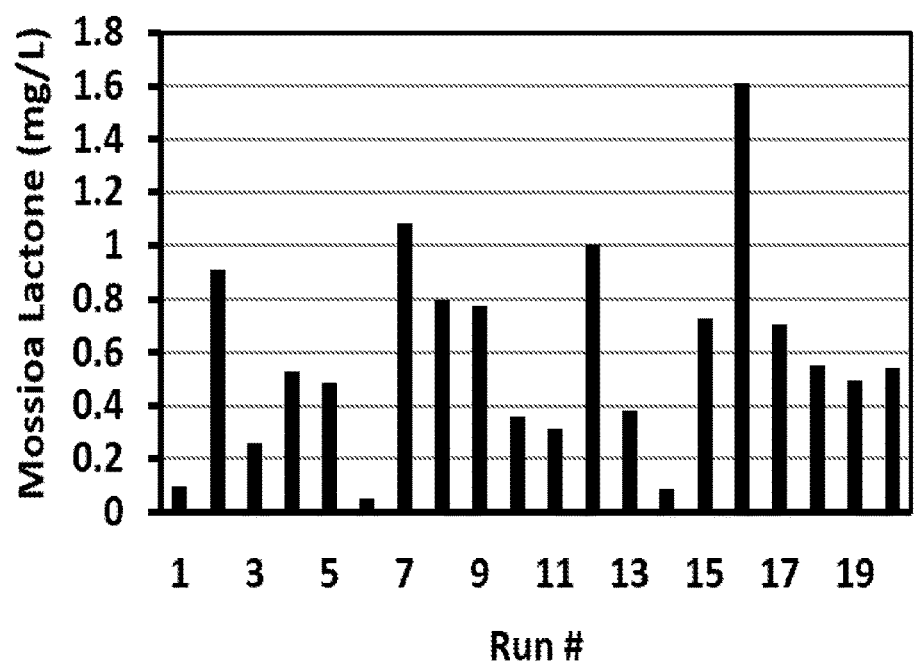
FIG. 5 shows using Central Composite Design (CCD) to optimize concentration of urea, trace elements and glucose.
Figure 6:
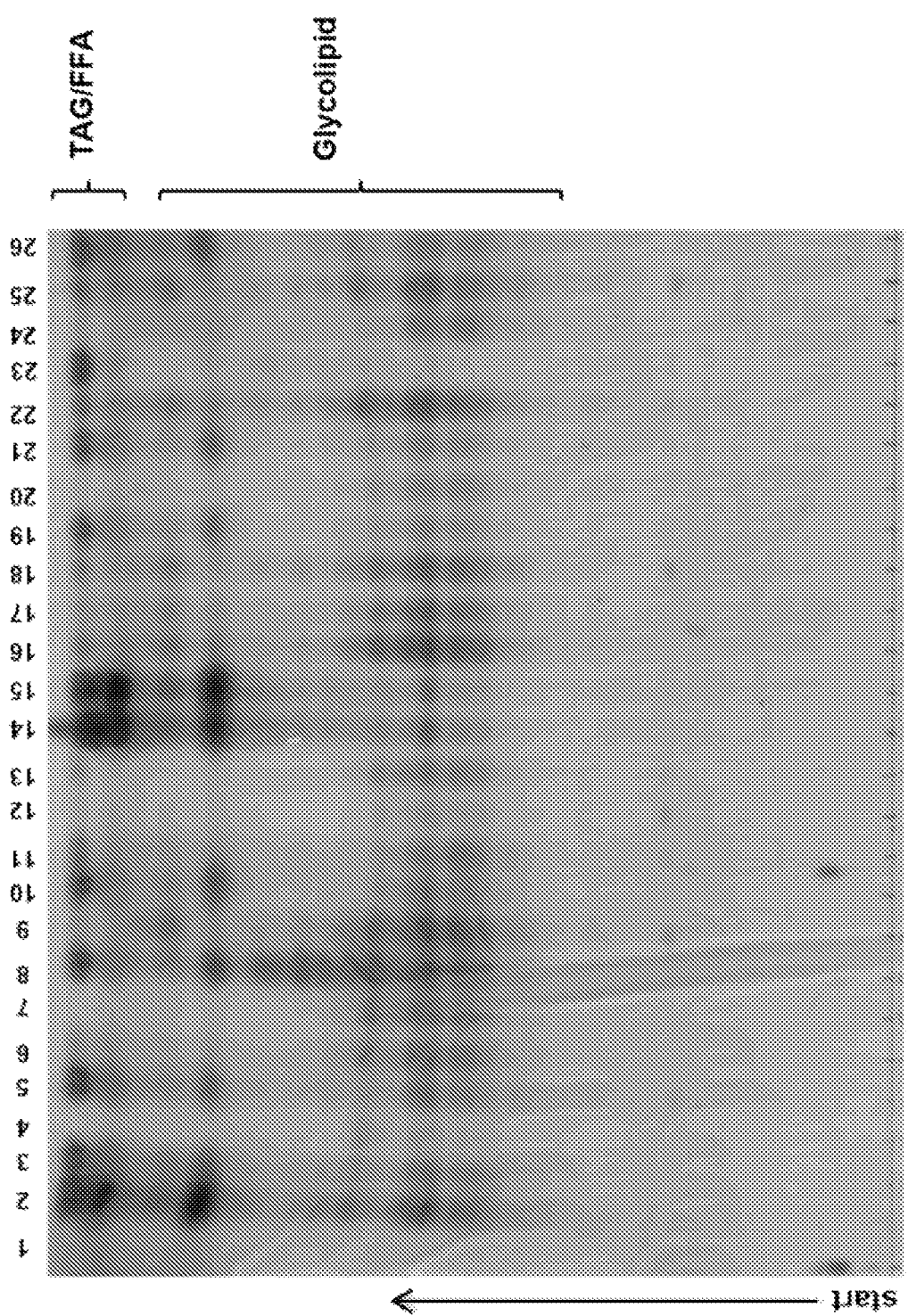
FIG. 6 shows glycolipid profiles of various media. Medium composition is shown in Table 2. Seed culture was prepared by inoculating 1.5 ml of frozen 7% DMSO culture into 100 ml of the original HDCM in a 250 ml flask and cultured for 48 hrs at 30° C. The cells were harvested by centrifugation, re-suspended in water and inoculated at 2% into each medium in 250 ml flasks. Cells were cultured at 30° C. with 200 rpm agitation. Samples shown are taken from the 6th day.

To improve *Massoia* lactone production, the *Rhodotorula glutinis* high density (HMDC) medium [14] was modified by changing the levels of nitrogen source (urea), carbon source (glucose) and trace element mix, which contains $FeSO_4 \cdot 7H_2O$, $CaCl_2 \cdot 2H_2O$, $MnSO_4$, $AlCl_3 \cdot 6H_2O$, $CoCl_2$, $ZnSO_4 \cdot 7H_2O$, $Na_2MoO_4 \cdot 2H_2O$, $CuCl_2 \cdot 2H_2O$ and $H_3BO_4$. Medium compositions are shown in Table 3. *Massoia* lactone production was low, ranging from 0.05 mg/l (Run 6) to 1.61 mg/l (Run 16) (FIG. 5). While there were obvious differences amongst the runs, none of the parameters appeared to significantly influence the production by ANOVA analysis (p<0.05) (Table 4). Since *Massoia* lactone produced in *A. pullulans* has been reported to derive from glycolipid [6], we monitored glycolipid levels by TLC. Again, CCD was employed to optimize the nitrogen source and carbon source in HMDC medium, with urea and yeast extract set as category factors while glucose level was set at 7.5, 20, 50, 80, 92.4 g/l respectively. In addition, the trace element mix was set at 0.034, 0.2, 0.6, 1.0, 1.17 ml per litre medium respectively (Table 5). High variations in glycolipid profiles were observed: Run No. 15 appeared to be the best combination for glycolipid production (FIG. 6), with 285 mg/l *Massoia* lactone present in the acid hydrolyzed glycolipid products. Therefore, we chose a medium containing high level of glucose (~100 g/1), 2 g/l urea as the sole nitrogen source and 0.6 ml original HMDC trace element mix for subsequent medium optimizations. For convenience, this medium is referred as the Run 15 (R15) medium.

TABLE 3

Optimization of Nitrogen source, Carbon Source and Trace Elements by CCD

| Run No. | Urea (g/L) | Glucose (g/l) | Trace (ml/l) |
|---|---|---|---|
| 1 | 2.89 | 36.21 | 0.95 |
| 2 | 1.11 | 83.78 | 0.24 |
| 3 | 2 | 60 | 1.2 |
| 4 | 2 | 60 | 0.6 |
| 5 | 0.5 | 60 | 0.6 |
| 6 | 2 | 60 | 0 |
| 7 | 2.89 | 36.21 | 0.24 |
| 8 | 2 | 60 | 0.6 |
| 9 | 2 | 60 | 0.6 |
| 10 | 2 | 60 | 0.6 |
| 11 | 3.5 | 60 | 0.6 |
| 12 | 1.11 | 83.78 | 0.957 |
| 13 | 1.11 | 36.21 | 0.96 |
| 14 | 2 | 20 | 0.6 |
| 15 | 2 | 60 | 0.6 |
| 16 | 2 | 50 | 1.00 |
| 17 | 2.89 | 83.78 | 0.24 |
| 18 | 1.11 | 36.21 | 0.24 |
| 19 | 2 | 100 | 0.6 |
| 20 | 2.89 | 83.78 | 0.96 |

TABLE 4

Anova Analysis of Table 3

| Source | Sum of Squares | df | Mean Square | F Value | p-value Prob > F | Remarks |
|---|---|---|---|---|---|---|
| Model | 0.75 | 3.00 | 0.25 | 1.98 | 0.1580 | not significant |
| A-Trace elements | 0.23 | 1.00 | 0.23 | 1.86 | 0.1919 | |
| B-Urea | 0.00 | 1.00 | 0.00 | 0.02 | 0.8813 | |
| C-Glucose | 0.51 | 1.00 | 0.51 | 4.05 | 0.0612 | |
| Residual | 2.02 | 16.00 | 0.13 | | | |
| Lack of Fit | 1.87 | 11.00 | 0.17 | 5.95 | 0.0308 | significant |
| Pure Error | 0.14 | 5.00 | 0.03 | | | |
| Cor Total | 2.77 | 19.00 | | | | |
| Std. Dev. | 0.36 | | R-Squared | 0.27 | | |
| Mean | 0.59 | | Adj R-Squared | 0.13 | | |
| C.V. % | 60.42 | | Pred R-Squared | −0.30 | | |
| PRESS | 3.60 | | Adeq Precision | 4.27 | | |

TABLE 5

Medium Compositions of Central Composite Design 1 (CCD1)

| Run | Nitrogen source | Glucose (g/l) | Trace element mix (ml/l) | lactone titre (mg/l) |
|---|---|---|---|---|
| 1 | Urea | 7.57 | 0.6 | 0.256 |
| 2 | Yeast extract | 50 | 0.03 | 4.192 |
| 3 | Yeast extract | 50 | 0.6 | 2.384 |
| 4 | Yeast extract | 7.57 | 0.6 | 1.386 |
| 5 | Yeast extract | 80 | 0.2 | 2.594 |
| 6 | Yeast extract | 20 | 0.2 | 3.257 |
| 7 | Yeast extract | 20 | 1 | 4.130 |
| 8 | Urea | 80 | 0.2 | 3.082 |
| 9 | Urea | 50 | 1.17 | 4.978 |
| 10 | Yeast extract | 50 | 0.6 | 3.100 |
| 11 | Yeast extract | 80 | 1 | 3.366 |
| 12 | Urea | 20 | 1 | 1.853 |
| 13 | Urea | 20 | 0.2 | 4.103 |
| 14 | Urea | 80 | 1 | 4.935 |
| 15 | Urea | 92.43 | 0.6 | 6.731 |
| 16 | Urea | 50 | 0.6 | 2.300 |
| 17 | Urea | 50 | 0.6 | 5.272 |
| 18 | Urea | 50 | 0.6 | 3.011 |
| 19 | Yeast extract | 50 | 0.6 | 4.325 |
| 20 | Yeast extract | 50 | 1.17 | 2.510 |
| 21 | Yeast extract | 50 | 0.6 | 2.651 |
| 22 | Urea | 50 | 0.6 | 5.715 |
| 23 | Urea | 50 | 0.03 | 4.990 |
| 24 | Yeast extract | 92.43 | 0.6 | 0.934 |
| 25 | Urea | 50 | 0.6 | 3.700 |
| 26 | Yeast extract | 50 | 0.6 | 4.855 |

Note:
urea and yeast extract were both set at 1.9 g/l.

Example 4

Figure 7A:
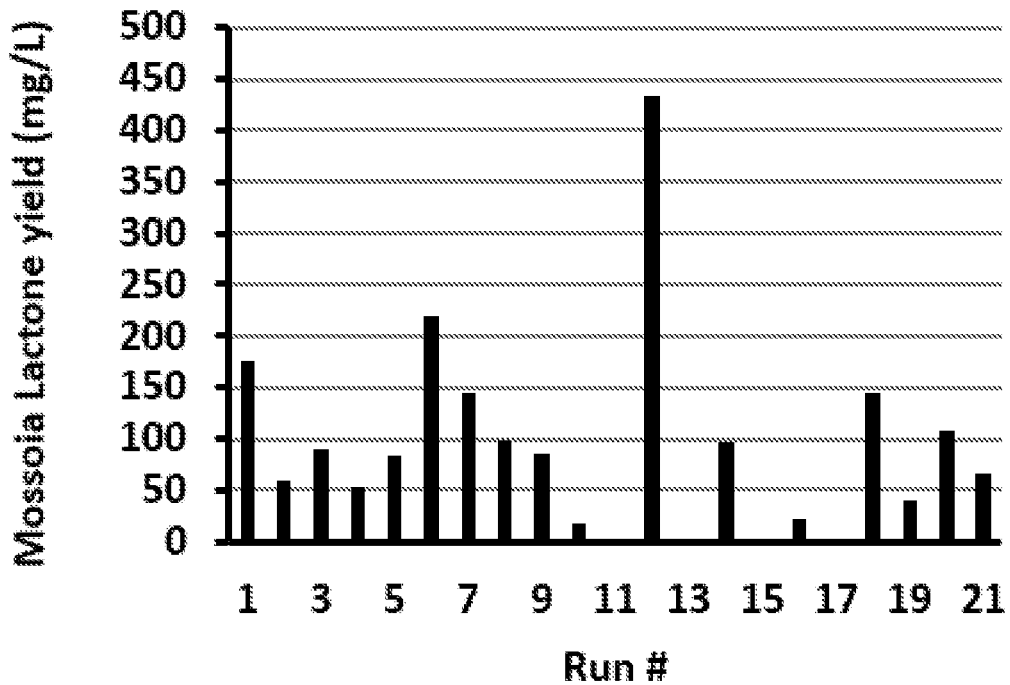
FIGS. 7A and 7B show the effects of trace elements. Media were inoculated with water-washed cell stock cultured in HMDC medium to 0.1 $OD_{600}$ and cultured at 30° C. with 200 rpm shaking for 8 days.

Optimization of Trace Elements Using Factorial Designs $FeSO_4$, $MnSO_4$, $ZnSO_4$, $CuCl_2$, $AlCl_3$ were supplemented to the R15 medium using Factorial Optimal Design at the same concentration [14], either individually or in combinations (Table 6). Results showed that Run #12 which was supplemented with $Fe^{2+}$, $Zn^{2+}$ and $Cu^{2+}$ (named as T3 medium hereafter) produced the highest level of *Massoia* lactone, reaching 433 mg/l on day 8. Run #6 in which $Mn^{2+}$ and $Zn^{2+}$ were both supplemented (named as T2 medium hereafter) ranked $2^{nd}$, yielding 218 mg/l *Massoia* lactone (FIG. 7A; Table 6). In contrast, Basal medium (Run 2, referred to as T0 medium) with $CoCl_2$, $HBO_3$ and $NaMoO_4$ only produced only 58 mg/l *Massoia* lactone, more than 14 folds lower than with T3 medium (FIG. 7A, Table 6). Anova analysis showed that $ZnSO_4$, $CuCl_2$, $FeSO_4$, $ZnSO_4$, $FeSO_4$—$CuCl_2$, $FeSO_4$—$AlCl_3$, and $CuCl_2$—$AlCl_3$ significantly affected *Massoia* lactone production (Tables 6 and 7).

TABLE 6

Trace Elements Part 1

| Run # | $FeSO_4$ | $MnSO_4$ | $ZnSO_4$ | $CuCl_2$ | $AlCl_3$ |
|---|---|---|---|---|---|
| 1 | Y | N | Y | Y | Y |
| 2 | N | N | N | N | N |
| 3 | Y | Y | N | Y | Y |
| 4 | N | Y | N | N | Y |
| 5 | N | N | N | N | Y |
| 6 | N | Y | Y | N | N |
| 7 | N | N | Y | N | Y |
| 8 | Y | N | Y | N | N |
| 9 | N | N | Y | Y | N |
| 10 | Y | N | N | N | Y |
| 11 | Y | N | N | Y | N |
| 12 | Y | N | Y | Y | N |
| 13 | Y | N | N | N | N |
| 14 | N | Y | Y | Y | Y |
| 15 | Y | N | N | Y | N |
| 16 | Y | Y | N | N | Y |
| 17 | Y | Y | N | N | N |
| 18 | Y | Y | Y | Y | Y |
| 19 | N | Y | N | Y | N |
| 20 | Y | Y | Y | Y | N |
| 21 | N | N | N | Y | Y |

Note:
Basal medium (T0 medium) contained 100 g/l glucose, 12.5 g/l $KH_2PO_4$, 1.0 g/l $Na_2HPO_4$, 5.0 g/l $(NH_4)_2SO_4$, 2 g/l urea, 2.5 g/l $MgSO_4 \cdot 7H_2O$, 0.25 g/l $CaCl_2 \cdot 2H_2O$, 2.4 mg/l $CoCl_2$, 0.3 mg/l $HBO_3$ and 1.2 mg/l $NaMoO_4$, pH 5.5. 0.6 ml of trace element mix was added to each litre of medium. Where indicated by N, the trace element was omitted in the trace element mix. The final medium contained various combinations of $FeSO_4 7H_2O$ (24 mg/l), $MnSO_4$ (6 mg/l), $ZnSO_4$ (1.2 mg/l) and $CuCl2$ (0.6 mg/l).

TABLE 7

Anova Analysis of Table 6

| Source | Sum of Squares | df | Mean Square | F Value | p-value Prob > F | Remarks |
|---|---|---|---|---|---|---|
| Model | 469.03 | 15.00 | 31.27 | 17.67 | 0.0025 | significant |
| A-$FeSO_4$ | 6.58 | 1.00 | 6.58 | 3.72 | 0.1118 | |
| B-$MnSO_4$ | 5.67 | 1.00 | 5.67 | 3.20 | 0.1335 | |
| C-$ZnSO_4$ | 305.29 | 1.00 | 305.29 | 172.50 | <0.0001 | significant |
| D-$CuCl_2$ | 22.61 | 1.00 | 22.61 | 12.78 | 0.0160 | significant |
| E-$AlCl_3$ | 3.46 | 1.00 | 3.46 | 1.95 | 0.2211 | |
| AB | 0.87 | 1.00 | 0.87 | 0.49 | 0.5151 | |
| AC | 69.62 | 1.00 | 69.62 | 39.34 | 0.0015 | significant |
| AD | 22.14 | 1.00 | 22.14 | 12.51 | 0.0166 | significant |
| AE | 16.67 | 1.00 | 16.67 | 9.42 | 0.0278 | significant |
| BC | 2.88 | 1.00 | 2.88 | 1.63 | 0.2579 | |
| BD | 0.44 | 1.00 | 0.44 | 0.25 | 0.6408 | |
| BE | 5.87 | 1.00 | 5.87 | 3.32 | 0.1282 | |
| CD | 0.18 | 1.00 | 0.18 | 0.10 | 0.7598 | |
| CE | 0.29 | 1.00 | 0.29 | 0.16 | 0.7043 | |
| DE | 19.93 | 1.00 | 19.93 | 11.26 | 0.0202 | significant |
| Residual | 8.85 | 5.00 | 1.77 | | | |
| Cor Total | 477.88 | 20.00 | | | | |
| Std. Dev. | 1.33 | | R-Squared | 0.98 | | |
| Mean | 21.66 | | Adj R-Squared | 0.93 | | |
| C.V. % | 6.14 | | Pred R-Squared | 0.29 | | |
| PRESS | 339.46 | | Adeq Precision | 16.34 | | |

Figure 7B:
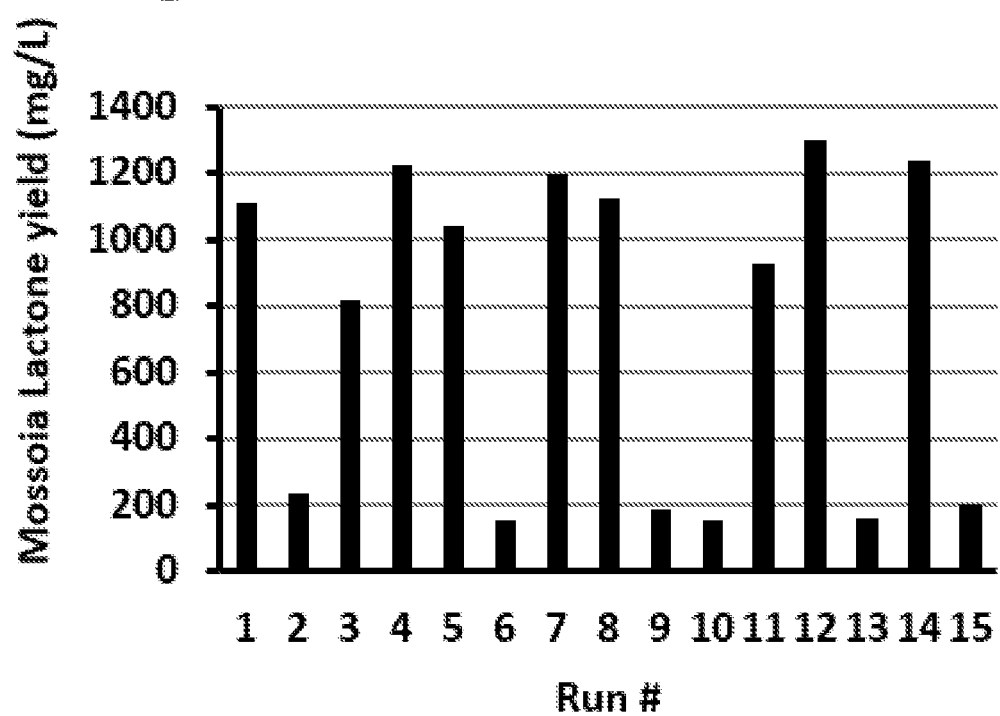

In another experiment, the effects of the remaining trace elements, i.e., $CoCl_2$, $HBO_3$ and $NaMoO_4$ were tested. Results showed that $CoCl_2$ (2.4 mg/l) strongly inhibited *Massoia* lactone production (p<0.0001) while $NaMoO_4$ (1.2 mg/l) significantly improved the production (p<0.05). $HBO_3$ (0.3 mg/l) did not appear to have significant effect (Tables 8 and 9). The best medium was Run 12, with a *Massoia* lactone yield of 1300 mg/l (FIG. 7B). Notably, this medium contains high level of $CaCl_2$ (0.25 g/l $CaCl_2 \cdot 2H_2O$).

TABLE 8

Trace Elements Part 2

| Run # | $CoCl_2$ | $NaMoO_4$ | $H_3BO_4$ |
|---|---|---|---|
| 1 | N | Y | Y |
| 2 | Y | Y | N |
| 3 | N | N | N |
| 4 | N | Y | N |
| 5 | N | N | N |
| 6 | Y | N | Y |
| 7 | N | Y | Y |
| 8 | N | N | Y |
| 9 | Y | Y | Y |
| 10 | Y | N | N |
| 11 | N | N | Y |
| 12 | N | Y | N |
| 13 | Y | Y | Y |

Note:
Media were inoculated to 0.1 $OD_{600}$ with water-washed cell stock cultured in HMDC medium and cultured at 30° C. with 200 rpm shaking for 8 days. Basal medium was T0 medium (Table 6) with various combinations of $CoCl_2$ (2.4 mg/l), $HBO_3$ (0.3 mg/l) and $NaMoO_4$ (1.2 mg/l).

TABLE 9

Anova Analysis of Table 8

| Source | Sum of Squares | df | Mean Square | F Value | p-value Prob > F | Remarks |
|---|---|---|---|---|---|---|
| Model | 2702668.48 | 6.00 | 450444.75 | 47.99 | <0.0001 | significant |
| A-$CoCl_2$ | 2431273.40 | 1.00 | 2431273.40 | 259.01 | <0.0001 | significant |
| B-$NaMoO_4$ | 60353.96 | 1.00 | 60353.96 | 6.43 | 0.0443 | significant |
| C-$H_3BO_4$ | 769.68 | 1.00 | 769.68 | 0.08 | 0.7842 | |
| AB | 21411.70 | 1.00 | 21411.70 | 2.28 | 0.1817 | |
| AC | 320.50 | 1.00 | 320.50 | 0.03 | 0.8595 | |
| BC | 18462.23 | 1.00 | 18462.23 | 1.97 | 0.2103 | |
| Residual | 56320.37 | 6.00 | 9386.73 | | | |
| Lack of Fit | 3671.82 | 1.00 | 3671.82 | 0.35 | 0.5805 | not significant |
| Pure Error | 52648.56 | 5.00 | 10529.71 | | | |
| Cor Total | 2758988.86 | 12.00 | | | | |
| Std. Dev. | 96.89 | R-Squared | 0.98 | | | |
| Mean | 741.48 | Adj R-Squared | 0.96 | | | |
| C.V. % | 13.07 | Pred R-Squared | 0.91 | | | |
| PRESS | 243152.35 | Adeq Precision | 15.75 | | | |

Example 5

Utilization of Various Carbon Sources by *A. melanogenum* W5-2

Figure 8:
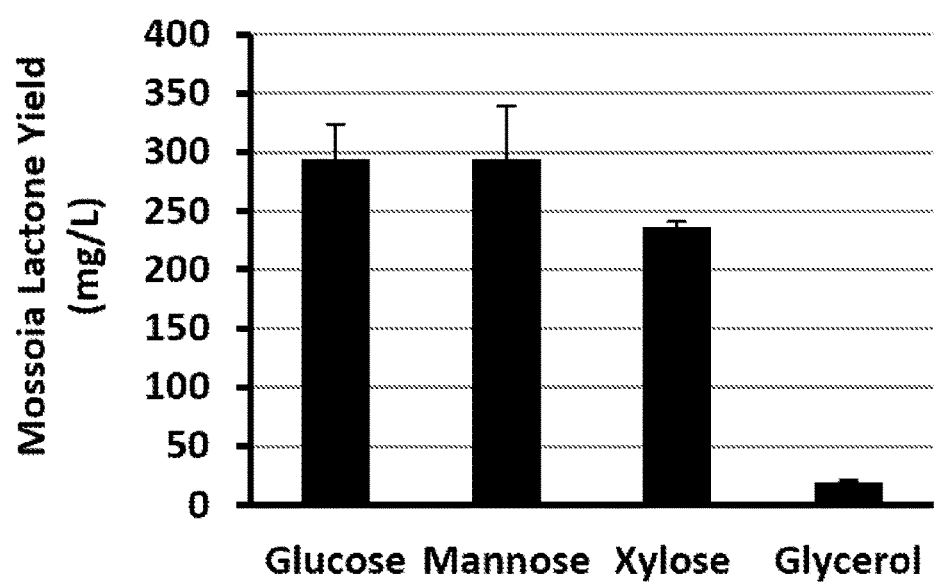
FIG. 8 shows production of *Massoia* lactone with various carbon sources. W5-2 was cultured in T2 medium with glucose, mannose, xylose or glycerol as carbon sole source for 4 days. Each data set derived from 3 biological replicates. Error bars indicates SD.

To see if strain W5-2 is able to utilize other carbon sources for the production of *Massoia* lactone, glucose in T2 medium was replaced with the same concentrations of D-(+)-mannose, D-(+)-xylose and glycerol. Mannose was essentially as efficiently utilized as glucose. The strain also efficiently converted xylose to *Massoia* lactone although the yield was about 20% lower than with glucose under the conditions tested. Glycerol was a poor carbon source (FIG. 8).

Example 6

Fed-Batch Fermentation

Figure 9:
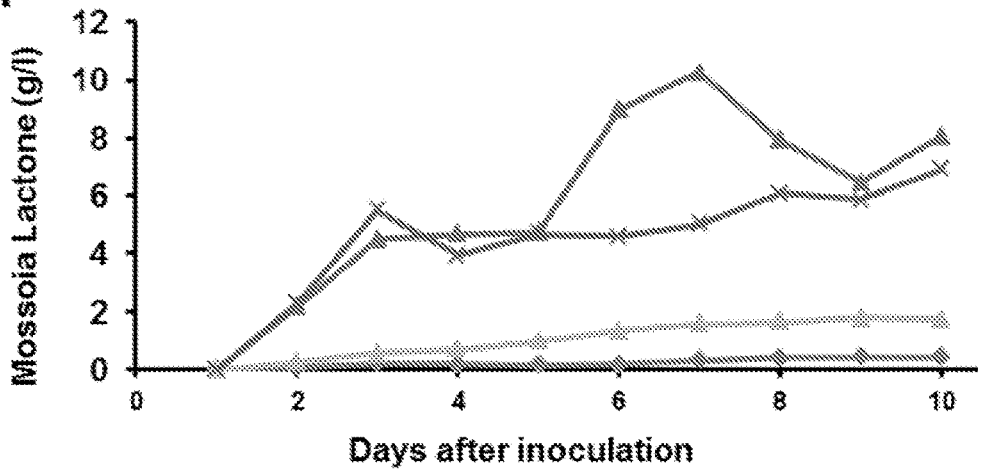
FIGS. 9A-9C show a comparison of *Massoia* lactone yields in 4 media. The symbols for the media are shown in FIG. 9C. AM refers to a modified A-21M medium (MA-21M) containing 120 g/l glucose, 1.5 g/l $NaNO_3$, 1.0 g/l $KNO_3$, 0.05 g/l $KH_2PO_4$, 0.2 g/l $MgSO_4$, 0.0056 g/l $FeSO_4$, 0.2 g/l Yeast Extract (pH 5.5). Seed culture was made in HMDC medium with complete trace elements.
Figure 9:
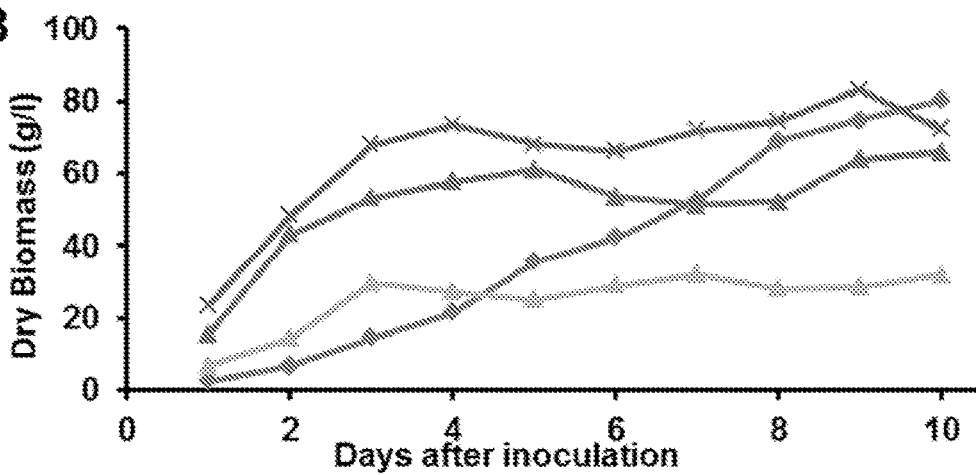
Figure 9:
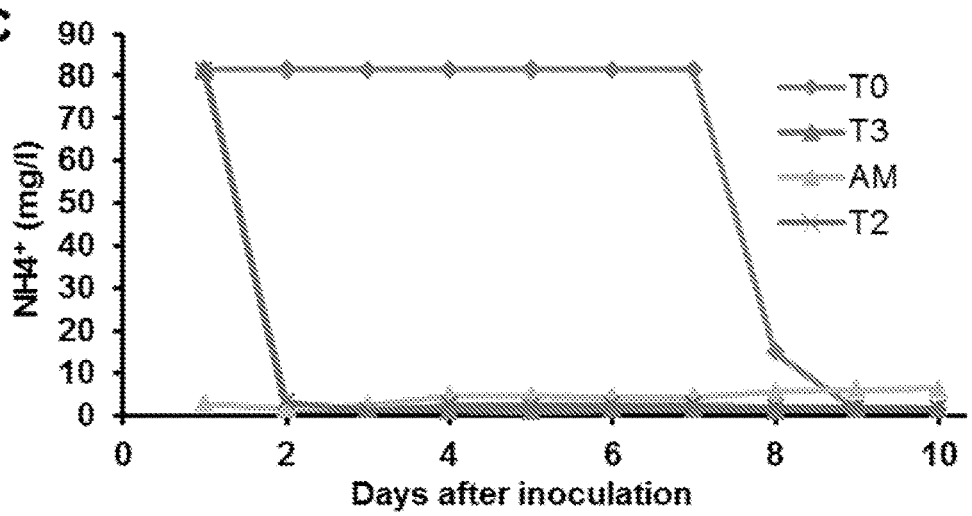
Figure 10:
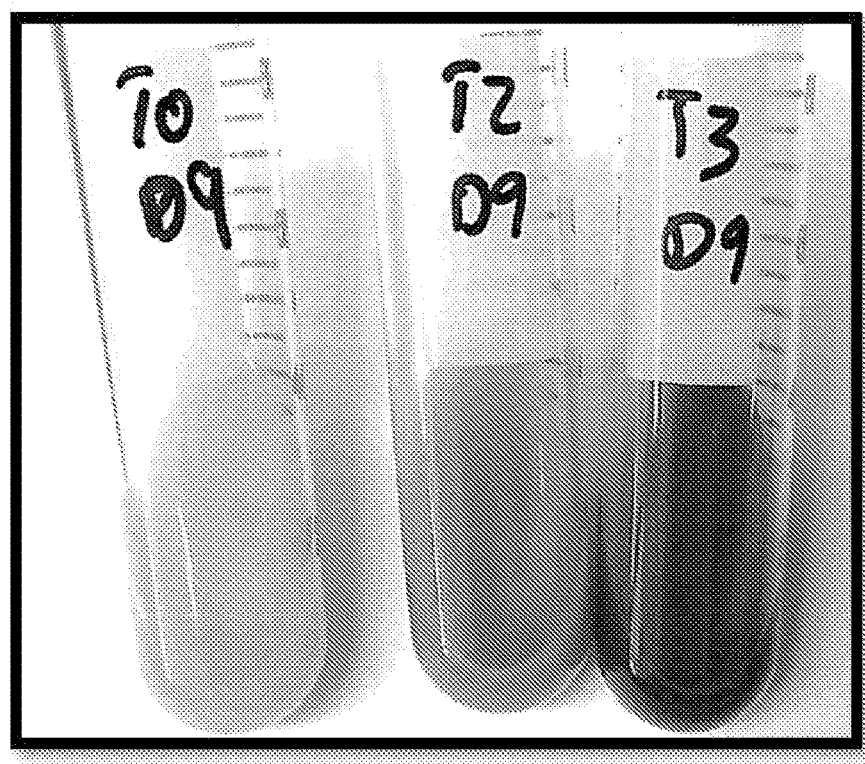
FIG. 10 shows a comparison of cells cultured in T0, T2 and T3 media. Cells were cultured in 2 L fermentor for 9 days.

To verify the performance of the optimized media, fed-batch fermentation was performed in 2 L bioreactors using T0, T2 and T3 media. As the original A-21M medium barely supports the growth of W-52, a modified A-21M medium (MA-21M) was used as a reference. MA-21M contained 120 g/l glucose, 1.5 g/l $NaNO_3$, 1.0 g/l $KNO_3$, 0.05 g/l $KH_2PO_4$, 0.2 g/l $MgSO_4$, 0.0056 g/l $FeSO_4$, 0.2 g/l Yeast Extract (pH 5.5). Indeed, both T2 and T3 media showed drastically improved *Massoia* lactone production compared to the T0 medium (FIG. 9A). Best result was observed with T3 medium, in which *Massoia* lactone level peaked at Day 7, reaching 10.268 g/l, with a volumetric productivity of 61.11 mg/hr/l. In T2 medium, *Massoia* lactone production was significantly lower than T3 medium throughout the time course. Maximal production was delayed at least 3 days with a titre of 6.924 g/l and volumetric productivity of 28.85 mg/hr/l. In contrast, maximal titre for T0 medium was only 0.441 g/l observed at Day 10, with a volumetric productivity of 1.84 mg/hr/l. The MA-21M medium performed better than T0 medium, peaking Day 9 with a titre of 1.777 g/l and volumetric productivity of 8.23 mg/hr/l. Thus, the volumetric productivity in T3 and T2 medium were 7.43-fold and 3.51-fold higher than that of A-21M medium, respectively.

In T0 and T2 medium, cells produced much higher biomass at the cost of the desired metabolite (FIG. 9B). Nitrogen source in both T2 and T3 media were rapidly consumed and became depleted after Day 2. In contrast, $NH^{4+}$ level remained high in T0 medium until Day 8 (FIG. 9C). The cells showed very different colors: cells contained strong black pigments, presumably melanin, in T2 and T3 media. In stark contrast with previous report [6], the result suggests that the production of black pigment was associated with high *Massoia* lactone production.

Example 7

Effect of Medium pH

Figure 11:
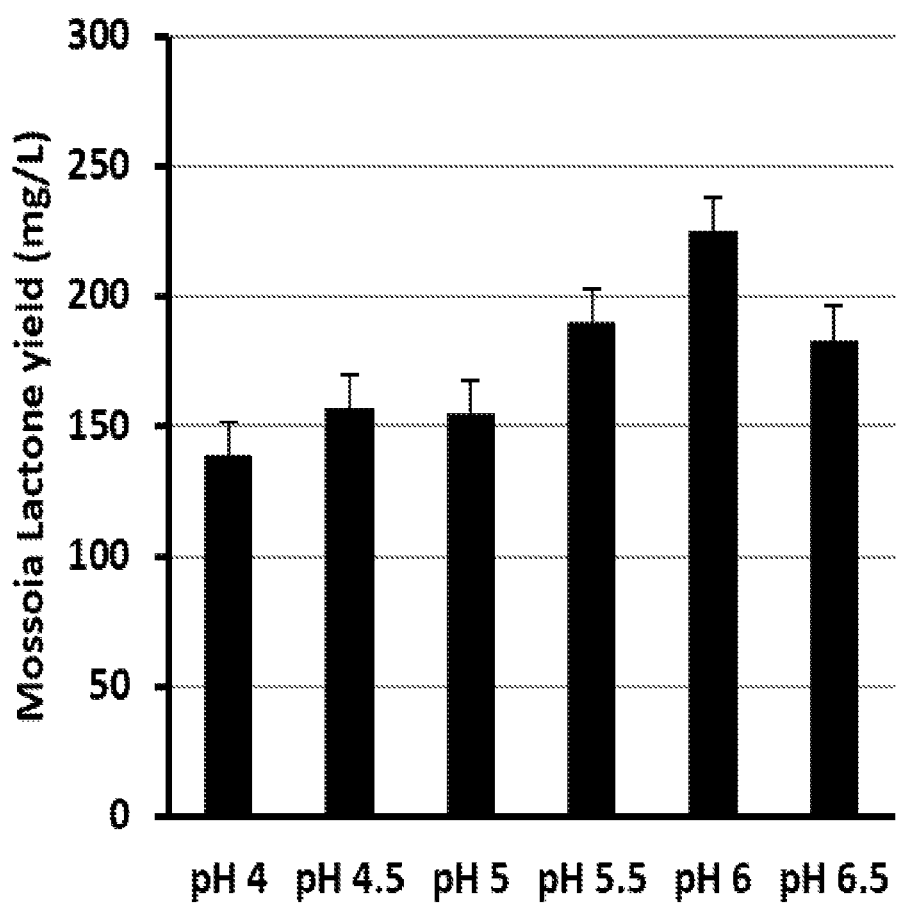
FIG. 11 shows the effect of medium pH on *Massoia* lactone yield. T2 medium was adjusted to various pH from pH 4 to pH 6.5. Cells were cultured for 5 days.

W5-2 cells cultured in YPD medium was cultured in T2 medium adjusted to various pH values ranging from pH 4 to pH 6.5. The maximal titre was observed with pH6.0. Slight reduction of yield was seen for pH 5.5 and 6.5 (FIG. 11).

Example 8

Purity of *Massoia* Lactone

Figure 12A:
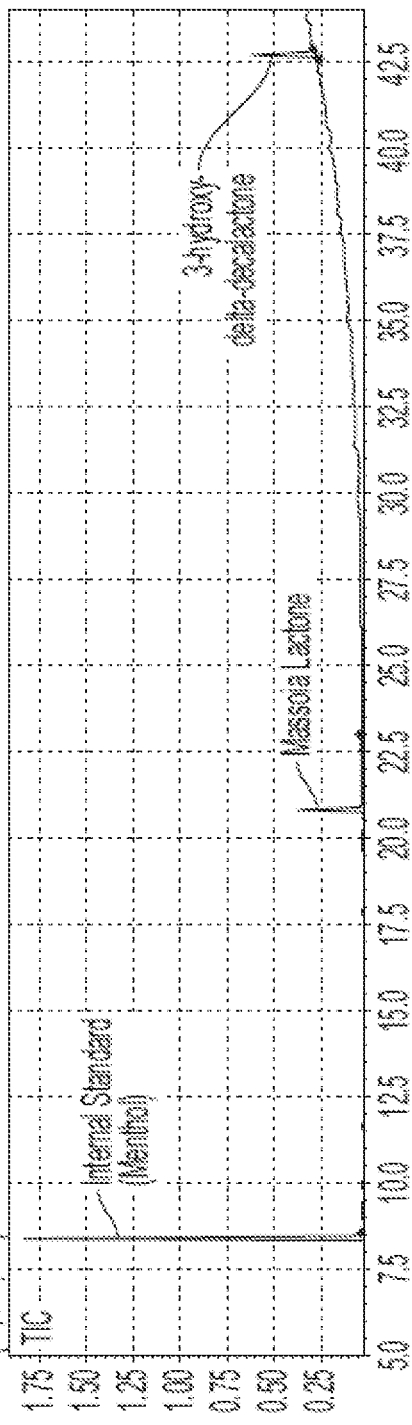
Figure 12B:
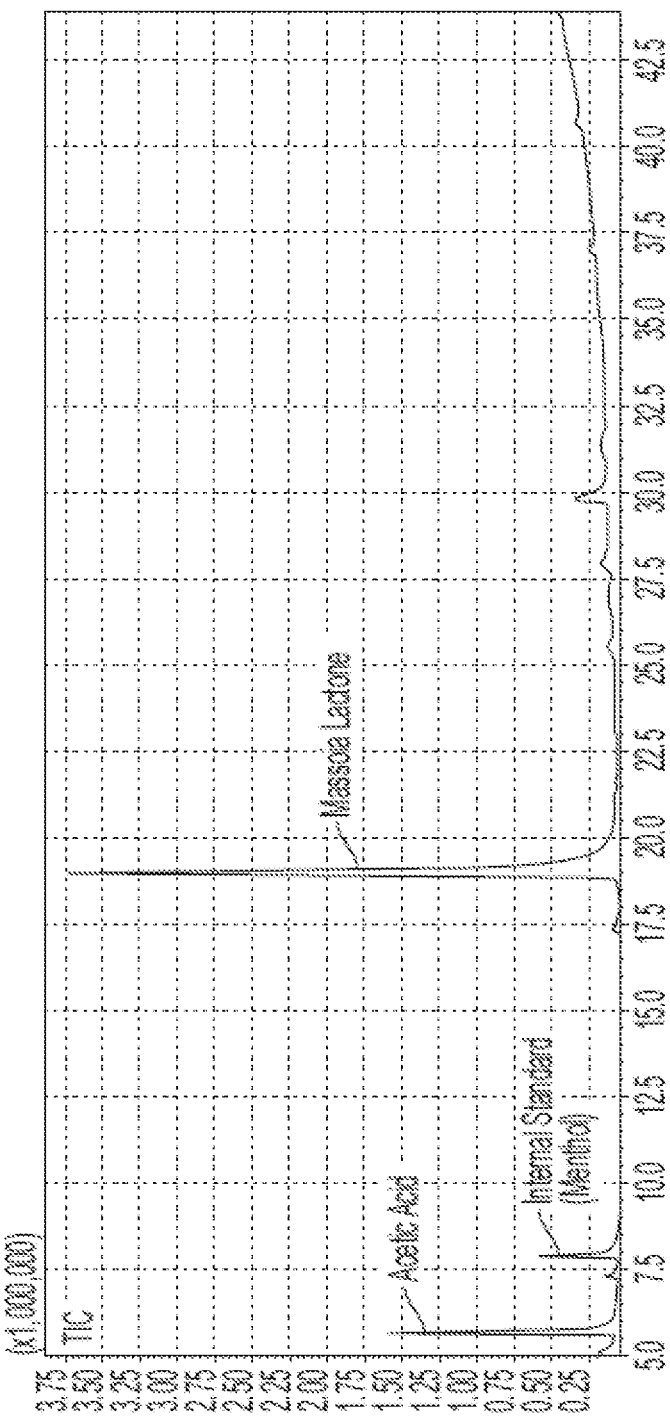
Figure 12C:
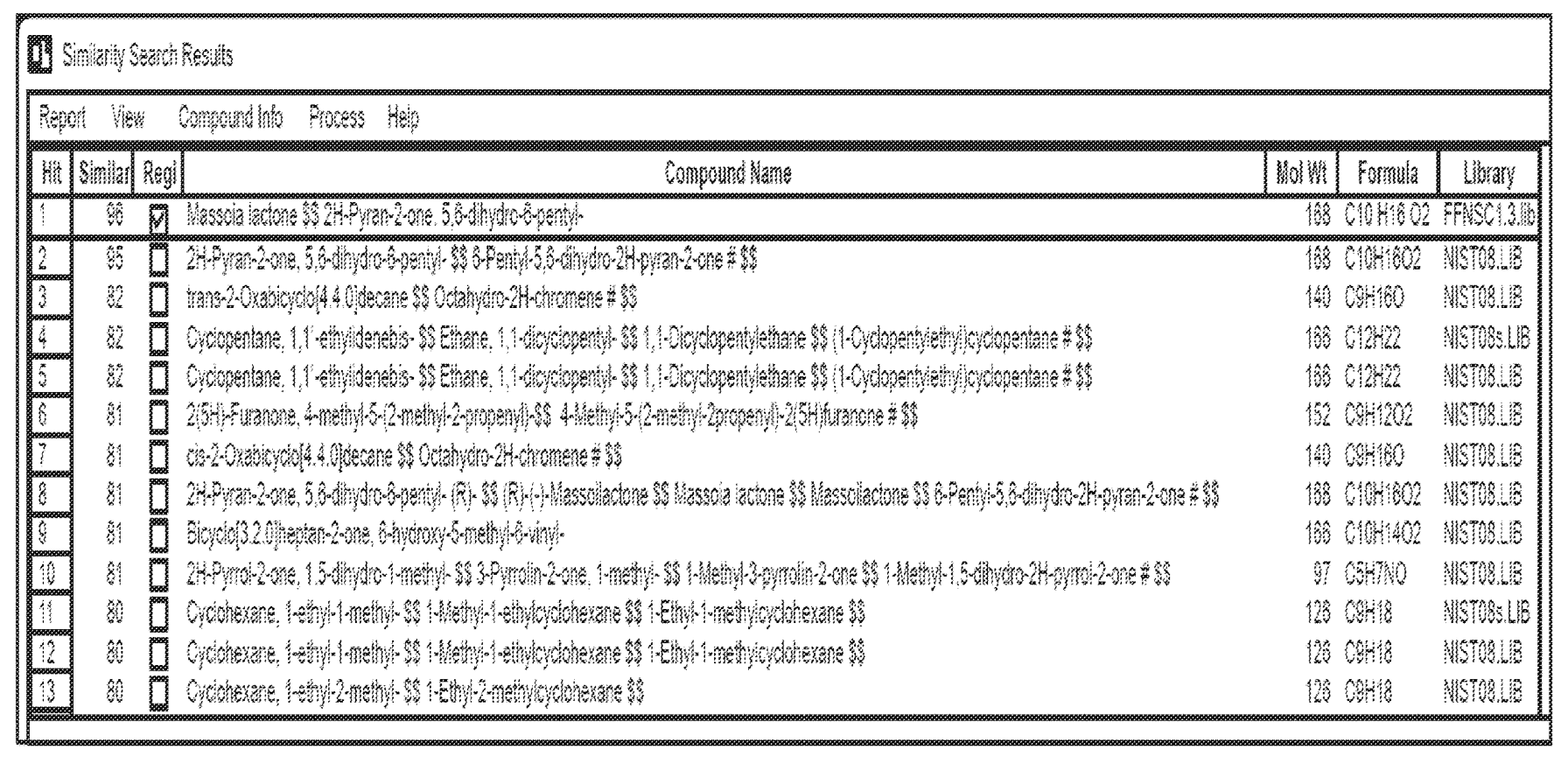

Fed-batch fermentation was performed in 2 L bioreactors using T3 media. The total fermentation broth was hydrolyzed with $H_2SO_4$. GCMS analysis of the showed the high production of a single peak of *Massoia* lactone (FIGS. 12A and 12B). This is in contrast to earlier work with *Aureobasidium* pullalan A-21M, which produced 3-hydroxyl delta-decalactone at ratio of about 1:1.7 [6].

Example 9

Comparison of House-Keeping Genes

The coding sequences (CDS) of five house-keeping genes of W5-2 strain were identified using known protein sequences of *Ustilago maydis* as the query to search against the W5-2 whole transcriptome database. SEQ ID NOs:2, 7, 8, 9 and 10 are the CDS sequence for GPD1, Actin, TEF1A, Tubulin1 and RPB1 (RNA polymerase 2, the largest subunit), respectively. There were high variations in the levels of sequence identity to homologs of different *Aureobasidium* species (Tables 10-14). Note that *A. pullulans* AY4 has been re-classified as *A. melanogenum* AY4. For example, GDP1 genomic sequence shares at least 99% identity to homologs of *A. melanogenum* species at least over 98% of SEQ ID NO:2 while the inter-species homology for GPD1 CDS is below 97% over 98% of SEQ ID NO:2 (Table 10). Similarly, TEFA genomic sequence shares at least 99% identity to homologs of *A. melanogenum* species over 99% of SEQ ID NO:8 while the inter-species homology for TEF1A CDS is below 98% over 94% of SEQ ID NO:8 (Table 12). RPB1 (SEQ ID NO:10) sequence is the most divergent.

RPB1 genomic sequence shares at least 96% identity to homologs of *A. melanogenum* species over 98% of SEQ ID NO:10 while the inter-species homology for RPB1 CDS is below 90% over 92% of SEQ ID NO:10 (Table 14).

TABLE 10

BLASTn Search Results of GPD1 (SEQ ID NO: 2)

| Description | Max score | Total score | Query cover | E value | Ident | Accession |
|---|---|---|---|---|---|---|
| *Aureobasidium melanogenum* CBS 110374 scaffold_4_c3, whole genome shotgun sequence | 1459 | 1812 | 98% | 0.0 | 99% | AYEN01000011.1 |
| *Aureobasidium pullulans* shotgun AY4 contig20, whole genome sequence | 1448 | 1795 | 98% | 0.0 | 99% | AMCU01000020.1 |
| *Aureobasidium namibiae* CBS 147.97 scaffold_2_c1, whole genome shotgun sequence | 1371 | 1692 | 98% | 0.0 | 97% | AYEM01000004.1 |
| *Aureobasidium pullulans* isolate Santander contig_514, whole genome shotgun sequence | 1321 | 1635 | 98% | 0.0 | 96% | LVWM01000514.1 |
| *Aureobasidium subglaciale* EXF-2481 scaffold_2_c1, whole genome shotgun sequence | 1315 | 1636 | 98% | 0.0 | 96% | AYYB01000004.1 |
| *Aureobasidium pullulans* EXF-150 scaffold_6_c1, whole genome shotgun sequence | 1293 | 1605 | 98% | 0.0 | 95% | AYEO01000008.1 |

TABLE 11

BLASTn Search Results of Actin (SEQ ID NO: 7)

| Description | Max score | Total score | Query cover | E value | Ident | Accession |
|---|---|---|---|---|---|---|
| *Aureobasidium pullulans* AY4 contig120, whole genome shotgun sequence | 1216 | 2960 | 99% | 0.0 | 92% | AMCU01000120.1 |
| *Aureobasidium melanogenum* CBS 110374 scaffold_3_c1, whole genome shotgun sequence | 1210 | 2960 | 99% | 0.0 | 92% | AYEN01000004.1 |
| *Aureobasidium namibiae* CBS 147.97 scaffold_18_c1, whole genome shotgun sequence | 917 | 1016 | 44% | 0.0 | 86% | AYEM01000024.1 |

TABLE 11-continued

BLASTn Search Results of Actin (SEQ ID NO: 7)

| Description | Max score | Total score | Query cover | E value | Ident | Accession |
|---|---|---|---|---|---|---|
| *Aureobasidium pullulans* isolate Santander contig_225, whole genome shotgun sequence | 828 | 1993 | 96% | 0.0 | 84% | LVWM01000225.1 |
| *Aureobasidium pullulans* EXF-150 scaffold_2_c1, whole genome shotgun sequence | 811 | 1872 | 93% | 0.0 | 84% | AYEO01000002.1 |
| *Aureobasidium subglaciale* EXF-2481 scaffold_19_c1, whole genome shotgun sequence | 614 | 735 | 39% | 4e−174 | 82% | AYYB01000022.1 |

TABLE 12

BLASTn Search Results of TEF1A (SEQ ID NO: 8)

| Description | Max score | Total score | Query cover | E value | Ident | Accession |
|---|---|---|---|---|---|---|
| *Aureobasidium melanogenum* CBS 110374 scaffold_11_c1, whole genome shotgun sequence | 2041 | 2472 | 99% | 0.0 | 99% | AYEN01000021.1 |
| *Aureobasidium pullulans* AY4 contig64, whole genome shotgun sequence | 2041 | 2472 | 99% | 0.0 | 99% | AMCU01000064.1 |
| *Aureobasidium namibiae* CBS 147.97 scaffold_4_c1, whole genome shotgun sequence | 2015 | 2368 | 94% | 0.0 | 98% | AYEM01000007.1 |
| *Aureobasidium pullulans* EXF-150 scaffold_17_c1, whole genome shotgun sequence | 1881 | 2112 | 92% | 0.0 | 96% | AYEO01000027.1 |
| *Aureobasidium subglaciale* EXF-2481 scaffold_23_c1, whole genome shotgun sequence | 1753 | 1985 | 93% | 0.0 | 94% | AYYB01000027.1 |

TABLE 13

BLASTn Search Results of Tubulin1 (SEQ ID NO: 9)

| Description | Max score | Total score | Query cover | E value | Ident | Accession |
|---|---|---|---|---|---|---|
| *Aureobasidium melanogenum* CBS 110374 scaffold_23_c2, whole genome shotgun sequence | 1284 | 2316 | 97% | 0.0 | 98% | AYEN01000040.1 |
| *Aureobasidium pullulans* AY4 contig32, whole genome shotgun sequence | 1284 | 2305 | 97% | 0.0 | 98% | AMCU01000032.1 |
| *Aureobasidium namibiae* CBS 147.97 scaffold_17_c1, whole genome shotgun sequence | 1194 | 2187 | 97% | 0.0 | 96% | AYEM01000023.1 |
| *Aureobasidium pullulans* isolate Santander contig_153, whole genome shotgun sequence | 1160 | 1981 | 92% | 0.0 | 95% | LVWM01000153.1 |
| *Aureobasidium pullulans* EXF-150 scaffold_3_c1, whole genome shotgun sequence | 1158 | 1984 | 92% | 0.0 | 95% | AYEO01000003.1 |
| *Aureobasidium subglaciale* EXF-2481 scaffold_0_c1, whole genome shotgun sequence | 1140 | 2033 | 97% | 0.0 | 95% | AYYB01000001.1 |

TABLE 14

BLASTn Search Results of RPB1 (SEQ ID NO: 10)

| Description | Max score | Total score | Query cover | E value | Ident | Accession |
|---|---|---|---|---|---|---|
| *Aureobasidium melanogenum* CBS 110374 scaffold_1_c2, whole genome shotgun sequence | 7915 | 9706 | 98% | 0.0 | 96% | AYEN01000002.1 |
| *Aureobasidium pullulans* AY4 contig81, whole genome shotgun sequence | 7866 | 9631 | 99% | 0.0 | 96% | AMCU01000081.1 |
| *Aureobasidium namibiae* CBS 147.97 scaffold_1_c2, whole shotgun sequence | 6032 | 6855 | 91% | 0.0 | 89% | AYEM01000002.1 |
| *Aureobasidium subglaciale* EXF-2481 scaffold_15_c1, whole genome shotgun sequence | 5389 | 6038 | 91% | 0.0 | 87% | AYYB01000017.1 |
| *Aureobasidium pullulans* contig_319, whole genome shotgun sequence | 5334 | 5999 | 92% | 0.0 | 86% | LVWM01000319.1 |
| *Aureobasidium pullulans* contig_233, whole genome shotgun sequence | 5334 | 5999 | 92% | 0.0 | 86% | LVWM01000233.1 |
| *Aureobasidium pullulans* contig_45, whole genome shotgun sequence | 5334 | 5999 | 92% | 0.0 | 86% | LVWM01000045.1 |
| *Aureobasidium pullulans* EXF-150 scaffold_18_c1, whole genome shotgun sequence | 5323 | 5993 | 92% | 0.0 | 86% | AYEO01000028.1 |

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the ange, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

1. Rali T, Wossa S W, Leach D N (2007) Comparative chemical analysis of the essential oil constituents in the bark, heartwood and fruits of *Cryptocarya massoy* (Oken) Kosterm.(Lauraceae) from Papua New Guinea. Molecules 12: 149-154.
2. Mineeva I (2012) Asymmetric synthesis of (−)-(R)-*Massoia* lactone, (R)-δ-decalactone, and (+)-(3R, 5R)-3-hydroxydecano-5-lactone. Formal synthesis of verbalactone. Russian Journal of Organic Chemistry 48: 977-981.
3. Gocho S, Rumi K, Tsuyoshi K (1998) Process for the production of delta decalactone. Google Patents.
4. Muys G T, Van Der Ven B, De Jonge A (1963) Preparation of Optically Active γ- and δ-Lactones by Microbiological Reduction of the Corresponding Keto Acids. Applied microbiology 11: 389-393.
5. Ramachandran P V, Reddy M V R, Brown H C (2000) Asymmetric synthesis of goniothalamin, hexadecanolide, *Massoia* lactone, and parasorbic acid via sequential allylboration-esterification ring-closing metathesis reactions. Tetrahedron Letters 41: 583-586.
6. Kurosawa T, Sakai K, Nakahara T, Oshima Y, Tabuchi T (1994) Extracellular accumulation of the polyol lipids, 3, 5-dihydroxydecanoyl and 5-hydroxy-2-decenoyl esters of arbitol and mannitol, by *Aureobasidium* sp. Bioscience, biotechnology, and biochemistry 58: 2057-2060.
7. Manitchotpisit P, Price N P J, Leathers T D, Punnapayak H (2011) Heavy oils produced by *Aureobasidium pullulans*. Biotechnology Letters 33: 1151-1157.
8. White T J, Bruns T, Lee S, Taylor J (1990) Amplification and direct sequencing of fungal ribosomal RNA genes for phylogenetics. PCR protocols: a guide to methods and applications 18: 315-322.
9. Bellemain E, Carlsen T, Brochmann C, Coissac E, Taberlet P, et al. (2010) ITS as an environmental DNA barcode for fungi: an in silico approach reveals potential PCR biases. Bmc Microbiology 10: 189.
10. Tamura K, Peterson D, Peterson N, Stecher G, Nei M, et al. (2011) MEGA5: molecular evolutionary genetics analysis using maximum likelihood, evolutionary distance, and maximum parsimony methods. Molecular biology and evolution 28: 2731-2739.
11. Saitou N, Nei M (1987) The neighbor-joining method: a new method for reconstructing phylogenetic trees. Molecular biology and evolution 4: 406-425.

12. Felsenstein J (1981) Evolutionary trees from DNA sequences: a maximum likelihood approach. Journal of molecular evolution 17: 368-376.
13. Fitch W M (1971) Toward defining the course of evolution minimum change for a specific tree topology. Systematic Biology 20: 406-416.
14. Pan J G, Kwak M Y, Rhee J S (1986) High density cell culture of *Rhodotorula glutinis* using oxygen-enriched air. Biotechnology letters 8: 715-718.
15. Liu Y, Koh C M J, Ji L (2011) Bioconversion of crude glycerol to glycolipids in *Ustilago maydis*. Bioresource technology 102: 3927-3933.
16. Carvalho A, Meireles L, Malcata F (1998) Rapid spectrophotometric determination of nitrates and nitrites in marine aqueous culture media. Analusis 26: 347-351.
17. Solorzano L (1969) Determination of ammonia in natural waters by the phenolhypochlorite method. Limnol Oceanogr 14: 799-801.
18. Cock P J, Gruning B A, Paszkiewicz K, Pritchard L (2013) Galaxy tools and workflows for sequence analysis with applications in molecular plant pathology. PeerJ 1: e167.
19. Patel R K, Jain M (2012) NGS QC Toolkit: a toolkit for quality control of next generation sequencing data. PLoS One 7: e30619.
20. Trapnell C, Roberts A, Goff L, Pertea G, Kim D, et al. (2012) Differential gene and transcript expression analysis of RNA-seq experiments with TopHat and Cufflinks. Nat Protoc 7: 562-578.
21. Trapnell C, Pachter L, Salzberg S L (2009) TopHat: discovering splice junctions with RNA-Seq. Bioinformatics 25: 1105-1111.
22. Trapnell C, Williams B A, Pertea G, Mortazavi A, Kwan G, et al. (2010) Transcript assembly and quantification by RNA-Seq reveals unannotated transcripts and isoform switching during cell differentiation. Nat Biotech 28: 511-515.
23. Grabherr M G, Haas B J, Yassour M, Levin J Z, Thompson D A, et al. (2011) Full-length transcriptome assembly from RNA-Seq data without a reference genome. Nat Biotechnol 29: 644-652.
24. Haas B J, Papanicolaou A, Yassour M, Grabherr M, Blood P D, et al. (2013) De novo transcript sequence reconstruction from RNA-seq using the Trinity platform for reference generation and analysis. Nat Protoc 8: 1494-1512.
25. Robinson M D, McCarthy D J, Smyth G K (2010) edgeR: a Bioconductor package for differential expression analysis of digital gene expression data. Bioinformatics 26: 139-140.
26. Li B, Dewey C N (2011) RSEM: accurate transcript quantification from RNA-Seq data with or without a reference genome. BMC Bioinformatics 12: 323.
27. Greenspan P, Mayer E P, Fowler S D (1985) Nile red: a selective fluorescent stain for intracellular lipid droplets. The Journal of cell biology 100: 965-973.
28. Sackett D L, Wolff J (1987) Nile red as a polarity-sensitive fluorescent probe of hydrophobic protein surfaces. Analytical biochemistry 167: 228-234.
29. Morita T, Konishi M, Fukuoka T, Imura T, Kitamoto D (2006) Discovery of *Pseudozyma rugulosa* NBRC 10877 as a novel producer of the glycolipid biosurfactants, mannosylerythritol lipids, based on rDNA sequence. Applied microbiology and biotechnology 73: 305-313.
30. Gostin C, Ohm R A, Kogej T, Sonjak S, Turk M, et al. (2014) Genome sequencing of four *Aureobasidium pullulans* varieties: biotechnological potential, stress tolerance, and description of new species. BMC genomics 15: 549.
31. Gostincar C, Ohm R A, Kogej T, Sonjak S, Turk M, et al. (2014) Genome sequencing of four *Aureobasidium pullulans* varieties: biotechnological potential, stress tolerance, and description of new species. BMC Genomics 15: 549.
32. Haas B J, Papanicolaou A, Yassour M, Grabherr M, Blood P D, et al. (2013) De novo transcript sequence reconstruction from RNA-seq using the Trinity platform for reference generation and analysis. Nature protocols 8: 1494-1512.
33. Trapnell C, Pachter L, Salzberg S L (2009) TopHat: discovering splice junctions with RNA-Seq. Bioinformatics 25: 1105-1111.
34. Takesako K, Kuroda H, Inoue T, Haruna F, Yoshikawa Y, et al. (1993) Biological properties of aureobasidin A, a cyclic depsipeptide antifungal antibiotic. The Journal of antibiotics 46: 1414-1420.
35. Slightom J L, Metzger B P, Luu H T, Elhammer A P (2009) Cloning and molecular characterization of the gene encoding the Aureobasidin A biosynthesis complex in *Aureobasidium pullulans* BP-1938. Gene 431: 67-79.
36. Lindau in Nat Pflansenfam 1(1):373, Engler & Prantl (eds.)

What is claimed is:

1. A culture for the fermentative production of *Massoia* lactone comprising an *Aureobasidium melanogenum* species in a culture medium, wherein the *Aureobasidium melanogenum* species expresses no functional Aureobasidin A synthase gene mRNA when cultured, and
   wherein the culture medium comprises:
   10.0 g/l to 15 g/l $KH_2PO_4$, 0.5 g/l to 2.0 g/l $Na_2HPO_4$, 3.5 g/l to 6.5 g/l $(NH_4)_2SO_4$, 1.0 g/l to 4.0 g/12.5 g/l $MgSO_4 \cdot 7H_2O$ and 0.10 g/l to 0.40 g/l $CaCl_2 \cdot 2H_2O$;
   at least two trace elements selected from the group consisting of $Fe^{2+}$, $Cu^{2+}$, $Zn^{2+}$ and $MoO_4^{2-}$, wherein each trace element present in the culture medium is present in an amount from 0.1 µM to 1.0 mM;
   1.5 g/l to 2.5 g/l urea; and
   a carbon source selected from the group consisting of glucose, mannose, xylose and mixtures thereof, wherein the carbon source present in the culture medium from 4% to 12%;
   wherein the culture medium has a pH from 5.5 to 6.5.

2. The culture of claim 1, wherein the *Aureobasidium melanogenum* strain is *Aureobasidium melanogenum* W5-2 deposited with Agricultural Research Culture Collection (NRRL) and assigned Accession Number NRRL 67063.

3. The culture of claim 2, further comprising more than 10 g/l of *Massoia* lactone.

4. The culture of claim 3, wherein the amount of crude *Massoia* lactone is at least 11 g/l.

5. The culture of claim 2, wherein the amount of crude *Massoia* lactone is 10 g/l to 25 g/l.

6. The culture of claim 1, wherein the *Aureobasidium melanogenum* strain shares 100% identity with at least 98% of the nucleotide sequence of SEQ ID NO: 2, or wherein the *Aureobasidium melanogenum* strain shares 100% identity with at least 99% of the nucleotide sequence of SEQ ID NO: 8, or wherein the *Aureobasidium melanogenum* strain shares 100% identity with at least 98% of the nucleotide sequence of SEQ ID NO: 10.

7. The culture of claim 6, further comprising more than 10 g/l of *Massoia* lactone.

8. The culture of claim 7, wherein the amount of crude *Massoia* lactone is at least 11 g/l.

9. The culture of claim 6, wherein the amount of crude *Massoia* lactone is 10 g/l to 25 g/l.

10. The culture of claim 1, further comprising more than 10 g/l of *Massoia* lactone.

11. The culture of claim 10, wherein the amount of crude *Massoia* lactone is at least 11 g/l.

12. The culture of claim 10, wherein the amount of crude *Massoia* lactone is 10 g/l to 25 g/l.

13. The culture of claim 1, wherein the *Aureobasidium melanogenum* GDP1 genomic sequence shares at least 97.5% identity with SEQ ID NO:2, and/or
  wherein the *Aureobasidium melanogenum* TEF1A genomic sequence shares at least 98% identity with SEQ ID NO:8, and/or
  wherein the *Aureobasidium melanogenum* RBP1 genomic sequence shares at least 96% identity with SEQ ID NO:10.

14. The culture of claim 1, wherein the culture medium comprises 12.5 g/l $KH_2PO_4$.

15. The culture of claim 1, wherein the culture medium comprises 1.0 g/l $Na_2HPO_4$.

16. The culture of claim 1, wherein the culture medium comprises 5.0 g/l $(NH_4)_2SO_4$.

17. The culture of claim 1, wherein the culture medium comprises 2.5 g/l $MgSO_4 \cdot 7H_2O$.

18. The culture of claim 1, wherein the culture medium comprises 0.25 g/l $CaCl_2 \cdot 2H_2O$.

19. The culture of claim 1, wherein the culture medium comprises each trace element in an amount from 1.0 µM to 1.0 mM.

20. The culture of claim 1, wherein the culture medium comprises 1.8 g/l to 2.2 g/l urea, and/or 5% to 12% of the carbon source.

\* \* \* \* \*